US007745215B2

(12) United States Patent
Shirwan

(10) Patent No.: US 7,745,215 B2
(45) Date of Patent: Jun. 29, 2010

(54) METHODS AND COMPOSITIONS FOR EXPANDING T REGULATORY CELLS

(75) Inventor: Haval Shirwan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 11/635,087

(22) Filed: Dec. 7, 2006

(65) Prior Publication Data
US 2007/0172947 A1 Jul. 26, 2007

Related U.S. Application Data

(60) Provisional application No. 60/748,177, filed on Dec. 8, 2005, provisional application No. 60/758,391, filed on Jan. 12, 2006, provisional application No. 60/799,642, filed on May 12, 2006, provisional application No. 60/799,643, filed on May 12, 2006.

(51) Int. Cl.
*C12N 5/06* (2006.01)

(52) U.S. Cl. ..................................................... 435/325

(58) Field of Classification Search ........................ None
See application file for complete search history.

(56) References Cited

U.S. PATENT DOCUMENTS

| 6,232,088 B1 * | 5/2001 | Franklin et al. ............... 435/18 |
| 7,238,360 B2 | 7/2007 | Shirwan |
| 7,598,345 B2 | 10/2009 | Shirwan et al. |
| 2003/0219419 A1 | 11/2003 | Shirwan |
| 2006/0052295 A1 | 3/2006 | Terman |

FOREIGN PATENT DOCUMENTS

| EP | 1 736 482 A1 | 12/2006 |
| WO | WO 00/67788 A2 | 11/2000 |
| WO | WO 02/02751 | 1/2002 |
| WO | WO 2007/000675 A2 | 1/2007 |

OTHER PUBLICATIONS

Lynch D., Immunological Reviews, 2008, 222: 277-286.*
Asai et al., "A human biotin acceptor domain allows site-specific conjugation of an enzyme to an antibody-avidin fusion protein for targeted drug delivery", *Biomolecular Engineering*, vol. 21, (1995), pp. 145-155.
Huang et al., "Improved Immunogenicity of a Self Tumor Antigen by Covalent Linkage to CD40 Ligand", *Int. J. Cancer*, vol. 108, (2004), pp. 696-703.
Huang et al., "Enhanced antitumor immunity by fusion of CTLA-4 to a self tumor antigen", *Blood*, vol. 96, No. 12, (Dec. 2000), pp. 3663-3670.
Rohrbach et al., "Targeted Delivery of the ErbB2/HER2 Tumor Antigen to Professional APCs Results in Effective Antitumor Immunity", *The Journal of Immunology*, vol. 174, (2005), pp. 5481-5489.
International Search Report for International Application No. PCT/US2006/046662; mailed Nov. 13, 2007; (4 pgs.).

Office Action issued Apr. 21, 2008, in U.S. Appl. No. 11/635,066, 12 sheets.
Asai, T. et al.; "A human biotin acceptor domain allows site-specific conjugation o fan enzyme to an antibody-avidin fusion protein for targeted drug delivery", Biomolecular Engineering, vol. 21, No. 6, pp. 145-155 (2005).
Huang, T-H, "Improved immunogenicity of a self-tumor antigen by covalent linkage to CD40 ligand", Intl J. Cancer, vol. 108, pp. 696-703 (2004).
Huang, T-H, et al.; "Enhanced antitumor immunity by fusion of CTLA-4 to a self tumor antigen", Blood, vol. 96, No. 12, pp. 3663-3670 (2000).
Rohrbach, F., et al., "Targeted delivery of the ErbB2/HER2 tumor antigen to professional APCs results in effective antitumor immunity", J. Immuno., vol. 174, No. 9, pp. 5481-5489 (2005).
Askenasy, Nadir et al., "Display of Fas Ligand Protein on Cardiac Vasculature as a Novel Means of Regulating Allograft Rejection", *Circulation*, vol. 107, No. 11, pp. 1525-1531 (2003).
Briones, Javier et al., "Antitumor Immunity After Vaccination With B Lymphoma Cells Overexpressing a Triad of Costimulatory Molecules", *Journal of the National Cancer Institute*, vol. 95, No. 7, pp. 548-555 (2003).
Kilinc, Mehmet O. et al., "Generation of a multimeric form of CD40L with potent immunostimulatory activity using streptavidin as a chaperon", *Experimental and Molecular Pathology*, vol. 80, No. 3, pp. 252-261 (2006).
Hodge, James W. et al., "A Triad of Costimulatory Molecules Synergize to Amplify T-Cell Activation", *Cancer Research*, vol. 59, pp. 5800-5807 (1999).
Singh, Narendra P. et al., "A Novel Approach to Cancer Immunotherapy: Tumor Cells Decorated with CD80 Generate Effective Antitumor Immunity", *Cancer Research*, vol. 63, No. 14, pp. 4067-4073 (2003).
Singh, Narendra P. et al., "ProtEx™: A Novel Technology to Display Exogenous Proteins on the Cell Surface for Immunomodulation", *Ann. N.Y. Acad. Sci.*, vol. 1056, pp. 344-358 (2005).
Singh, Narendra P. et al., "Primary Tumor Cells Resected from Cancer Patients and Decorated with a Novel Form of CD80 Protein Serve as Effective Antigen-Presenting Cells for the Induction of Autologous T Cell Immune Responses Ex Vivo", *Human Gene Therapy*, vol. 17, No. 3, pp. 334-346 (2006).
Yolcu, Esma S. et al., "Cell Membrane Modification for Rapid Display of Proteins as a novel Means of Immunomodulation: FasL-Decorated Cells Prevent Islet Graft Rejection", *Immunity*, 17:795-808 (2002).

(Continued)

*Primary Examiner*—Ilia Ouspenski
(74) *Attorney, Agent, or Firm*—Foley & Lardner LLP

(57) ABSTRACT

The present invention provides methods and compositions for expanding Treg cells ex vivo or in vivo using one or more conjugates comprising a costimulatory moiety that stimulates at least one of three signals involved in Treg cell development and/or using dendritic cells pulsed with antigens and modified to display TGF-β, or hematopoetic stem cells or bone marrow cells modified to display TGF-β. The methods and compositions are useful, for example, in the treatment and prevention of autoimmune disease, including Type 1 diabetes and in preventing foreign graft rejection, as well as to establish mixed chimerism, induce tolerance to autoantigens, alloantigens or xenoantigens, beta cell regeneration, prevention of foreign graft rejection, and treatment of a genetically inherited hematopoietic disorder.

9 Claims, 22 Drawing Sheets

OTHER PUBLICATIONS

Moro, Monica et al., "Induction of Therapeutic T-Cell Immunity by tumor Targeting with Soluble Recombinant B7-Immunoglobulin Costimulatory Molecules", *Cancer Research*, vol. 59, No. 11, pp. 2650-2656 (1999).

Symington, Frank W. et al., "Expression and Function of B7 on Human Epidermal Langerhans Cells", *Journal of Immunology*, vol. 150, No. 4, pp. 1286-1295 (1993).

Kudo-Saito, Chie et al., "Intratumoral Vaccination and Diversified Subcutaneous/Intratumoral Vaccination with Recombinant Poxviruses Costimulatory Molecules", *Clincal Cancer Research*, vol. 10, No. 3, pp. 1090-1099 (2004).

De Jong, Marg O. et al., "Biotinylation of interleukin-s (IL-2) for flow cytometric analysis of IL-2 receptor expression", *J. Immunol. Methods*, 184:101-112 (1995).

Jordan, Robert A. et al., "Production of Genetically Engineered Biotinylated Interleukin-s and Its Applications in a Rapid Nonradioactive Assay for T-Cell Activation", *Clin.Diag. Lab. Immunol.*, vol. 10, No. 3, pp. 339-344 (2003).

U.S. Appl. No. 12/553,770, filed Sep. 3, 2009, Shirwan et al.

U.S. Appl. No. 12/499,488, filed Jul. 8, 2009, Shirwan et al.

Notice of Allowance issued on Jun. 5, 2009, by the Examiner in U.S. Appl. No. 11/635,066 (US 7,598,345).

Office Action issued on Feb. 24, 2009, by the Examiner in U.S. Appl. No. 11/635,066 (US 7,598,345).

International Search Report issued on Sep. 21, 2007 in application No. PCT/US2006/046663 (corresponding to US 7,598,345).

Rabu et al., "Production of Recombinant Human Trimeric CD137L (4-1 BBL): Cross Linking is Essential to its T Cell Co-Stimulation Activity," *The Journal of Biological Chemistry*, vol. 280, No. 50, pp. 41472-41481 (Dec. 16, 2005).

\* cited by examiner

FIG. 1A

CSA-LIGHT Nucleotide Construct (SEQ ID NO:1)

ACCCGTGTGTAAAGCCGCGTTTCCAAAATGTATAAAACCGAGAGCATCTGGCCAATGTGCAT
CAGTTGTGGTCAGCAGCAAAATCAAGTGAATCATCTCAGTGCAACTAAAGGGGGGATCCGAT
CTCAATATGAAGTTATGCATATTACTGGCCGTCGTGGCCTTTGTTGGCCTCTCGCTCGGGAG
ATCTCATCATCACCATCACCATATCACCGGCACCTGGTACAACCAGCTCGGCTCGACCTTCA
TCGTGACCGCGGGCGCCGATGGCGCCCTGACCGGAACCTACGAGTCGGCCGTCGGCAACGCC
GAGAGCCGCTACGTCCTGACCGGTCGTTACGACAGCGCCCCGGCCACCGACGGCAGCGGCAC
CGCCCTCGGTTGGACGGTGGCCTGGAAGAATAACTACCGCAACGCCCACTCCGCGACCACGT
GGAGCGGCCAGTACGTCGGCGGCGCCGAGGCGAGGATCAACACCCAGTGGCTGCTGACCTCC
GGCGCCACCGAGGCCAACGCCTGGAAGTCCACGCTGGTCGGCCACGACACCTTCACCAAGGT
GAAGCCGTCCGCCGCCTCAAGCGAATTCCGCACCGAGCCTCGGCCAGCGCTCACAATCACCA
CCTCGCCCAACCTGGGTACCCGAGAGAATAATGCAGACCAGGTCACCCCTGTTTCCCACATT
GGCTGCCCCAACACTACACAACAGGGCTCTCCTGTGTTCGCCAAGCTACTGGCTAAAAACCA
AGCATCGTTGTGCAATACAACTCTGAACTGGCACAGCCAAGATGGAGCTGGGAGCTCATACC
TATCTCAAGGTCTGAGGTACGAAGAAGACAAAAAGGAGTTGGTGGTAGACAGTCCCGGGCTC
TACTACGTATTTTTGGAACTGAAGCTCAGTCCAACATTCACAAACACAGGCCACAAGGTGCA
GGGCTGGGTCTCTCTTGTTTTGCAAGCAAAGCCTCAGGTAGATGACTTTGACAACTTGGCCC
TGACAGTGGAACTGTTCCCTTGCTCCATGGAGAACAAGTTAGTGGACCGTTCCTGGAGTCAA
CTGTTGCTCCTGAAGGCTGGCCACCGCCTCAGTGTGGGTCTGAGGGCTTATCTGCATGGAGC
CCAGGATGCATACAGAGACTGGGAGCTGTCTTATCCCAACACCACCAGCTTTGGACTCTTTC
TTGTGAAACCCGACAACCCATGGGAATGAGAACTATCCTTCTTGTGACTCCTAGTTGCTAAG
TCCTCAAGCTGCTATGCTCGAGTCTAGAGGGCCCTTCGAAGGTAAGCCTATCCCTAACCCTC
TCCTCGGTCTCGATTCTACGCGTACCGGTCATCATCACCATCACCATTGAGTTTAAACCCGC
TG

FIG. 1B

CSA-LIGHT Fusion Protein (SEQ ID NO:2)

MKLCILLAVVAFVGLSLGRSHHHHHHITGTWYNQLGSTFIVTAGADGALTGTYESAVGNAES
RYVLTGRYDSAPATDGSGTALGWTVAWKNNYRNAHSATTWSGQYVGGAEARINTQWLLTSGA
TEANAWKSTLVGHDTFTKVKPSAASSEFQRSHQANPAAHLTGANASLIGIGGPLLWETRLGL
AFLRGLTYHDGALVTMEPGYYYVYSKVQLSGVGCPQGLANGLPITHGLYKRTSRYPKELELL
VSRRSPCGRANSSRVWWDSSFLGGVVHLEAGEEVVVRVPGNRLVRPRDGTRSYFGAFMV

FIG. 2A

CD80-CSA Nucleotide Construct (SEQ ID NO:3)

CATCTCCAGTGCAACTAAAGGGGGGATCCGATCTCAATATGAAGTTATGC
ATATTACTGGCCGTCGTGGCCTTTGTTGGCCTCTCGCTCGGGAGATCTAT
CCACGTGACCAAGGAAGTGAAAGAAGTGGCAACGCTGTCCTGTGGTCACA
ATGTTTCTGTTGAAGAGCTGGCACAAACTCGCATCTACTGGCAAAAGGAG
AAGAAAATGGTGCTGACTATGATGTCTGGGACATGAATATATGGCCCGA
GTACAAGAACCGGACCATCTTTGATATCACTAATAACCTCTCCATTGTGA
TCCTGGCTCTGCGCCCATCTGACGAGGGCACATACGAGTGTGTTGTTCTG
AAGTATGAAAAGACGCTTTCAAGCGGGAACACCTGGCTGAAGTGACGTT
ATCAGTCAAAGCTGACTTCCCTACACCTAGTATATCTGACTTTGAAATTC
CAACTTCTAATATTAGAAGGATAATTTGCTCAACCTCTGGAGGTTTTCCA
GAGCCTCACCTCTCCTGGTTGGAAAATGGAGAAGAATTAAATGCCATCAA
CACAACAGTTTCCCAAGATCCTGAAACTGAGCTCTATGCTGTTAGCAGCA
AACTGGATTTCAATATGACAACCAACCACAGCTTCATGTGTCTCATCAAG
TATGGACATTTAAGAGTGAATCAGACCTTCAACTGGAATACAACCAAGCA
AGAGAGATCTCATCATCACCATCACCATATCACCGGCACCTGGTACAACC
AGCTCGGCTCGACCTTCATCGTGACCGCGGGCGCCGACGGCGCCCTGACC
GGAACCTACGAGTCGGCCGTCGGCAACGCCGAGAGCCGCTACGTCCTGAC
CGGTCGTTACGACAGCGCCCCGGCCACCGACGGCAGCGGCACCGCCCTCG
GTTGGACGGTGGCCTGGAAGAATAACTACCGCAACGCCCACTCCGCGACC
ACGTGGAGCGGCCAGTACGTCGGCGGCGCCGAGGCGAGGATCAACACCCA
GTGGCTGTTGACCTCCGGCGCCACCGAGGCCAACGCCTGGAAGTCCACGC
TGGTCGGCCACGACACCTTCACCAAGGTGAAGCCGTCCGCCGCCTCAAGC
CGAATTCTGCAGATATCCAGCACAGTGGCGGCCGCTCGAGTCTAGAGGGC
CCTTCGAAGGTAAGCCTATCCCTAACCCTCTCCTCGGTCTCGATTCTACG
CGTACCGGTCATCATCACCATCACCATTGAGTTTAAACCCGCTGATCAGC
CTCGACTGTGCTTTCTAA

FIG. 2B

CD80-CSA Fusion Protein (SEQ ID NO:4)

CSA-4-1BBL Nucleotide Construct (SEQ ID NO:5)

TTCATGCAACTAAAGGGGGGATCCGATCTCAATATGAAGTTATGCATATT
ACTGGCCGTCGTGGCCTTTGTTGGCCTCTCGCTCGGGAGATCTCATCATC
ACCATCACCATATCACCGGCACCTGGTACAACCAGCTCGGCTCGACCTTC
ATCGTGACCGCGGGCGCCGATGGCGCCCTGACCGGAACCTACGAGTCGGC
CGTCGGCAACGCCGAGAGCCGCTACGTCCTGACCGGTCGTTACGACAGCG
CCCCGGCCACCGACGGCAGCGGCACCGCCCTCGGTTGGACGGTGGCCTGG
AAGAATAACTACCGCAACGCCCACTCCGCGACCACGTGGAGCGGCCAGTA
CGTCGGCGGCGCCGAGGCGAGGATCAACACCCAGTGGCTGTTGACCTCCG
GCGCCACCGAGGCCAACGCCTGGAAGTCCACGCTGGTCGGCCACGACACC
TTCACCAAGGTGAAGCCGTCCGCCGCCTCAAGCGAATTCCGCACCGAGCC
TCGGCCAGCGCTCACAATCACCACCTCGCCCAACCTGGGTACCCGAGAGA
ATAATGCAGACCAGGTCACCCCTGTTTCCCACATTGGCTGCCCCAACACT
ACACAACAGGGCTCTCCTGTGTTCGCCAAGCTACTGGCTAAAAACCAAGC
ATCGTTGTGCAATACAACTCTGAACTGGCACAGCCAAGATGGAGCTGGGA
GCTCATACCTATCTCAAGGTCTGAGGTACGAAGAAGACAAAAGGAGTTG
GTGGTAGACAGTCCCGGGCTCTACTACGTATTTTTGGAACTGAAGCTCAG
TCCAACATTCACAAACACAGGCCACAAGGTGCAGGGCTGGGTCTCTCTTG
TTTTGCAAGCAAAGCCTCAGGTAGATGACTTTGACAACTTGGCCCTGACA
GTGGAACTGTTCCCTTGCTCCATGGAGAACAAGTTAGTGGACCGTTCCTG
GAGTCAACTGTTGCTCCTGAAGGCTGGCCACCGCCTCAGTGTGGGTCTGA
GGGCTTATCTGCATGGAGCCCAGGATGCATACAGAGACTGGGAGCTGTCT
TATCCCAACACCACCAGCTTTGGACTCTTTCTTGTGAAACCCGACAACCC
ATGGGAATGAGAACTATCCTTCTTGTGACTCCTAGTTGCTAAGTCCTCAA
GCTGCTATGCTCGAGTCTAGAGGGCCCTTCGAAGGTAAGCCTATCCCTAA
CCCTCTCCTCGGTCTCGATTCTACGCGTACCGGTCATCATCACCATCACC
ATTGAGTTTAAACCCGCTGATCAGCCTCGACTGTGCCTTTCTAA

FIG. 3B

CSA-murine 4-1BBL Fusion Protein (SEQ ID NO:6)

CSA-human 4-1BBL Fusion Protein (SEQ ID NO:7)

MKLCILLAVVAFVGLSLGRSHHHHHH**ITGTWYNQLGSTFIVTAGADGALTGTYESAVGNAESRY
VLTGRYDSAPATDGSGTALGWTVAWKNNYRNAHSATTWSGQYVGGAEARINTQWLLTSGATEAN
AWKSTLVGHDTFTKVKPSAASS**EFLACPWAVSGARASPGSAASPRLREGPELSPDDPAGLLDLR
QGMFAQLVAQNVLLIDGPLSWYSDPGLAGVSLTGGLSYKEDTKELVVAKAGVYYVFFQLELRRV
VAGEGSGSVSLALHLQPLRSAAGAAALALTVDLPPASSEARNSAFGFQGRLLHLSAGQRLGVHL
HTEARARHAWQLTQGATVLGLFRVTPEIPAGLPSPRSE

FIG. 5A

CSA-B7.2 Nucleotide Construct (SEQ ID NO:8)

CATCTCCAGTGCAACTAAAGGGGGGATCCGATCTCAATATGAAGTTATGCATATTACTGGCC
GTCGTGGCCTTTGTTGGCCTCTCGCTCGGGAGATCTGCTCCTCTGAAGATTCAAGCTTATTT
CAATGAGACTGCAGACCTGCCATGCCAATTTGCAAACTCTCAAAACCAAAGCCTGAGTGAGC
TAGTAGTATTTTGGCAGGACCAGGAAAACTTGGTTCTGAATGAGGTATACTTAGGCAAAGAG
AAATTTGACAGTGTTCATTCCAAGTATATGGGCCGCACAAGTTTTGATTCGGACAGTTGGAC
CCTGAGACTTCACAATCTTCAGATCAAGGACAAGGGCTTGTATCAATGTATCATCCATCACA
AAAAGCCCACAGGAATGATTCGCATCCACCAGATGAATTCTGAACTGTCAGTGCTTGCTAAC
TTCAGTCAACCTGAAATAGTACCAATTTCTAATATAACAGAAAATGTGTACATAAATTTGAC
CTGCTCATCTATACACGGTTACCCAGAACCTAAGAAGATGAGTGTTTTGCTAAGAACCAAGA
ATTCAACTATCGAGTATGATGGTATTATGCAGAAATCTCAAGATAATGTCACAGAACTGTAC
GACGTTTCCATCAGCTTGTCTGTTTCATTCCCTGATGTTACGAGCAATATGACCATCTTCTG
TATTCTGGAAACTGACAAGACGCGGCTTTTATCTTCACCTTTCTCTATAGAGCTTGAGGACC
CTCAGCCTCCCCCAGACCACATTCCTAGATCTCATCATCACCATCACCATATCACCGGCACC
TGGTACAACCAGCTCGGCTCGACCTTCATCGTGACCGCGGGCGCCGACGGCGCCCTGACCGG
AACCTACGAGTCGGCCGTCGGCAACGCCGAGAGCCGCTACGTCCTGACCGGTCGTTACGACA
GCGCCCCGGCCACCGACGGCAGCGGCACCGCCCTCGGTTGGACGGTGGCCTGGAAGAATAAC
TACCGCAACGCCCACTCCGCGACCACGTGGAGCGGCCAGTACGTCGGCGGCGCCGAGGCGAG
GATCAACACCCAGTGGCTGTTGACCTCCGGCGCCACCGAGGCCAACGCCTGGAAGTCCACGC
TGGTCGGCCACGACACCTTCACCAAGGTGAAGCCGTCCGCCGCCTCAAGCCGAATTCTGCAG
ATATCCAGCACAGTGGCGGCCGCTCGAGTCTAGAGGGCCCTTCGAAGGTAAGCCTATCCCTA
ACCCTCTCCTCGGTCTCGATTCTACGCGTACCGGTCATCATCACCATCACCATTGAGTTTAA
ACCCGCTGATCAGCCTCGACTGTGCTTTCTAA

FIG. 5B

B7.2-CSA Fusion Protein (SEQ ID NO:9)

MKLCILLAVVAFVGLSLGRSAPLKIQAYFNETADLPCQFANSQNQSLSELVVFWQDQENLVLNE
VYLGKEKFDSVHSKYMGRTSFDSDSWTLRLHNLQIKDKGLYQCIIHHKKPTGMIRIHQMNSELS
VLANFSQPEIVPISNITENVYINLTCSSIHGYPEPKKMSVLLRTKNSTIEYDGIMQKSQDNVTE
LYDVSISLSVSFPDVTSNMTIFCILETDKTRLLSSPFSIELEDPQPPPDHIPRSHHHHHHITGT
WYNQLGSTFIVTAGADGALTGTYESAVGNAESRYVLTGRYDSAPATDGSGTALGWTVAWKNNYR
NAHSATTWSGQYVGGAEARINTQWLLTSGATEANAWKSTLVGHDTFTKVKPSAASSRILQISST
VAAARV

FIG. 6A

IL-2-CSA Nucleotide Sequence (SEQ ID NO:10)

```
GCACCTACTTCAAGTTCTACAAAGAAAACACAGCTACAACTGGAGCATTTACTGCTGGATTT
ACAGATGATTTTGAATGGAATTAATAATTACAAGAATCCCAAACTCACCAGGATGCTCACAT
TTAAGTTTTACATGCCCAAGAAGGCCACAGAACTGAAACATCTTCAGTGTCTAGAAGAAGAA
CTCAAACCTCTGAAGGAAGTGCTAAATTTAGCTCAAAGCAAAAACTTTCACTTAAGACCCAG
GGACTTAATCAGCAATATCAACGTAATAGTTCTGGAACTAAAGGGATCTGAAACAACATTCA
TGTGTGAATATGCTGATGAGACAGCAACCATTGTAGAATTTCTGAACAGATGGATTACCTTT
TCTCAAAGCATCATCTCAACACTAACTGGTAGATCTCATCATCACCATCACCATATCACCGG
CACCTGGTACAACCAGCTCGGCTCGACCTTCATCGTGACCGCGGGCGCCGACGGCGCCCTGA
CCGGAACCTACGAGTCGGCCGTCGGCAACGCCGAGAGCCGCTACGTCCTGACCGGTCGTTAC
GACAGCGCCCCGGCCACCGACGGCAGCGGCACCGCCCTCGGTTGGACGGTGGCCTGGAAGAA
TAACTACCGCAACGCCCACTCCGCGACCACGTGGAGCGGCCAGTACGTCGGCGGCGCCGAGG
CGAGGATCAACACCCAGTGGCTGTTGACCTCCGGCACCACCGAGGCCAACGCCTGGAAGTCC
ACGCTGGTCGGCCACGACACCTTCACCAAGGTGAAGCCGTCCGCCGCCTCAA
```

FIG. 6B

IL-2-CSA Fusion Protein (SEQ ID NO:11)

*APTSSSTKKTQLQLEHLLLDLQMILNGIN

FIG. 7A

TGF-β-CSA Nucleotide Sequence (SEQ ID NO:12)

GCCCTGGACACCAACTATTGCTTCAGCTCCACGGAGAAGAACTGCTGCGTGCGGCAGCTGTA
CATTGACTTCCGCAAGGACCTCGGCTGGAAGTGGATCCACGAGCCCAAGGGCTACCATGCCA
ACTTCTGCCTCGGGCCCTGCCCCTACATTTGGAGCCTGGACACGCAGTACAGCAAGGTCCTG
GCCCTGTACAACCAGCATAACCCGGGCGCCTCGGCGGCGCCGTGCTGCGTGCCGCAGGCGCT
GGAGCCGCTGCCCATCGTGTACTACGTGGGCCGCAAGCCCAAGGTGGAGCAGCTGTCCAACA
TGATCGTGCGCTCCTGCAAGTGCAGCAGATCTCATCATCACCATCACCATATCACCGGCACC
TGGTACAACCAGCTCGGCTCGACCTTCATCGTGACCGCGGGCGCCGACGGCGCCCTGACCGG
AACCTACGAGTCGGCCGTCGGCAACGCCGAGAGCCGCTACGTCCTGACCGGTCGTTACGACA
GCGCCCCGGCCACCGACGGCAGCGGCACCGCCCTCGGTTGGACGGTGGCCTGGAAGAATAAC
TACCGCAACGCCCACTCCGCGACCACGTGGAGCGGCCAGTACGTCGGCGGCGCCGAGGCGAG
GATCAACACCCAGTGGCTGCTGACCTCCGGCACCACCGAGGCCAACGCCTGGAAGTCCACGC
TGGTCGGCCACGACACCTTCACCAAGGTGAAGCCGTCCGCCGCCTC

FIG. 7B

TGF-β-CSA Fusion Protein (SEQ ID NO:13)

*ALDTNYCFSSTEKNCCVRQLYIDFRKDLGWKWIHEPKGYHANFCLGPCPYIWSLDTQYSKVL*
*ALYNQHNPGASAAPCCVPQALEPLPIVYYVGRKPKVEQLSNMIVRSCKCS*RSHHHHHH<u>ITGT</u>
<u>WYNQLGSTFIVTAGADGALTGTYESAVGNAESRYVLTGRYDSAPATDGSGTALGWTVAWKNN</u>
<u>YRNAHSATTWSGQYVGGAEARINTQWLLTSGTTEANAWKSTLVGHDTFTKVKPSAAS</u>

Fig. 8A
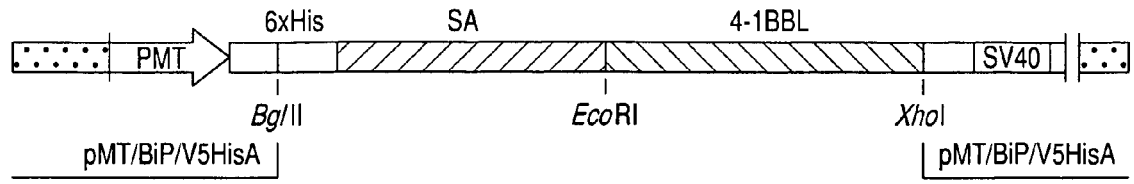
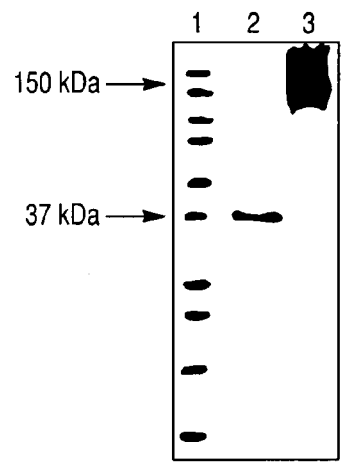
Fig. 8B
Fig. 8D
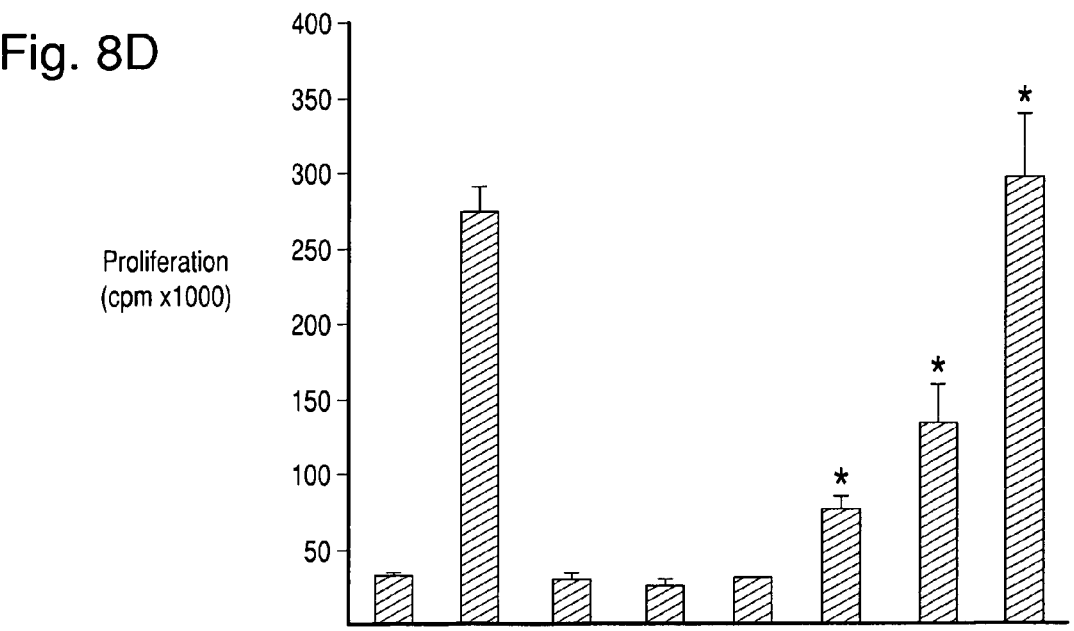

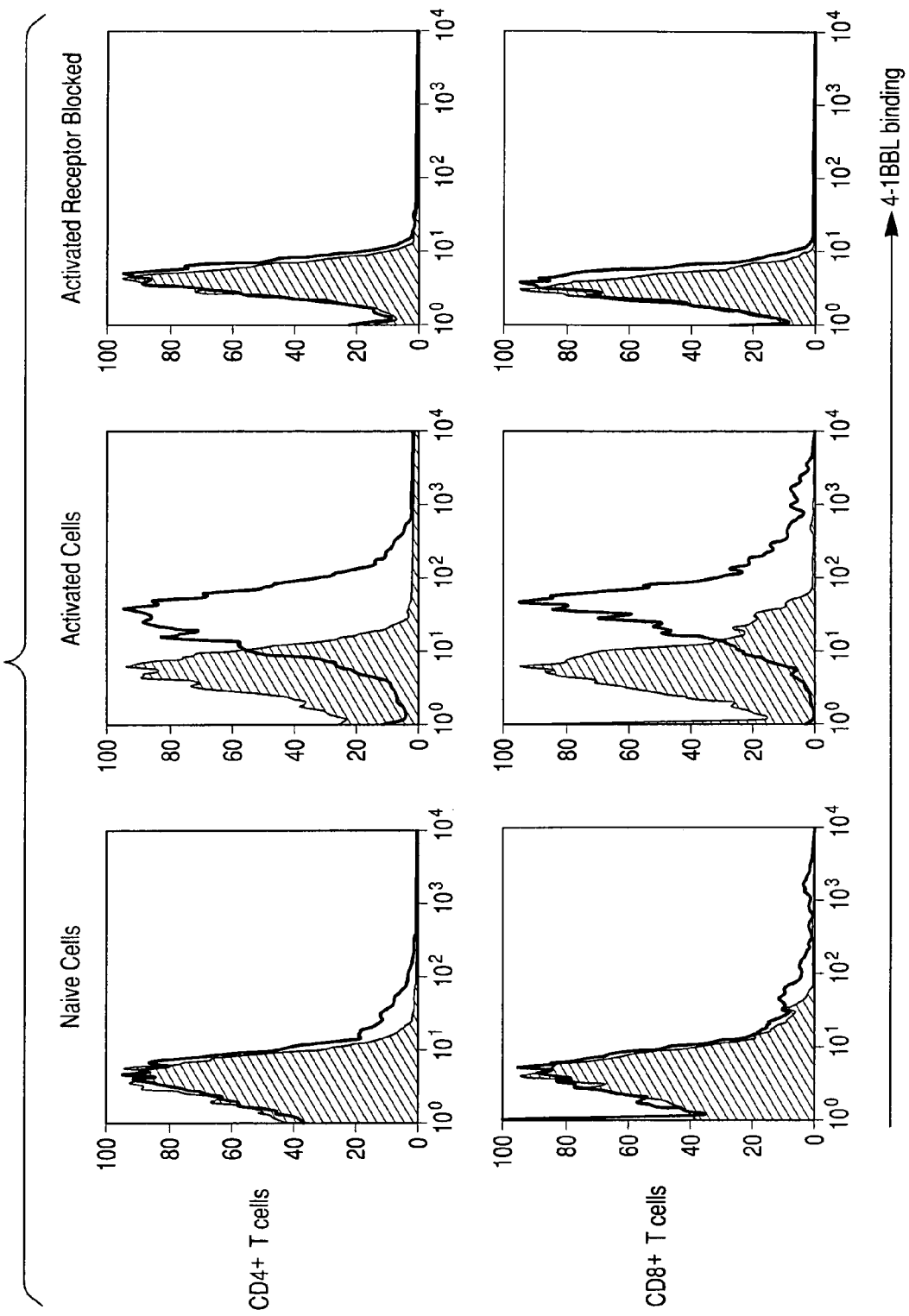

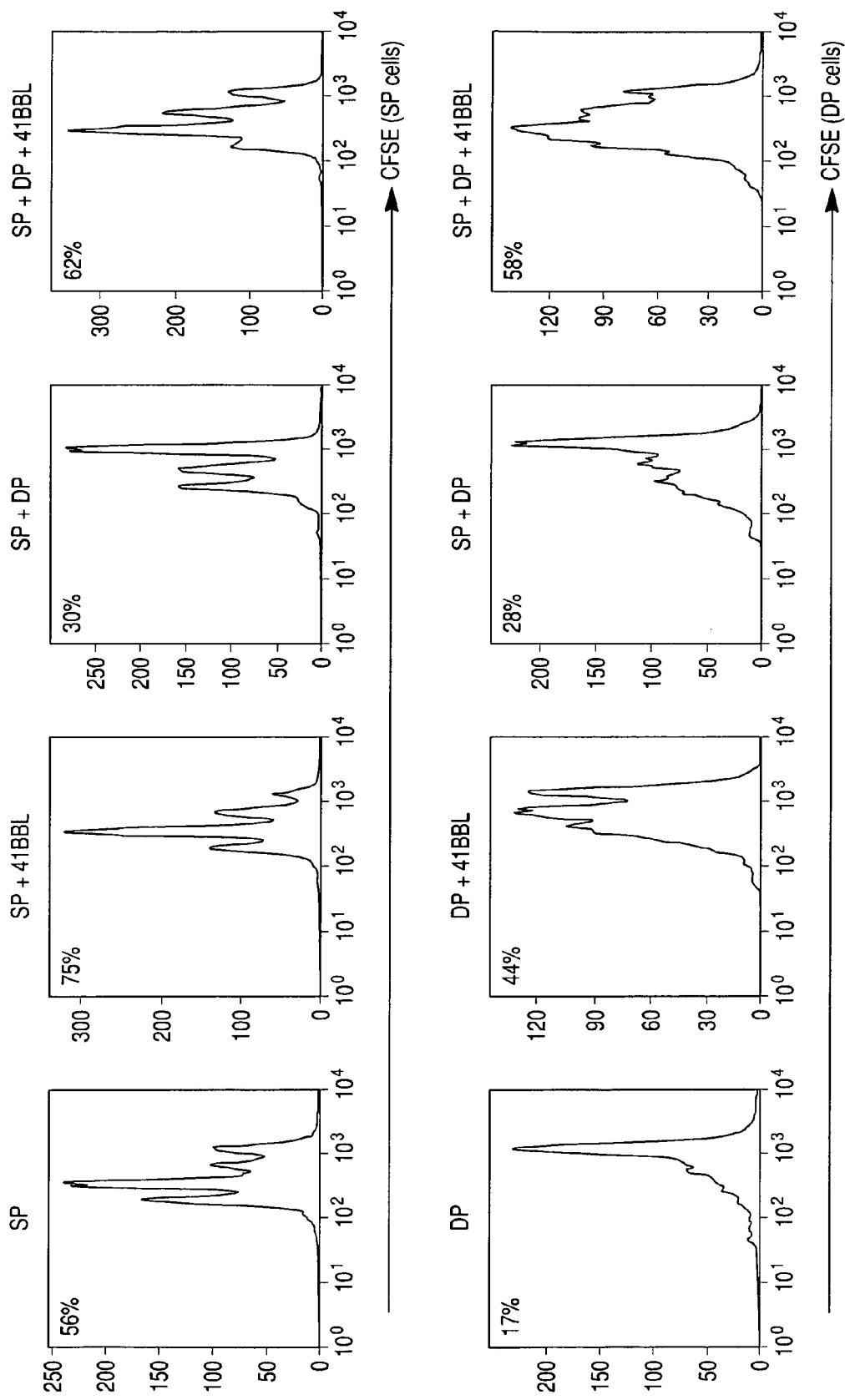

SEQUENCE LISTING

<160> NUMBER OF SEQ ID NOS: 23

<210> SEQ ID NO 1
<211> LENGTH: 1366
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 1

```
acccgtgtgt aaagccgcgt ttccaaaatg tataaaaccg agagcatctg gccaatgtgc      60
atcagttgtg gtcagcagca aaatcaagtg aatcatctca gtgcaactaa aggggggatc     120
cgatctcaat atgaagttat gcatattact ggccgtcgtg gcctttgttg gcctctcgct     180
cgggagatct catcatcacc atcaccatat caccggcacc tggtacaacc agctcggctc     240
gaccttcatc gtgaccgcgg gcgccgatgg cgccctgacc ggaacctacg agtcggccgt     300
cggcaacgcc gagagccgct acgtcctgac cggtcgttac gacagcgccc cggccaccga     360
cggcagcggc accgccctcg gttggacggt ggcctggaag aataactacc gcaacgccca     420
ctccgcgacc acgtggagcg gccagtacgt cggcggcgcc gaggcgagga tcaacaccca     480
gtggctgctg acctccggcg ccaccgaggc caacgcctgg aagtccacgc tggtcggcca     540
cgacaccttc accaaggtga agccgtccgc cgcctcaagc gaattccgca ccgagcctcg     600
gccagcgctc acaatcacca cctcgcccaa cctgggtacc cgagagaata atgcagacca     660 ggtcaccccct gtttcccaca ttggctgccc caacactaca caacagggct ctcctgtgtt     720
cgccaagcta ctggctaaaa accaagcatc gttgtgcaat acaactctga actggcacag     780
ccaagatgga gctgggagct catacctatc tcaaggtctg aggtacgaag aagacaaaaa     840
ggagttggtg gtagacagtc ccgggctcta ctacgtattt ttggaactga agctcagtcc     900
aacattcaca aacacaggcc acaaggtgca gggctgggtc tctcttgttt tgcaagcaaa     960
gcctcaggta gatgactttg acaacttggc cctgacagtg gaactgttcc cttgctccat    1020
ggagaacaag ttagtggacc gttcctggag tcaactgttg ctcctgaagg ctggccaccg    1080
cctcagtgtg ggtctgaggg cttatctgca tggagcccag gatgcataca gagactggga    1140
gctgtcttat cccaacacca ccagctttgg actcttttctt gtgaaacccg acaacccatg    1200
ggaatgagaa ctatccttct tgtgactcct agttgctaag tcctcaagct gctatgctcg    1260
agtctagagg gcccttcgaa ggtaagccta tcccctaaccc tctcctcggt ctcgattcta    1320
cgcgtaccgg tcatcatcac catcaccatt gagtttaaac ccgctg                   1366
```

<210> SEQ ID NO 2
<211> LENGTH: 307
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 2

Met Lys Leu Cys Ile Leu Leu Ala Val Val Ala Phe Val Gly Leu Ser
1               5                   10                  15

Leu Gly Arg Ser His His His His His Ile Thr Gly Thr Trp Tyr
            20                  25                  30

Asn Gln Leu Gly Ser Thr Phe Ile Val Thr Ala Gly Ala Asp Gly Ala
        35                  40                  45

Leu Thr Gly Thr Tyr Glu Ser Ala Val Gly Asn Ala Glu Ser Arg Tyr
50                  55                  60

Val Leu Thr Gly Arg Tyr Asp Ser Ala Pro Ala Thr Asp Gly Ser Gly
65                  70                  75                  80

Thr Ala Leu Gly Trp Thr Val Ala Trp Lys Asn Asn Tyr Arg Asn Ala
                85                  90                  95

His Ser Ala Thr Thr Trp Ser Gly Gln Tyr Val Gly Gly Ala Glu Ala
            100                 105                 110

Arg Ile Asn Thr Gln Trp Leu Leu Thr Ser Gly Ala Thr Glu Ala Asn
        115                 120                 125

Ala Trp Lys Ser Thr Leu Val Gly His Asp Thr Phe Thr Lys Val Lys
130                 135                 140

Pro Ser Ala Ala Ser Ser Glu Phe Gln Arg Ser His Gln Ala Asn Pro
145                 150                 155                 160

Ala Ala His Leu Thr Gly Ala Asn Ala Ser Leu Ile Gly Ile Gly Gly
                165                 170                 175

Pro Leu Leu Trp Glu Thr Arg Leu Gly Leu Ala Phe Leu Arg Gly Leu
            180                 185                 190

Thr Tyr His Asp Gly Ala Leu Val Thr Met Glu Pro Gly Tyr Tyr Tyr
        195                 200                 205

Val Tyr Ser Lys Val Gln Leu Ser Gly Val Gly Cys Pro Gln Gly Leu
210                 215                 220

Ala Asn Gly Leu Pro Ile Thr His Gly Leu Tyr Lys Arg Thr Ser Arg
225                 230                 235                 240

Tyr Pro Lys Glu Leu Glu Leu Leu Val Ser Arg Arg Ser Pro Cys Gly
                245                 250                 255

Arg Ala Asn Ser Ser Arg Val Trp Trp Asp Ser Ser Phe Leu Gly Gly
            260                 265                 270

Val Val His Leu Glu Ala Gly Glu Glu Val Val Val Arg Val Pro Gly
        275                 280                 285

Asn Arg Leu Val Arg Pro Arg Asp Gly Thr Arg Ser Tyr Phe Gly Ala
290                 295                 300

Phe Met Val
305

<210> SEQ ID NO 3
<211> LENGTH: 1268
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 3
catctccagt gcaactaaag gggggatccg atctcaatat gaagttatgc atattactgg     60
ccgtcgtggc ctttgttggc ctctcgctcg ggagatctat ccacgtgacc aaggaagtga    120
aagaagtggc aacgctgtcc tgtggtcaca atgtttctgt tgaagagctg gcacaaactc    180

-continued

```
gcatctactg gcaaaaggag aagaaaatgg tgctgactat gatgtctggg acatgaata      240 tatggcccga gtacaagaac cggaccatct ttgatatcac taataacctc tccattgtga     300
tcctggctct gcgcccatct gacgagggca catacgagtg tgttgttctg aagtatgaaa     360
aagacgcttt caagcgggaa cacctggctg aagtgacgtt atcagtcaaa gctgacttcc     420
ctacacctag tatatctgac tttgaaattc caacttctaa tattagaagg ataatttgct     480
caacctctgg aggttttcca gagcctcacc tctcctggtt ggaaaatgga gaagaattaa     540
atgccatcaa cacaacagtt cccaagatc ctgaaactga gctctatgct gttagcagca     600
aactggattt caatatgaca accaaccaca gcttcatgtg tctcatcaag tatggacatt     660
taagagtgaa tcagaccttc aactggaata caaccaagca agagagatct catcatcacc     720
atcaccatat caccggcacc tggtacaacc agctcggctc gaccttcatc gtgaccgcgg     780
gcgccgacgg cgccctgacc ggaacctacg agtcggccgt cggcaacgcc gagagccgct     840
acgtcctgac cggtcgttac gacagcgccc cggccaccga cggcagcggc accgccctcg     900
gttggacggt ggcctggaag aataactacc gcaacgccca ctccgcgacc acgtggagcg     960
gccagtacgt cggcggcgcc gaggcgagga tcaacaccca gtggctgttg acctccggcg    1020
ccaccgaggc caacgcctgg aagtccacgc tggtcggcca cgacaccttc accaaggtga    1080
agccgtccgc cgcctcaagc cgaattctgc agatatccag cacagtggcg gccgctcgag    1140
tctagagggc ccttcgaagg taagcctatc cctaaccctc tcctcggtct cgattctacg    1200
cgtaccggtc atcatcacca tcaccattga gtttaaaccc gctgatcagc ctcgactgtg    1260
ctttctaa                                                             1268
```

<210> SEQ ID NO 4
<211> LENGTH: 380
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 4

```
Ser Pro Val Gln Leu Lys Gly Gly Ser Asp Leu Asn Met Lys Leu Cys
  1               5                  10                  15

Ile Leu Leu Ala Val Val Ala Phe Val Gly Leu Ser Leu Gly Arg Ser
             20                  25                  30

Ile His Val Thr Lys Glu Val Lys Glu Val Ala Thr Leu Ser Cys Gly
         35                  40                  45

His Asn Val Ser Val Glu Glu Leu Ala Gln Thr Arg Ile Tyr Trp Gln
     50                  55                  60

Lys Glu Lys Lys Met Val Leu Thr Met Met Ser Gly Asp Met Asn Ile
 65                  70                  75                  80

Trp Pro Glu Tyr Lys Asn Arg Thr Ile Phe Asp Ile Thr Asn Asn Leu
                 85                  90                  95

Ser Ile Val Ile Leu Ala Leu Arg Pro Ser Asp Glu Gly Thr Tyr Glu
            100                 105                 110

Cys Val Val Leu Lys Tyr Glu Lys Asp Ala Phe Lys Arg Glu His Leu
        115                 120                 125

Ala Glu Val Thr Leu Ser Val Lys Ala Asp Phe Pro Thr Pro Ser Ile
    130                 135                 140

Ser Asp Phe Glu Ile Pro Thr Ser Asn Ile Arg Arg Ile Ile Cys Ser
145                 150                 155                 160
```

```
Thr Ser Gly Gly Phe Pro Glu Pro His Leu Ser Trp Leu Glu Asn Gly
            165                 170                 175
Glu Glu Leu Asn Ala Ile Asn Thr Thr Val Ser Gln Asp Pro Glu Thr
            180                 185                 190
Glu Leu Tyr Ala Val Ser Ser Lys Leu Asp Phe Asn Met Thr Thr Asn
            195                 200                 205
His Ser Phe Met Cys Leu Ile Lys Tyr Gly His Leu Arg Val Asn Gln
            210                 215                 220
Thr Phe Asn Trp Asn Thr Thr Lys Gln Glu Arg Ser His His His His
225                 230                 235                 240
His His Ile Thr Gly Thr Trp Tyr Asn Gln Leu Gly Ser Thr Phe Ile
            245                 250                 255
Val Thr Ala Gly Ala Asp Gly Ala Leu Thr Gly Thr Tyr Glu Ser Ala
            260                 265                 270
Val Gly Asn Ala Glu Ser Arg Tyr Val Leu Thr Gly Arg Tyr Asp Ser
            275                 280                 285
Ala Pro Ala Thr Asp Gly Ser Gly Thr Ala Leu Gly Trp Thr Val Ala
            290                 295                 300
Trp Lys Asn Asn Tyr Arg Asn Ala His Ser Ala Thr Thr Trp Ser Gly
305                 310                 315                 320
Gln Tyr Val Gly Gly Ala Glu Ala Arg Ile Asn Thr Gln Trp Leu Leu
            325                 330                 335
Thr Ser Gly Ala Thr Glu Ala Asn Ala Trp Lys Ser Thr Leu Val Gly
            340                 345                 350
His Asp Thr Phe Thr Lys Val Lys Pro Ser Ala Ala Ser Ser Arg Ile
            355                 360                 365
Leu Gln Ile Ser Ser Thr Val Ala Ala Arg Val
            370                 375                 380

<210> SEQ ID NO 5
<211> LENGTH: 1294
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 5
ttcatgcaac taaaggggggg atccgatctc aatatgaagt tatgcatatt actggccgtc      60
gtggcctttg ttggcctctc gctcgggaga tctcatcatc accatcacca tatcaccggc     120
acctggtaca accagctcgg ctcgaccttc atcgtgaccg cgggcgccga tggcgccctg     180
accggaacct acgagtcggc cgtcggcaac gccgagagcc gctacgtcct gaccggtcgt     240
tacgacagcg ccccggccac cgacggcagc ggcaccgccc tcggttggac ggtggcctgg     300
aagaataact accgcaacgc ccactccgcg accacgtgga cggccagta cgtcggcggc     360 gccgaggcga ggatcaacac ccagtggctg ttgacctccg gcgccaccga ggccaacgcc     420
tggaagtcca cgctggtcgg ccacgacacc ttcaccaagg tgaagccgtc cgccgcctca     480
agcgaattcc gcaccgagcc tcggccagcg ctcacaatca ccacctcgcc caacctgggt     540
acccgagaga taatgcaga ccaggtcacc cctgtttccc acattggctg ccccaacact     600
acacaacagg gctctcctgt gttcgccaag ctactggcta aaaccaagc atcgttgtgc      660 aatacaactc tgaactggca cagccaagat ggagctggga gctcatacct atctcaaggt     720
ctgaggtacg aagaagacaa aaaggagttg gtggtagaca gtcccgggct ctactacgta     780
```

-continued

```
tttttggaac tgaagctcag tccaacattc acaaacacag gccacaaggt gcagggctgg      840
gtctctcttg ttttgcaagc aaagcctcag gtagatgact ttgacaactt ggccctgaca      900
gtggaactgt tcccttgctc catggagaac aagttagtgg accgttcctg gagtcaactg      960
ttgctcctga aggctggcca ccgcctcagt gtgggtctga gggcttatct gcatggagcc     1020
caggatgcat acagagactg ggagctgtct tatcccaaca ccaccagctt tggactctttt     1080 cttgtgaaac ccgacaaccc atgggaatga aactatcct tcttgtgact cctagttgct      1140
aagtcctcaa gctgctatgc tcgagtctag agggcccttc gaaggtaagc ctatccctaa     1200
ccctctcctc ggtctcgatt ctacgcgtac cggtcatcat caccatcacc attgagttta     1260
aacccgctga tcagcctcga ctgtgccttt ctaa                                 1294
```

<210> SEQ ID NO 6
<211> LENGTH: 369
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 6

```
Phe Met Gln Leu Lys Gly Gly Ser Asp Leu Asn Met Lys Leu Cys Ile
  1               5                  10                  15

Leu Leu Ala Val Val Ala Phe Val Gly Leu Ser Leu Gly Arg Ser His
             20                  25                  30

His His His His Ile Thr Gly Thr Trp Tyr Asn Gln Leu Gly Ser
         35                  40                  45

Thr Phe Ile Val Thr Ala Gly Ala Asp Gly Ala Leu Thr Gly Thr Tyr
     50                  55                  60

Glu Ser Ala Val Gly Asn Ala Glu Ser Arg Tyr Val Leu Thr Gly Arg
 65                  70                  75                  80

Tyr Asp Ser Ala Pro Ala Thr Asp Gly Ser Gly Thr Ala Leu Gly Trp
                 85                  90                  95

Thr Val Ala Trp Lys Asn Asn Tyr Arg Asn Ala His Ser Ala Thr Thr
            100                 105                 110

Trp Ser Gly Gln Tyr Val Gly Gly Ala Glu Ala Arg Ile Asn Thr Gln
        115                 120                 125

Trp Leu Leu Thr Ser Gly Ala Thr Glu Ala Asn Ala Trp Lys Ser Thr
    130                 135                 140

Leu Val Gly His Asp Thr Phe Thr Lys Val Lys Pro Ser Ala Ala Ser
145                 150                 155                 160

Ser Glu Phe Arg Thr Glu Pro Arg Pro Ala Leu Thr Ile Thr Thr Ser
                165                 170                 175

Pro Asn Leu Gly Thr Arg Glu Asn Asn Ala Asp Gln Val Thr Pro Val
            180                 185                 190

Ser His Ile Gly Cys Pro Asn Thr Thr Gln Gln Gly Ser Pro Val Phe
        195                 200                 205

Ala Lys Leu Leu Ala Lys Asn Gln Ala Ser Leu Cys Asn Thr Thr Leu
    210                 215                 220

Asn Trp His Ser Gln Asp Gly Ala Gly Ser Ser Tyr Leu Ser Gln Gly
225                 230                 235                 240

Leu Arg Tyr Glu Glu Asp Lys Lys Glu Leu Val Val Asp Ser Pro Gly
                245                 250                 255

Leu Tyr Tyr Val Phe Leu Glu Leu Lys Leu Ser Pro Thr Phe Thr Asn
```

```
                     260                 265                 270
Thr Gly His Lys Val Gln Gly Trp Val Ser Leu Val Leu Gln Ala Lys
            275                 280                 285

Pro Gln Val Asp Asp Phe Asp Asn Leu Ala Leu Thr Val Glu Leu Phe
        290                 295                 300

Pro Cys Ser Met Glu Asn Lys Leu Val Asp Arg Ser Trp Ser Gln Leu
305                 310                 315                 320

Leu Leu Leu Lys Ala Gly His Arg Leu Ser Val Gly Leu Arg Ala Tyr
            325                 330                 335

Leu His Gly Ala Gln Asp Ala Tyr Arg Asp Trp Glu Leu Ser Tyr Pro
            340                 345                 350

Asn Thr Thr Ser Phe Gly Leu Phe Leu Val Lys Pro Asp Asn Pro Trp
            355                 360                 365

Glu

<210> SEQ ID NO 7
<211> LENGTH: 358
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 7

Met Lys Leu Cys Ile Leu Leu Ala Val Val Ala Phe Val Gly Leu Ser
  1               5                  10                  15

Leu Gly Arg Ser His His His His His His Ile Thr Gly Thr Trp Tyr
                 20                  25                  30

Asn Gln Leu Gly Ser Thr Phe Ile Val Thr Ala Gly Ala Asp Gly Ala
             35                  40                  45

Leu Thr Gly Thr Tyr Glu Ser Ala Val Gly Asn Ala Glu Ser Arg Tyr
         50                  55                  60

Val Leu Thr Gly Arg Tyr Asp Ser Ala Pro Ala Thr Asp Gly Ser Gly
 65                  70                  75                  80

Thr Ala Leu Gly Trp Thr Val Ala Trp Lys Asn Asn Tyr Arg Asn Ala
                 85                  90                  95

His Ser Ala Thr Thr Trp Ser Gly Gln Tyr Val Gly Gly Ala Glu Ala
            100                 105                 110

Arg Ile Asn Thr Gln Trp Leu Leu Thr Ser Gly Ala Thr Glu Ala Asn
        115                 120                 125

Ala Trp Lys Ser Thr Leu Val Gly His Asp Thr Phe Thr Lys Val Lys
130                 135                 140

Pro Ser Ala Ala Ser Glu Phe Leu Ala Cys Pro Trp Ala Val Ser
145                 150                 155                 160

Gly Ala Arg Ala Ser Pro Gly Ser Ala Ala Ser Pro Arg Leu Arg Glu
                165                 170                 175

Gly Pro Glu Leu Ser Pro Asp Asp Pro Ala Gly Leu Leu Asp Leu Arg
            180                 185                 190

Gln Gly Met Phe Ala Gln Leu Val Ala Gln Asn Val Leu Leu Ile Asp
        195                 200                 205

Gly Pro Leu Ser Trp Tyr Ser Asp Pro Gly Leu Ala Gly Val Ser Leu
    210                 215                 220

Thr Gly Gly Leu Ser Tyr Lys Glu Asp Thr Lys Glu Leu Val Val Ala
225                 230                 235                 240

Lys Ala Gly Val Tyr Tyr Val Phe Phe Gln Leu Glu Leu Arg Arg Val
```

```
                    245                 250                 255
Val Ala Gly Glu Gly Ser Gly Ser Val Ser Leu Ala Leu His Leu Gln
                260                 265                 270

Pro Leu Arg Ser Ala Ala Gly Ala Ala Ala Leu Ala Leu Thr Val Asp
            275                 280                 285

Leu Pro Pro Ala Ser Ser Glu Ala Arg Asn Ser Ala Phe Gly Phe Gln
        290                 295                 300

Gly Arg Leu Leu His Leu Ser Ala Gly Gln Arg Leu Gly Val His Leu
305                 310                 315                 320

His Thr Glu Ala Arg Ala Arg His Ala Trp Gln Leu Thr Gln Gly Ala
                325                 330                 335

Thr Val Leu Gly Leu Phe Arg Val Thr Pro Glu Ile Pro Ala Gly Leu
            340                 345                 350

Pro Ser Pro Arg Ser Glu
        355

<210> SEQ ID NO 8
<211> LENGTH: 1334
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 8
catctccagt gcaactaaag gggggatccg atctcaatat gaagttatgc atattactgg      60
ccgtcgtggc ctttgttggc ctctcgctcg ggagatctgc tcctctgaag attcaagctt     120
atttcaatga gactgcagac ctgccatgcc aatttgcaaa ctctcaaaac caaagcctga     180
gtgagctagt agtattttgg caggaccagg aaaacttggt tctgaatgag gtatacttag     240
gcaaagagaa atttgacagt gttcattcca agtatatggg ccgcacaagt tttgattcgg     300
acagttggac cctgagactt cacaatcttc agatcaagga caagggcttg tatcaatgta     360
tcatccatca caaaaagccc acaggaatga ttcgcatcca ccagatgaat ctgaactgt      420 cagtgcttgc taacttcagt caacctgaaa tagtaccaat ttctaatata acagaaaatg     480
tgtacataaa tttgacctgc tcatctatac acgttacccc agaacctaag aagatgagtg     540
ttttgctaag aaccaagaat tcaactatcg agtatgatgg tattatgcag aaatctcaag     600
ataatgtcac agaactgtac gacgtttcca tcagcttgtc tgtttcattc cctgatgtta     660
cgagcaatat gaccatcttc tgtattctgg aaactgacaa gacgcggctt ttatcttcac     720
ctttctctat agagcttgag gaccctcagc ctcccccaga ccacattcct agatctcatc     780
atcaccatca ccatatcacc ggcacctggt acaaccagct cggctcgacc ttcatcgtga     840
ccgcgggcgc cgacggcgcc ctgaccggaa cctacgagtc ggccgtcggc aacgccgaga     900
gccgctacgt cctgaccggt cgttacgaca gcgccccggc caccgacggc agcggcaccg     960
ccctcggttg gacggtggcc tggaagaata actaccgcaa cgcccactcc gcgaccacgt    1020
ggagcggcca gtacgtcggc ggcgccgagg cgaggatcaa cacccagtgg ctgttgacct    1080
ccggcgccac cgaggccaac gcctggaagt ccacgctggt cggccacgac accttcacca    1140
aggtgaagcc gtccgccgcc tcaagccgaa ttctgcagat atccagcaca gtggcggccg    1200
ctcgagtcta gagggccctt cgaaggtaag cctatcccta accctctcct cggtctcgat    1260
tctacgcgta ccgtcatcat caccatcac cattgagttt aaacccgctg atcagcctcg    1320
actgtgcttt ctaa                                                      1334
```

<210> SEQ ID NO 9
<211> LENGTH: 390
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 9

Met Lys Leu Cys Ile Leu Ala Val Val Ala Phe Val Gly Leu Ser
1               5                   10                  15

Leu Gly Arg Ser Ala Pro Leu Lys Ile Gln Ala Tyr Phe Asn Glu Thr
            20                  25                  30

Ala Asp Leu Pro Cys Gln Phe Ala Asn Ser Gln Asn Gln Ser Leu Ser
        35                  40                  45

Glu Leu Val Val Phe Trp Gln Asp Gln Glu Asn Leu Val Leu Asn Glu
    50                  55                  60

Val Tyr Leu Gly Lys Glu Lys Phe Asp Ser Val His Ser Lys Tyr Met
65                  70                  75                  80

Gly Arg Thr Ser Phe Asp Ser Asp Ser Trp Thr Leu Arg Leu His Asn
                85                  90                  95

Leu Gln Ile Lys Asp Lys Gly Leu Tyr Gln Cys Ile Ile His His Lys
            100                 105                 110

Lys Pro Thr Gly Met Ile Arg Ile His Gln Met Asn Ser Glu Leu Ser
        115                 120                 125

Val Leu Ala Asn Phe Ser Gln Pro Glu Ile Val Pro Ile Ser Asn Ile
    130                 135                 140

Thr Glu Asn Val Tyr Ile Asn Leu Thr Cys Ser Ser Ile His Gly Tyr
145                 150                 155                 160

Pro Glu Pro Lys Lys Met Ser Val Leu Leu Arg Thr Lys Asn Ser Thr
                165                 170                 175

Ile Glu Tyr Asp Gly Ile Met Gln Lys Ser Gln Asp Asn Val Thr Glu
            180                 185                 190

Leu Tyr Asp Val Ser Ile Ser Leu Ser Val Ser Phe Pro Asp Val Thr
        195                 200                 205

Ser Asn Met Thr Ile Phe Cys Ile Leu Glu Thr Asp Lys Thr Arg Leu
    210                 215                 220

Leu Ser Ser Pro Phe Ser Ile Glu Leu Glu Asp Pro Gln Pro Pro Pro
225                 230                 235                 240

Asp His Ile Pro Arg Ser His His His His His Ile Thr Gly Thr
                245                 250                 255

Trp Tyr Asn Gln Leu Gly Ser Thr Phe Ile Val Thr Ala Gly Ala Asp
            260                 265                 270

Gly Ala Leu Thr Gly Thr Tyr Glu Ser Ala Val Gly Asn Ala Glu Ser
        275                 280                 285

Arg Tyr Val Leu Thr Gly Arg Tyr Asp Ser Ala Pro Ala Thr Asp Gly
    290                 295                 300

Ser Gly Thr Ala Leu Gly Trp Thr Val Ala Trp Lys Asn Asn Tyr Arg
305                 310                 315                 320

Asn Ala His Ser Ala Thr Thr Trp Ser Gly Gln Tyr Val Gly Gly Ala
                325                 330                 335

Glu Ala Arg Ile Asn Thr Gln Trp Leu Leu Thr Ser Gly Ala Thr Glu
            340                 345                 350

Ala Asn Ala Trp Lys Ser Thr Leu Val Gly His Asp Thr Phe Thr Lys

```
                355                 360                 365
Val Lys Pro Ser Ala Ala Ser Ser Arg Ile Leu Gln Ile Ser Ser Thr
    370                 375                 380

Val Ala Ala Ala Arg Val
385                 390

<210> SEQ ID NO 10
<211> LENGTH: 796
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 10
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgaa ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct tttctcaaag catcatctca acactaactg gtagatctca tcatcaccat     420
caccatatca ccggcacctg gtacaaccag ctcggctcga ccttcatcgt gaccgcgggc     480
gccgacggcg ccctgaccgg aacctacgag tcggccgtcg gcaacgccga gagccgctac     540
gtcctgaccg gtcgttacga cagcgccccg gccaccgacg gcagcggcac cgccctcggt     600
tggacggtgg cctggaagaa taactaccgc aacgcccact ccgcgaccac gtggagcggc     660
cagtacgtcg gcggcgccga ggcgaggatc aacacccagt ggctgttgac ctccggcacc     720
accgaggcca acgcctggaa gtccacgctg gtcggccacg acaccttcac caaggtgaag     780
ccgtccgccg cctcaa                                                     796

<210> SEQ ID NO 11
<211> LENGTH: 265
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 11

Ala Pro Thr Ser Ser Thr Lys Lys Thr Gln Leu Gln Leu Glu His
 1                5                 10                  15

Leu Leu Leu Asp Leu Gln Met Ile Leu Asn Gly Ile Asn Asn Tyr Lys
                20                 25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Lys Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Ser Gln Ser Ile
        115                 120                 125

Ile Ser Thr Leu Thr Gly Arg Ser His His His His His His Ile Thr
130                 135                 140

Gly Thr Trp Tyr Asn Gln Leu Gly Ser Thr Phe Ile Val Thr Ala Gly
145                 150                 155                 160

Ala Asp Gly Ala Leu Thr Gly Thr Tyr Glu Ser Ala Val Gly Asn Ala
                165                 170                 175

Glu Ser Arg Tyr Val Leu Thr Gly Arg Tyr Asp Ser Ala Pro Ala Thr
            180                 185                 190

Asp Gly Ser Gly Thr Ala Leu Gly Trp Thr Val Ala Trp Lys Asn Asn
        195                 200                 205

Tyr Arg Asn Ala His Ser Ala Thr Thr Trp Ser Gly Gln Tyr Val Gly
    210                 215                 220

Gly Ala Glu Ala Arg Ile Asn Thr Gln Trp Leu Leu Thr Ser Gly Thr
225                 230                 235                 240

Thr Glu Ala Asn Ala Trp Lys Ser Thr Leu Val Gly His Asp Thr Phe
                245                 250                 255

Thr Lys Val Lys Pro Ser Ala Ala Ser
            260                 265
```

<210> SEQ ID NO 12
<211> LENGTH: 728
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 12

```
gccctggaca ccaactattg cttcagctcc acggagaaga actgctgcgt gcggcagctg      60
tacattgact ccgcaagga cctcggctgg aagtggatcc acgagcccaa gggctaccat     120
gccaacttct gcctcgggcc ctgcccctac atttggagcc tggacacgca gtacagcaag     180
gtcctggccc tgtacaacca gcataacccg ggcgcctcgg cggcgccgtg ctgcgtgccg     240
caggcgctgg agccgctgcc catcgtgtac tacgtgggcc gcaagcccaa ggtggagcag     300
ctgtccaaca tgatcgtgcg ctcctgcaag tgcagcagat ctcatcatca ccatcaccat     360
atcaccggca cctggtacaa ccagctcggc tcgaccttca tcgtgaccgc gggcgccgac     420
ggcgccctga ccggaaccta cgagtcggcc gtcggcaacg ccgagagccg ctacgtcctg     480
accggtcgtt acgacagcgc cccggccacc gacggcagcg gcaccgccct cggttggacg     540
gtggcctgga agaataacta ccgcaacgcc cactccgcga ccacgtggag cggccagtac     600
gtcggcggcg ccgaggcgag gatcaacacc cagtggctgc tgacctccgg caccaccgag     660
gccaacgcct ggaagtccac gctggtcggc cacgacacct tcaccaaggt gaagccgtcc     720
gccgcctc                                                              728
```

<210> SEQ ID NO 13
<211> LENGTH: 243
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 13

Ala Leu Asp Thr Asn Tyr Cys Phe Ser Ser Thr Glu Lys Asn Cys Cys

```
                1               5              10              15
Val Arg Gln Leu Tyr Ile Asp Phe Arg Lys Asp Leu Gly Trp Lys Trp
                    20                  25                  30

Ile His Glu Pro Lys Gly Tyr His Ala Asn Phe Cys Leu Gly Pro Cys
            35                  40                  45

Pro Tyr Ile Trp Ser Leu Asp Thr Gln Tyr Ser Lys Val Leu Ala Leu
        50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

Arg Ser His His His His His His Ile Thr Gly Thr Trp Tyr Asn Gln
        115                 120                 125

Leu Gly Ser Thr Phe Ile Val Thr Ala Gly Ala Asp Gly Ala Leu Thr
    130                 135                 140

Gly Thr Tyr Glu Ser Ala Val Gly Asn Ala Glu Ser Arg Tyr Val Leu
145                 150                 155                 160

Thr Gly Arg Tyr Asp Ser Ala Pro Ala Thr Asp Gly Ser Gly Thr Ala
                165                 170                 175

Leu Gly Trp Thr Val Ala Trp Lys Asn Asn Tyr Arg Asn Ala His Ser
            180                 185                 190

Ala Thr Thr Trp Ser Gly Gln Tyr Val Gly Gly Ala Glu Ala Arg Ile
        195                 200                 205

Asn Thr Gln Trp Leu Leu Thr Ser Gly Thr Thr Glu Ala Asn Ala Trp
    210                 215                 220

Lys Ser Thr Leu Val Gly His Asp Thr Phe Thr Lys Val Lys Pro Ser
225                 230                 235                 240

Ala Ala Ser

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Glu Asn Asp Ala Gln Ala Pro Lys Ser
1               5                   10

<210> SEQ ID NO 16
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Leu Gln Asn Asp Ala Gln Ala Pro Lys Ser
 1               5                  10

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagctgccta cagtgcccct ag                                           22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catttgccag cagtgggtag                                              20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaagtgttgg atacagccca gac                                          23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gagggtaggc tggcatctag gct                                          23

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcgaattcc gcaccgagcc tcggccagcg                                   30

<210> SEQ ID NO 22
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
ggactcgagc atagcagctt gaggacttag c                                      31

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
 1               5
```

METHODS AND COMPOSITIONS FOR EXPANDING T REGULATORY CELLS

CROSS REFERENCE TO RELATED APPLICATIONS

The present application claims the benefit of the filing date under 35 U.S.C. §119(e) of the following U.S. provisional applications: 60/748,177 (filed Dec. 8, 2005); 60/758,391 (filed Jan. 12, 2006); 60/799,642 (filed May 12, 2006); and 60/799,643 (filed May 12, 2006). Each of the foregoing applications is incorporated by reference herein in its entirety.

NIH GRANT FUNDING

The inventions disclosed herein were partly funded by grants. Therefore, to the extent that ri2hts to such inventions may accrue to the U.S. Government. the following statement, required under 37 C.F.R. 0401.14(f)(4) applies: This invention was made with government support under grants (R21 DK61333, R01 AI47864, R21 AI057903, and R21 HL080108), awarded by the National Institutes of Health. The government has certain rights in the invention.

The invention was also funded in part by Juvenile Diabetes Research Foundation (1-2001-328), American Diabetes Association (1-05-JF-56), and the Commonwealth of Kentucky Research Challenge Trust Fund.

FIELD OF THE INVENTION

The present invention relates generally to the field of immunotherapy. In particular, the invention provides methods and compositions for expanding T regulatory cells. The methods and compositions are useful, for example, in the prevention and treatment of immune-based disorders, including diabetes, and in the prevention of foreign graft rejection.

BACKGROUND OF THE INVENTION

T regulatory (Treg) cells constitute 5-10% of $CD4^+$ T cells in humans and rodents and constitutively express CD25, CD28, CTLA-4, GITR, CD62L, and 4-1BB, as well as the transcription factor FoxP3, which is involved in their development and function. IL-2 also appears to play an important role in Treg cell development and homeostatsis because animals deficient for IL-2 or components of its receptor develop T cell hyperproliferation and autoimmune diseases that can be corrected by adoptive transfer of Treg cells from naive animals. Similarly, a lack of signaling through CD28/CD80 interaction is associated with reduced number and functionality of Treg cells, suggesting that this receptor/ligand system plays an important role in the development and function of Treg cells.

Naturally arising $CD4^+CD25^+FoxP3^+$ Treg cells are a distinct cell population of cells that are positively selected on high affinity ligands in the thymus and that have been shown to play an important role in the establishment and maintenance of immunological tolerance to self antigens. Deficiencies in the development and/or function of these cells have been associated with severe autoimmunity in humans and various animal models of congenital or induced autoimmunity.

Treg cells manifest their tolerogenic effects directly via cell-to-cell contact or indirectly via soluble factors. Although the suppressive mechanisms of these cells remain to be fully elucidated, blockade of IL-2 expression in effector T cells (Teff), physical elimination of Teff cells, induction of tolerogenic dendritic cells (DCs) via CTLA-4/B7 axis, and inhibition of Teff cells via TGF-β and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

In addition to their natural role in establishing and maintaining tolerance to self-antigens, Treg cells also have been shown to play a role in peripheral tolerance to foreign antigens induced by various immunomodulatory approaches. For example, it appears that Treg cells are the common denominator of mechanisms involved in peripheral tolerance to transplantation antigens, irrespective of the immunomodulatory approach used to achieve tolerance. Treg cells also have been implicated in immune evasion mechanisms by tumors and various pathogens.

The importance of Treg cells in establishing and maintaining tolerance to self-antigens and induced tolerance to foreign antigens has generated significant interest in methods for expanding Treg cells ex vivo for therapeutic purposes. See, e.g., Tang et al., 2004, *J. Exp. Med.* 199: 1455-65; Battaglia et al., 2005, *Blood* 105: 4743-48; Earle et al., 2005, *Clin. Immunol.* 115: 3-9; Godfrey et al., 2004, *Blood* 104: 453-61; Hoffmann et al., 2004, *Blood* 104: 895-903. Inasmuch as Treg cell development occurs via signaling through T cell receptors (TCR), CD28, and IL-2, methods of expanding Treg cells have focused on providing these three signals. See, e.g., Tang et al., supra; Godfrey et al., supra; Hoffmann et al., supra. For example, Tang et al., supra, reported that Treg cells could be expanded from nonobese diabetic (NOD) animals using stimulation with beads conjugated to anti-CD3 and CD28 antibodies in the presence of high doses of IL-2 (2000 IU/ml). Adoptive transfer of expanded TCR transgenic Treg cells specific for an auto-antigen prevented diabetes in an adoptive transfer model and reversed diabetes in newly diabetic NOD mice. A limited number of other expansion protocols based on this protocol have recently been developed with some success in expanding Treg cells from rodents and humans. See, e.g, Earle et al, supra; Godfrey et al., supra. For example, Godfrey et al. reported expansion of human Treg cells using a FcγRII (CD32) expressing cell line as an alternative to beads for fixing antibodies against CD3 and CD28 on the cell surface via Fc receptors. Almost all reported ex vivo expansion protocols are based on similar schemes and require the use of high doses of IL-2 to be effective.

Despite these advances, there remains a need for methods and compositions useful for expanding Treg cells ex vivo. There is a particular need for methods that do not require the use of a solid support. There also is a particular need for methods that do not require high doses of IL-2 for efficacy. There also is a need for methods and compositions useful for expanding Treg cells in vivo.

Type 1 diabetes remains a major cause of long-term morbidity and mortality in over one percent of population worldwide. Although insulin treatment and islet transplantation are currently the most effective therapeutic regimens, both of these approaches suffer from major limitations. Thus, there remains a need for methods of inducing islet-specific auto-, allo-, and xeno-tolerance for efficient and permanent treatment of Type 1 diabetes.

As discussed above, Treg cells play an important role in the control of self-reactive responses and in the establishment and maintenance of tolerance to foreign antigens. Treg cells, therefore, present an important therapeutic target for the prevention and treatment of various autoimmune diseases, including Type 1 diabetes, rejection of solid organs, tissues, stem cells, bone marrow cells, hematopoietic stem cells, and graft-vs-host disease (GVHD). There remains a need for methods for the controlled and deliberate expansion of Treg cells in vivo for the treatment of these conditions.

SUMMARY OF THE INVENTION

The present invention generally provides methods and compositions for expanding T regulatory cells.

In accordance with one aspect, the invention provides a combination comprising (A) one or more conjugates selected from the group consisting of (a) a first conjugate comprising (i) a first conjugate member comprising a 4-1BBL polypeptide and (ii) second conjugate member comprising a first member of a binding pair; (b) a second conjugate comprising (i) a first conjugate member comprising a CD80 polypeptide and (ii) a second conjugate member comprising a first member of a binding pair; and (c) a third conjugate comprising (i) a first conjugate member comprising a TGF-β polypeptide and (ii) a second conjugate member comprising a first member of said binding pair; and (B) one or more conjugates selected from the group consisting of (a') a fourth conjugate comprising (i) a first conjugate member comprising an anti-CD3 antibody and (ii) a second conjugate member comprising a second member of the binding pair; (b') a fifth conjugate comprising (i) a first conjugate member comprising a cytokine and (ii) a second conjugate member comprising a second member of the binding pair; (c') a sixth conjugate comprising (i) a first conjugate member comprising an antigen and (ii) a second conjugate member comprising a second member of a binding pair; and (d') a seventh conjugate comprising (i) a first conjugate member comprising an anti-CD28 antibody and (ii) a second conjugate member of the binding pair.

In one specific embodiment, the first member of the binding pair comprises avidin or streptavidin (such as core streptavidin) and the second member of the binding pair comprises biotin. In another specific embodiment, at least one of the first, second or third conjugates comprises a fusion polypeptide comprising the first and second conjugate members. In a further embodiment, at least one of the first, second or third conjugates is bound to at least one of the fourth, fifth, sixth or sevenths conjugates via binding between the first and second binding pair members.

In one specific embodiment, the cytokine is selected from the group consisting of IL-2 and IL-4. In another specific embodiment, the antigen is an autoantigen. In yet another specific embodiment, the antigen is selected from the group consisting of insulin, collagen, myelin basic protein and MHC/antigen complexes. In a further specific embodiment, the antigen is selected from the group consisting of a glutamic acid decarboxylase (GAD), an islet cell autoantigen (ICA), and autoantigen NRP-A7.

In accordance with another aspect, the invention provides a method of expanding Treg cells comprising contacting a population of Treg cells with (A) one or more conjugates selected from the group consisting of (a) a first conjugate comprising (i) a first conjugate member comprising a 4-1BBL polypeptide and (ii) second conjugate member comprising a first member of a binding pair; (b) a second conjugate comprising (i) a first conjugate member comprising a CD80 polypeptide and (ii) a second conjugate member comprising a first member of a binding pair; and (c) a third conjugate comprising (i) a first conjugate member comprising a TGF-β polypeptide and (ii) a second conjugate member comprising a first member of said binding pair; and (B) one or more conjugates selected from the group consisting of (a') a fourth conjugate comprising (i) a first conjugate member comprising an anti-CD3 antibody and (ii) a second conjugate member comprising a second member of the binding pair; (b') a fifth conjugate comprising (i) a first conjugate member comprising a cytokine and (ii) a second conjugate member comprising a second member of the binding pair; (c') a sixth conjugate comprising (i) a first conjugate member comprising an antigen and (ii) a second conjugate member comprising a second member of a binding pair; and (d') a seventh conjugate comprising (i) a first conjugate member comprising an anti-CD28 antibody and (ii) a second conjugate member comprising a second member of the binding pair.

In one specific embodiment, the Treg cells comprise a receptor for at least one of the first, second or third conjugates, and at least one of the first, second or third conjugates is conjugated to the Treg cells via binding between the first conjugate member and the receptor and at least one of the fourth, fifth, sixth and seventh conjugates is conjugated to the Treg cells via binding between the first and second binding pair members. In a further embodiment, the population of Treg cells comprises Treg cells selected from the group consisting of CD4+ cells, CD25+ cells, and FoxP3+ cells. In a further embodiment, the population of Treg cells comprises a CD4+CD25+FoxP3+ cell.

In one embodiment, the method further comprises contacting the Treg cells with free IL-2. In another embodiment, the method further comprises contacting the Treg cells with free anti-CD antibody.

In one embodiment, the contacting is effected ex vivo. In a further embodiment, the method further comprises administering the expanded Treg cells to a patient.

In another embodiment, the contacting is effected in vivo by administering the conjugates to a patient. In a further embodiment, the patient is suffering from or at risk for an autoimmune disease, such as Type 1 diabetes. In another embodiment, the patient is a foreign graft patient.

In one embodiment, the method further comprises administering rapamycin to the patient. In another embodiment, the method comprises administering a composition comprising foreign cells displaying TGF-β to the patient. In one specific embodiment, the foreign cells are selected from the group consisting of splenocytes, pancreatic islet tissue, and bone marrow cells. In another specific embodiment, the foreign cells are obtained by a method comprising (a) contacting foreign cells with a bifunctional molecule comprising a first member of a binding pair and a molecule that binds to the surface of said cells to form modified foreign cells and (b) contacting the modified foreign cells with a conjugate comprising TGF-β and a second member of the binding pair to form foreign cells displaying TGF-β.

In accordance with another aspect, the invention provides a method of obtaining pulsed dendritic cells displaying TGF-β comprising (a) pulsing immature dendritic cells with an antigen, to obtained pulsed dentritic cells; (b) contacting the pulsed dendritic cells with a bifunctional molecule comprising a first member of a binding pair and a molecule that binds to the surface of the cells to form modified pulsed dendritic cells; and (c) contacting the modified pulsed dendritic cells with a conjugate comprising TGF-β and a second member of the binding pair to form pulsed dendritic cells displaying TGF-β. In one embodiment, the method further comprises driving the pulsed dendritic cells to maturity.

In one embodiment, the antigen is a diabetogenic autoantigen, such as glutamic acid decarboxylase (GAD), an islet cell autoantigen (ICA), or autoantigen NRP-A7. In another embodiment, the antigen is collagen. In another embodiment, the antigen is myelin basic protein.

In accordance with another aspect, the invention provides a population of antigen-pulsed dendritic cells displaying TGF-β, such as those made by the above-described method.

In accordance with another aspect, the invention provides a method of expanding Treg cells in a patient comprising administering a composition comprising antigen-pulsed dendritic cells displaying TGF-β, such as those made by the above-described method. In one embodiment, the method further comprises administering rapamycin to the patient.

In accordance with another aspect, the invention provides a method of obtaining hematopoietic stem cells or bone marrow cells displaying TGF-β comprising contacting the hematopoietic stem cells or bone marrow cells with a bifunctional molecule comprising a first member of a binding pair and a molecule that binds to the surface of the cells to form modified cells and (b) contacting the modified cells with a conjugate comprising TGF-β and a second member of the binding pair to form cells displaying TGF-β.

In accordance with another aspect, the invention provides a method of expanding Treg cells in a patient comprising administering a composition comprising hematopoietic stem cells displaying TGF-β or bone marrow cells displaying TGF-β, such as those made by the method described above. In one embodiment, the method further comprises administering rapamycin to the patient. In a specific embodiment, the patient is in need of tolerance induction to autoantigens, alloantigens, or xenoantigens; beta cell regeneration; prevention of foreign graft rejection; or treatment of a genetically inherited hematopoietic disorder.

In accordance with another aspect, the invention provides a population of hematopoietic stem cells or bone marrow cells displaying TGFβ, such as those made by the above-described method.

BRIEF DESCRIPTION OF THE DRAWINGS

FIGS. 1A and 1B set forth the nucleic acid sequence (SEQ ID NO:1) and encoded amino acid sequence (SEQ ID NO:2) of a fusion protein comprising core streptavidin and the extracellular domain of the murine LIGHT protein. The core streptavidin sequence is underlined.

FIGS. 2A and 2B set forth the nucleic acid sequence (SEQ ID NO:3) and encoded amino acid sequence (SEQ ID NO:4) of a fusion protein comprising the extracellular domain of human CD80 and core streptavidin. The core streptavidin sequence is underlined.

FIGS. 3A and 3B set forth the nucleic acid sequence (SEQ ID NO:5) and encoded amino acid sequence (SEQ ID NO:6) of a fusion protein comprising the extracellular domain of murine 4-1BBL and core streptavidin. The core streptavidin sequence is underlined.

FIG. 4 sets forth the amino acid sequence (SEQ ID NO:7) of a fusion protein comprising core streptavidin and the extracellular domain of human 4-1BBL. The core streptavidin sequence is underlined.

FIGS. 5A and 5B set forth the nucleic acid sequence (SEQ ID NO:8) and encoded amino acid sequence (SEQ ID NO:9) of a fusion protein comprising core streptavidin and the extracellular domain of human B7.2.

FIGS. 6A and 6B set forth the nucleic acid sequence (SEQ ID NO:10) and encoded amino acid sequence (SEQ ID NO:11) of a fusion protein comprising the active fragment of IL-2 and core streptavidin. In FIG. 6B, the IL-2 sequence is in italics, and the core streptavidin sequence is underlined.

FIGS. 7A and 7B set forth the nucleic acid sequence (SEQ ID NO:12) and encoded amino acid sequence (SEQ ID NO:13) of a fusion protein comprising core streptavidin and the mature TGFβ. In FIG. 7B, the TGF-β sequence is in italics, and the core streptavidin sequence is underlined.

FIGS. 8A-D illustrates the construction and characterization of a chimeric CSA-4-1-BBL fusion protein.
(A) Extracellular domain of mouse 4-1BBL was cloned C-terminal to core streptavidin (SA) in the PMT/BiP/V5-HisA vector.
(B) Western blot analysis of purified chimeric 4-1BBL protein (CSA-4-1BBL) under denaturing (lane 2) and native (lane 3) conditions. 4-1BBL appears as monomers of 37 kDa under denaturing and tetramers and higher structures of >150 kDa under native conditions.
(C) Binding of chimeric 4-1BBL (CSA-4-1BBL) to 4-1BB receptor. BALB/c resting or ConA activated splenocytes were incubated with CSA-4-1BBL (200 ng/1×10$^6$ cells) or equimolar amount of control CSA protein (gray filled)) and binding of 4-1BBL (black line) on CD4$^+$ and CD8$^+$ T cells was detected by flow cytometry using anti-4-1BBL Ab. Some activated cells were incubated with anti-CD 137 to block the receptor.
(D) Stimulation of T cells with CSA-4-1BBL. Sorted CD4$^+$ T cells were stimulated using anti-CD3 Ab (0.5 µg/ml) and irradiated splenocytes in the presence of soluble CSA-4-1BBL or equimolar amount of CSA at the indicated concentrations (ng/ml). Anti-CD3 Ab at 5 µg/ml was used as positive control. * $p<0.05$ compared to each other and control CSA protein. Data (mean±SD) for C and D are representative of 3 independent experiments with similar results.

FIG. 9 illustrates the long term ex vivo expansion of Treg cells in accordance with the invention, using CSA-4-1-BBL fusion protein in the presence of irradiated APC, anti-CD3 antibody, and IL-2, maintained for 10-14 days with IL-2. CD4$^+$CD25$^+$ Treg cells were sorted from the spleen and lymph nodes of naïve BALB/c mice and cultured in the presence of 0.5 µg/ml soluble anti-CD3 Ab, 1×10$^6$ irradiated syngeneic splenocytes, and 25 U/ml IL-2 with or without 1 µg/ml of soluble 4-1BBL in 6-well plates. Every 3-4 days, cells were split with fresh media supplemented with IL-2 and plated at a concentration of 1×10$^6$ cells/ml. (A) Flow cytometry analysis of CD4$^+$CD25$^+$ populations before sorting and after expansion with or without 4-1BBL. (B) Fold-expansion of naïve Treg cells ex vivo for cells cultured with (□) or without (■) 4-1BBL. Results from the last 3 independent expansions are depicted. Arrows indicate activation with anti-CD3, IL-2, 4-1BBL, and APC (secondary and tertiary activators) Cells without CSA-4-1BBL served as controls with minimal expansion.

FIGS. 13A & 13B illustrate the synergistic effect of stimulating Signals 1, 2 and 3 through TCR, 4-1BB, and IL-2R on the expansion of Treg cells in accordance with the invention.

(A) Sorted naïve DP Treg cells were cocultured for 3 days with irradiated syngeneic splenocytes in the presence of 0.5 μg/ml of CD3 Ab. Cultures were supplemented with 25 U/ml of IL-2 and/or 1 μg/ml 4-1BBL as indicated. (B) Sorted naïve DP Treg cells were cultured with or without irradiated splenocytes with or without soluble CD3 Ab, 4-1BBL, and IL-2 as indicated. * p<0.05 compared to each other and controls. Data (mean±SD) are representative of 2 independent experiments with similar results. (C) Sorted DP and SP cells were cultured for 2 days untreated or in the presence of IL-2 and/or APCs. Some of the cells were cultured with APCs and IL-2 for 2 days, washed to remove IL-2, and cultured 2 more days, and some of the cells were cultured untreated for 2 days and IL-2 was added for an additional 2 day culture. Expression of 4-1BB (black line) was analyzed using flow cytometry compared to isotype control (gray filled).

Figure 14A:
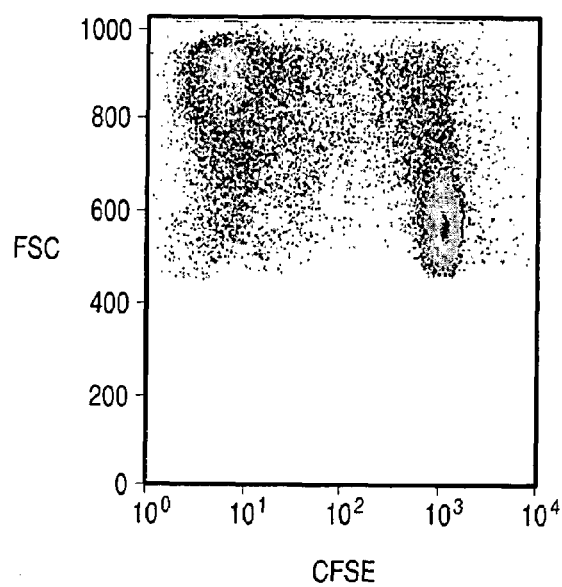
Figure 14B:
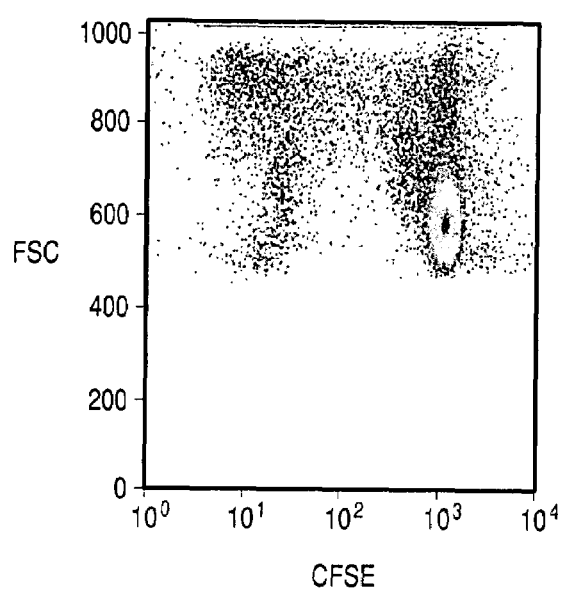

FIG. 14 shows that a TGF-β-CSA fusion protein inhibits allo responses in vitro. ACI splenocytes were labeled with CFSE and cultured with equal numbers of irradiated WF cells with (B) or without (A) TGF-β. After 5 days, cells were collected and analyzed by flow cytometry for CFSE dilution assay.

Figure 15A:
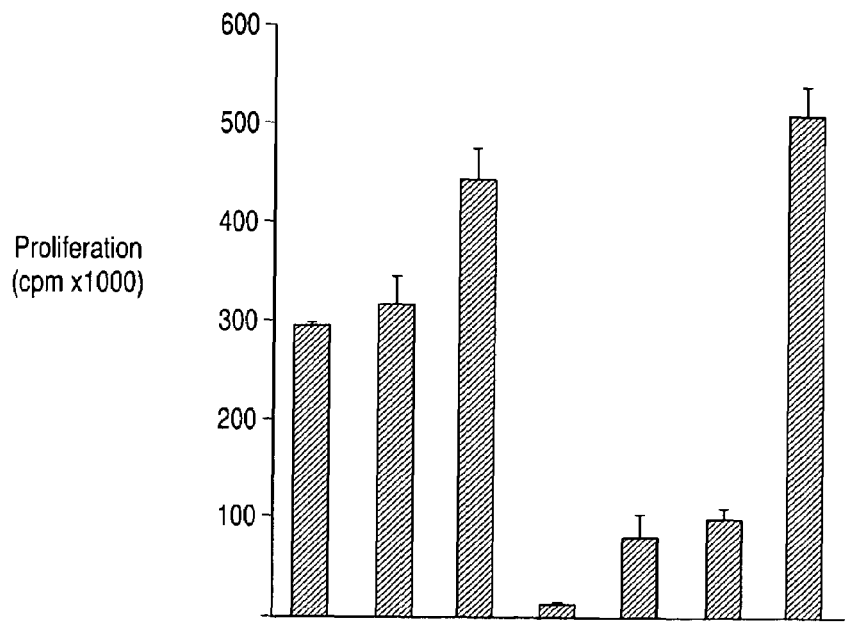

FIGS. 15A-B. Signaling via 4-1BB receptor inhibits the suppressive function of Treg cells and drives proliferation of both cells populations. (A) CD4$^+$CD25$^-$ (SP) Teff and CD4$^+$CD25$^+$ (DP) Treg cells were sorted from the spleen and peripheral lymph nodes of naïve BALB/c mice and cultured alone or at 1:1 ratio for 3 days. Cultures were supplemented with irradiated splenocytes, anti-CD3 Ab (0.5 μg/ml), and indicated concentrations (jig/ml) of 4-1BBL or equimolar control SA protein. (B) CFSE assay to assess proliferation of SP and DP cells. SP or DP cells were labeled with CFSE and used in suppression assay as described above. Percentage of dividing cells is shown for each histogram. * p<0.05 compared to each other. Data (mean±SD) are representative of 3 independent experiments with similar results.

Figure 16A:
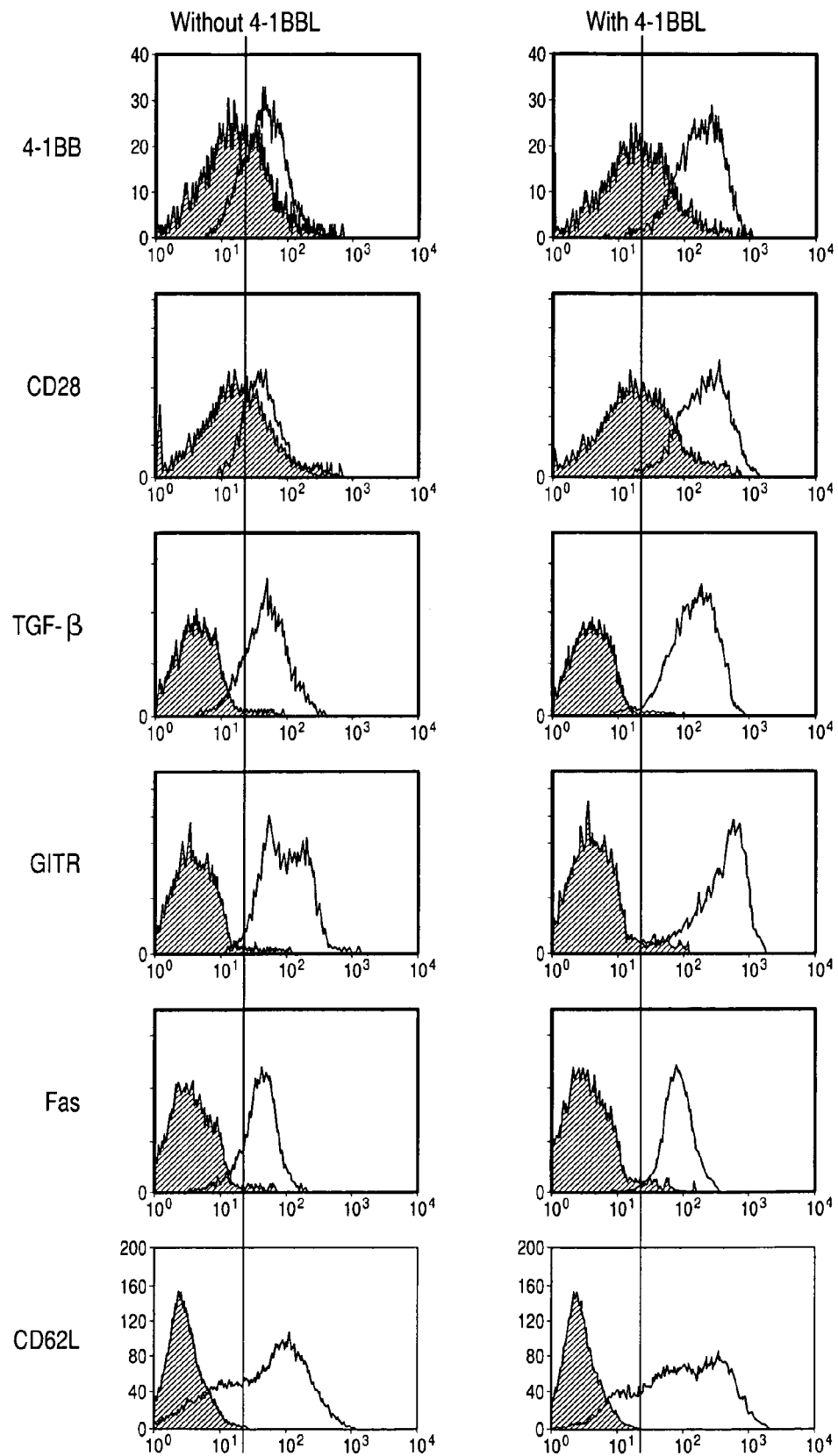
Figure 16B:
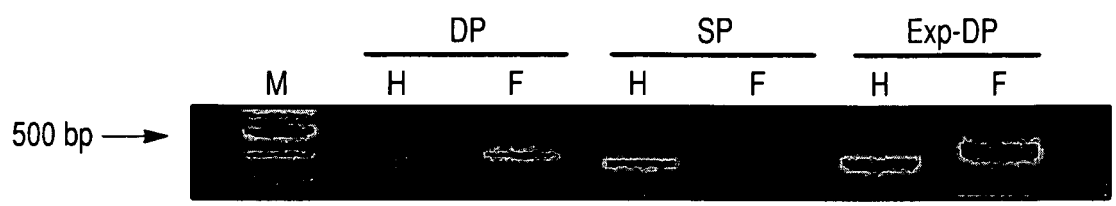
Figure 16C:
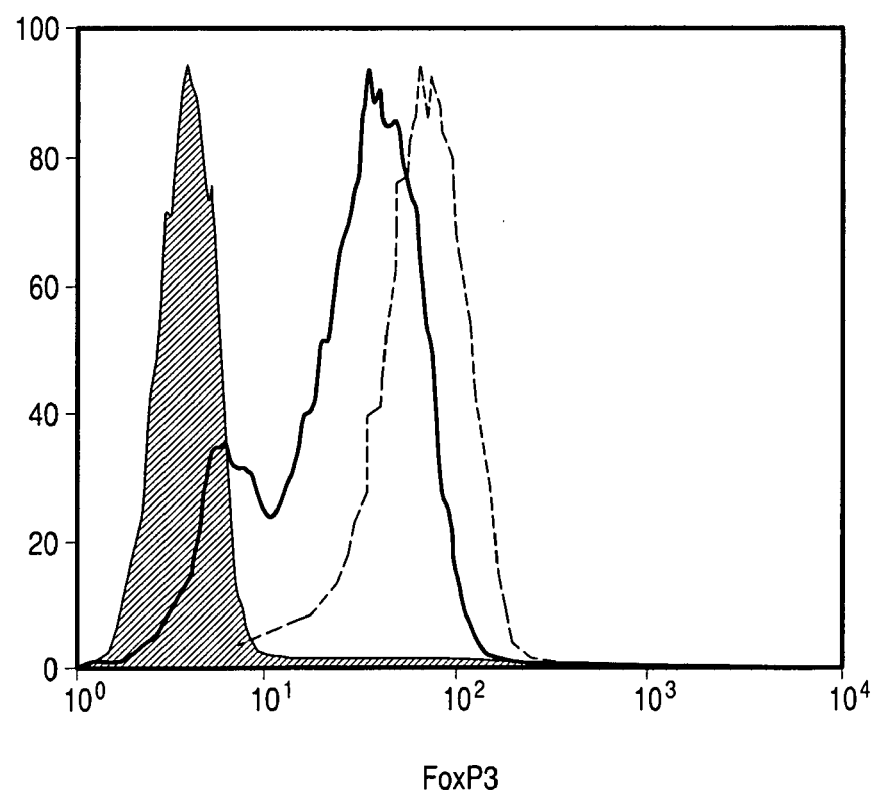

FIGS. 16A-C. Phenotypic characterization of expanded Treg cells. (A) Expression of cell surface markers important for Treg cell function were analyzed on cells expanded with or without 4-1BBL. Arbitrary vertical lines were inserted as references for the relative comparison between samples with or without 4-1BBL. (B) RT-PCR showing the expression of FoxP3 by expanded Treg cells (M, marker; H=HPRT; F=FoxP3; SP=CD4$^+$CD25$^-$; DP=CD4$^+$CD25$^+$; Exp-DP=Expanded Treg cells) (C) Intracellular staining showing the level of intracellular FoxP3 expression by Treg cells expanded with (dashed line) or without (solid line) 4-1BBL. Isotype control for FoxP3 was used as control (filled line). Data are representative of 3 independent experiments with similar results.

DETAILED DESCRIPTION

The present invention provides methods and compositions for expanding Treg cells by stimulating at least one of three signals involved in Treg cell development. Signal 1 involves TCR, and can be stimulated with antibodies, such as anti-CD3 antibodies, or with antigens that signals through TCR. Signal 2 can be mediated by several different molecules, including immune co-stimulatory molecules such as CD80 and 4-1BBL. Signal 3 is transduced via cytokines, such as IL-2, or TGFβ. The invention provides methods for expanding Treg cells that can be effected ex vivo or in vivo, and also provides compositions for carrying out such methods. In one embodiment, the methods and compositions stimulate one of these signals. In another embodiment, the methods and compositions stimulate two of these signals. In yet another embodiment, the methods and compositions stimulate three of these signals.

In an alternative aspect, the invention provides methods and compositions for expanding Treg cells using DCs pulsed with antigens and modified to display TGF-β or using hematopoietic stem cells or bone marrow cells modified to display TGFβ.

Many autoimmune diseases in humans and other animals are associated with low numbers of Treg cells and/or their lack of regulatory function. Therefore, preferential expansion of Treg cells over autoimmune Teff cells in patients with autoimmune diseases (such as Type 1 diabetes) promises substantial therapeutic benefit. Thus, the methods and compositions of the invention are useful, for example, in the prevention and treatment of immune-based disorders, including Type 1 diabetes, and in the prevention of allograft rejection.

For the purposes of the present application, the following terms have these definitions:

As used herein "a" or "an" means one or more, unless specifically indicated to mean only one.

"Administration" as used herein encompasses all suitable means of providing a substance to a patient. Common routes include oral, sublingual, transmucosal, transdermal, rectal, vaginal, subcutaneous, intramuscular, intravenous, intra-arterial, intrathecal, via catheter, via implant etc.

"Binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like.

"Patient" as used herein includes any vertebrate animal, including equine, ovine, caprine, bovine, porcine, avian, canine, feline and primate species. In one embodiment, the patient is human. A person of ordinary skill in the art will recognize that particular immune co-stimulatory molecules, signaling molecules, cell markers, cell types, infectious agents etc., discussed with reference to one species, may have corresponding analogues in different species, and that such analogues, and their use in corresponding and related species, are encompassed by the present invention.

In accordance with one aspect, invention provides conjugates comprising at least one costimulatory moiety that stimulates at least one of Signal 1, Signal 2, or Signal 3. In one specific embodiment, the conjugate comprises the costimulatory moiety and a member of a binding pair. Any moiety that stimulates one of the signals can be used in accordance with the invention, as can any binding pair members. Exemplary costimulatory moieties and binding pair members are discussed in more detail below.

Unless specified herein as "full-length," reference herein to a costimulatory moiety encompasses the full-length moiety (e.g., full-length polypeptide) as well as fragments or portions thereof that exhibit costimulatory function, including, but not limited to those fragments and portions specifically identified below. Thus, for example, reference to 4-1BBL connotes a polypeptide comprising a fragment or portion of full-length 4-1BBL that exhibits costimulatory function, such as the extracellular domain of 4-1BBL or the full-length 4-1BBL protein.

Signal 1

Exemplary costimulatory moieties for stimulating Signal 1 include antibodies against CD3 or any component of the CD3 and TCR complex, antigen/MHC complexes, and pharmacological agents such as ionomycin and phorbol myristate acetate (PMA) that signal through TCR.

Anti-CD3 antibodies useful in immunotherapeutic methods are known in the art. See, e.g., Earle et al., 2005, *Clin. Immunol.* 115: 3-9. Exemplary suitable anti-CD3 antibodies include human or murine antibodies, humanized antibodies, recombinantly produced antibodies, single chain antibodies, and CD3-binding antibody fragments. Such anti-CD3 antibodies can be obtained by methods known in the art.

As noted above, antibodies against any component of the TCR complex also can be used, such as antibodies against the TCR alpha or TCR beta chains, and antibodies against CD3 components. See, e.g., Niederberger, et al., 2005, *J. Leukoc. Biol.* 77: 830-41; Hamano et al., 2000, *J. Immunol.* 164: 6113-19. Again, any type of antibody (human, murine, recombinant, single chain, etc.) can be used.

Antigens useful as costimulatory moieties for stimulating Signal 1 include antigens associated with a target disease or condition. For example, autoantigens and insulin (particularly suitable for treating type 1 diabetes), collagen (particularly suitable for treating rheumatoid arthritis), myelin basic protein (particularly suitable for treating multiple sclerosis) and MHC (for treating and preventing foreign graft rejection). The antigens may be administered as part of a conjugate comprising a binding pair member. Optionally, the antigen is provided as part of an MHC/antigen complex. In this embodiment, the MHC and antigen can independently be foreign or syngenic. For example donor MHC and an allogenic or syngenic antigen can be used.

In accordance with one aspect of the invention, the antigen is an autoantigen. For example, the antigen may be a glutamic acid decarboxylase (GAD), an islet cell autoantigen (ICA), or the autoantigen NRP-A7 (derived from the islet-specific glucose-6-phosphatase catalytic subunit-related autoantigen and recently shown to be important in diabetes). These antigens represent a significant portion of the islet-specific autoantigen repertoire and, as such, may be effective in conferring tolerance to other potential autoantigens via epitope spreading or Treg dominated immunoregulatory mechanisms. In one particular embodiment, the autoantigen is GAD 65, ICA 512 or NRP-A7.

In accordance with one embodiment, the invention provides conjugates comprising anti-CD3 antibodies or an antigen/MHC complex as described above as the costimulatory moiety and biotin as the binding pair member. Such conjugates can be made by biotinylating anti-CD3 antibodies or antigen/MHC complexes by methods known in the art, and exemplified in the examples below. Alternatively, the antibodies or antigen can be linked or expressed as a fusion protein with a binding pair member such as core streptavidin to form an alternative conjugate useful in accordance with the present invention.

Signal 2

Exemplary costimulatory moieties for stimulating Signal 2 include members of the B7 and TNF families, including without limitation those set forth below.

| B7 and CD28 FAMILY MEMBERS | |
|---|---|
| LIGAND | RECEPTOR |
| B7.1 (CD80) | CD28, CTLA-4 (CD 152) |
| B7.2 (CD86) | CD28, CTLA-4 |
| ICOSL (B7h, B7-H2, B7RP-1, GL50, LICOS) | ICOS (AILIM) |
| PD-L1 (B7-H1) | PD-1 |
| PD-L2 (B7-DC) | PD-1 |
| B7-H3 | Unknown |
| B7-H4 (B7x; B7S1) | Unknown (BTLA?) |
| Unknown (HVEM*) | BTLA |

*it is a TNF member

| TNF FAMILY MEMBERS | |
|---|---|
| LIGAND | RECEPTOR |
| OX40L | OX40 (CD134) |
| 4-1BBL | 4-1BB (CD137) |
| CD40L (CD154) | CD40 |
| CD27L (CD70) | CD27 |
| CD30L | CD30 |
| LIGHT | HVEM, LTβR, DcR3 |
| GITRL | GITR |
| BAFF (BLyS) ** | BAFF-R, TACI, BCMA |
| APRIL ** | TACI, BCMA |

** these are B cell related

The nucleotide and/or amino acid sequences of these moieties are found in the prior art as follows:

| LIGAND (Human) | REFERENCE |
|---|---|
| B7.1 | Freeman G. J., Freedman A. S., Segil J. M., Lee G., Whitman J. F., Nadler L. M. B7, a new member of the Ig superfamily with unique expression on activated and neoplastic B cells. J. Immunol. 143:2714-2722(1989). |

-continued

| | |
|---|---|
| B7.2 | Freeman G. J., Gribben J. G., Boussiotis V. A., Ng J. W., Restivo V. A. Jr., Lombard L. A., Gray G. S., Nadler L. M. Cloning of B7-2: a CTLA-4 counter-receptor that costimulates human T cell proliferation. Science 262:909-911(1993). |
| ICOSL | Wang S., Zhu G., Chapoval A. I., Dong H., Tamada K., Ni J., Chen L. Costimulation of T cells by B7-H2, a B7-like molecule that binds ICOS. Blood 96:2808-2813(2000).<br>Yoshinaga S. K., Zhang M., Pistillo J., Horan T., Khare S. D., Miner K., Sonnenberg M., Boone T., Brankow D., Dai T., Delaney J., Han H., Hui A., Kohno T., Manoukian R., Whoriskey J. S., Coccia M. A. Characterization of a new human B7-related protein: B7RP-1 is the ligand to the co-stimulatory protein ICOS. Int. Immunol. 12:1439-1447(2000). |
| PD-L1 | Dong H., Zhu G., Tamada K., Chen L. B7-H1, a third member of the B7 family, co-stimulates T-cell proliferation and interleukin-10 secretion. Nat. Med. 5:1365-1369(1999).<br>Freeman G. J., Long A. J., Iwai Y., Bourque K., Chernova T., Nishimura H., Fitz L. J., Malenkovich N., Okazaki T., Byrne M. C., Horton H. F., Fouser L., Carter L., Ling V., Bowman M. R., Carreno B. M., Collins M., Wood C. R., Honjo T. Engagement of the PD-1 immunoinhibitory receptor by a novel B7-family member leads to negative regulation of lymphocyte activation. J. Exp. Med. 192:1027-1034(2000). |
| PD-L2 | Tseng S. -Y., Otsuji M., Gorski K., Huang X., Slansky J. E., Pai S. I., Shalabi A., Shin T., Pardoll D. M., Tsuchiya H. B7-DC, a new dendritic cell molecule with potent costimulatory properties for T cells. J. Exp. Med. 193:839-846(2001).<br>Latchman Y., Wood C. R., Chernova T., Chaudhary D., Borde M., Chernova I., Iwai Y., Long A. J., Brown J. A., Nunes R., Greenfield E. A., Bourque K., Boussiotis V. A., Carter L. L., Carreno B. M., Ma d (September 2003) to the<br>EMBL/GenBank/DDBJ databases.<br>Mingyi Sun, Sabrina Richards, Durbaka V. R. Prasad, Xoi Muoi Mai, Alexander Rudensky and Chen Dong. Characterization of Mouse and Human B7-H3 Genes. J. Immunol 168:6294-6297(2002) |
| B7-H4 (B7x; B7S1) | Zang X., Loke P., Kim J., Murphy K., Waitz R., Allison J. P. B7x: a widely expressed B7 family member that inhibits T cell activation. Proc. Natl. Acad. Sci. U.S.A. 100:10388-10392(2003).<br>Sica G. L., Choi I. -H., Zhu G., Tamada K., Wang S. -D., Tamura H., Chapoval A. I., Flies D. B., Bajorath J., Chen L. Submitted (April 2003) to the EMBL/GenBank/DDBJ databases. |

| LIGAND | REFERENCE |
|---|---|
| OX40L | Baum P. R., Gayle R. B. III, Ramsdell F., Srinivasan S., Sorensen R. A., Watson M. L., Seldin M. F., Clifford K. N., Grabstein K., Alderson M. R. Identification of OX40 ligand and preliminary characterization of its activities on OX40 receptor. Circ. Shock 44:30-34(1994).<br>Miura S., Ohtani K., Numata N., Niki M., Ohbo K., Ina Y., Gojobori T., Tanaka Y., Tozawa H., Nakamura M., Sugamura K. Molecular cloning and characterization of a novel glycoprotein, gp34, that is specifically induced by the human T-cell leukemia virus type I transactivator p40tax. Mol. Cell. Biol. 11:1313-1325(1991).<br>Godfrey W. R., Fagnoni F. F., Harara M. A., Buck D., Engleman E. G. Identification of a human OX-40 ligand, a costimulator of CD4+ T cells with homology to tumor necrosis factor. J. Exp. Med. 180:757-762(1994). |
| 4-1BBL | Alderson M. R., Smith C. A., Tough T. W., Davis-Smith T., Armitage R. J., Falk B., Roux E., Baker E., Sutherland G. R., Din W. S., Goodwin R. G. Molecular and biological characterization of human 4-1BB and its ligand. Eur. J. Immunol. 24:2219-2227(1994). |
| CD40L | Graf D., Korthaeuer U., Mages H. W., Senger G., Kroczek R. A. Cloning of TRAP, a ligand for CD40 on human T cells. Eur. J. Immunol. 22:3191-3194(1992). 11:4313-4321(1992).<br>Hollenbaugh D., Grosmaire L. S., Kullas C. D., Chalupny J. N., Braesch-Andersen S., Noelle R. J., Stamenkovic I., Ledbetter J. A., Aruffo A. The human T cell antigen gp39, a member of the TNF gene family, is a ligand for the CD40 receptor: expression of a soluble form of gp39 with B cell co-stimulatory activity. EMBO J. 11:4313-4321(1992). |
| CD27L (CD70) | Goodwin R. G., Alderson M. R., Smith C. A., Armitage R. J., Vandenbos T., Jerzy R., Tough T. W., Schoenborn M. A., David-Smith T., Hennen K., Falk B., Cosman D., Baker E., Sutherland G. R., Grabstein K. H., Farrah T., Giri J. G., Beckmann M. P. Molecular and biological characterization of a ligand for CD27 defines a new family of cytokines with homology to tumor necrosis factor. Cell 73:447-456(1993). |

-continued

| | |
|---|---|
| CD30L | Smith C. A., Gruess H.-J., Davis T., Anderson D., Farrah T., Baker E., Sutherland G. R., Brannan C. I., Copeland N. G., Jenkins N. A., Grabstein K. H., Gliniak B., McAlister I. B., Fanslow W., Alderson M., Falk B., Gimpsel S., Gillis S., Din W. S., Goodwin R. G., Armitage R. J. CD30 antigen, a marker for Hodgkin's lymphoma, is a receptor whose ligand defines an emerging family of cytokines with homology to TNF. Cell 73:1349-1360(1993). |
| LIGHT | Mauri D. N., Ebner R., Montgomery R. I., Kochel K. D., Cheung T. C., Yu G.-L., Ruben S., Murphy M., Eisenberg R. J., Cohen G. H., Spear P. G., Ware C. F. LIGHT, a new member of the TNF Superfamily, and lymphotoxin alpha are ligands for herpesvirus entry mediator. Immunity 8:21-30(1998). |
| GITRL | Gurney A. L., Marsters S. A., Huang R. M., Pitti R. M., ark D. T., Baldwin D. T., Gray A. M., Dowd A. D., Brush A. D., Heldens A. D., Schow A. D., Goddard A. D., Wood W. I., Baker K. P., Godowski P. J., Ashkenazi A. Identification of a new member of the tumer necrosis factor family and its receptor, a human ortholog of mouse GITR. Curr. Biol. 9:215-218(1999). |
| BLyS | Moore P. A., Belvedere O., Orr A., Pieri K., LaFleur D. W., Feng P., Soppet D., Charters M., Gentz R., Parmelee D., Li Y., Galperina O., Giri J., Roschke V., Nardelli B., Carrell J., Sosnovtseva S., Greenfield W., Ruben S.M., Hilbert D. M. LyS: member of the tumor necrosis factor family and B lymphocyte stimulator. Sience 285:260-263(1999). |
| APRIL | Hahne M., Kataoka T., Schroeter M., Hofmann K., Irmler M., Bodmer J.-L., Schneider P., Bornand T., Holler N., French L. E., Sordat B., Rimoldi D., Tschopp J. PRIL, a new ligand of the tumor necrosis factor family, stimulates tumor cell growth. J. Exp. Med. 188:1185-1190(1998). |

Specific examples of suitable costimulatory moieties include 4-1BBL, CD80, OX40L, and CD86, which are discussed in more detail below. It should be understood however, that any costimulatory moiety referenced above can be used in accordance with the invention.

Alternatively, antibodies to a receptor for any of these costimulatory moieties can be used. Such antibodies are known in the art, and can obtained commercially and by methods known in the art. In one embodiment of the invention, an anti-CD28 antibody is used. Anti-CD28 antibodies useful in immunotherapeutic methods are known in the art. See, e.g., Earle et al., supra. Exemplary suitable anti-CD28 antibodies include human or murine antibodies, humanized antibodies, recombinantly produced antibodies, single chain antibodies, and CD28-binding antibody fragments. Such anti-CD28 antibodies can be obtained by methods known in the art.

4-1BBL (also known as 4-BB-L, 4-BB ligand, TNFSF9, ILA ligand) is a member of the TNF receptor family and is expressed on activated antigen presenting cells (APC) including activated B cells, macrophages, and DC, 2-3 days following activation. 4-1BB (also known as CD137), which is the receptor for 4-1BBL, is expressed on the surface of activated CD4+ and CD8+ T cells, on natural killer cells (NK), monocytes, and resting DC. It also has recently been demonstrated that Treg cells constitutively express the 4-1BB receptor. See, e.g., Choi et al., 2004, J. Leukoc. Biol. 75: 785-91; McHugh et al., 2002, Immunity 16: 311-23.

4-1BBL contains 254 amino acids (26624 Da). See, e.g., Alderson et al., 1994, Eur. J. Immunol. 24(9): 2219-27. The full amino acid sequence of human 4-1BBL can be found under accession no. P41273 in the Swiss-Prot database. 4-1BBL is a type II glycoprotein with residues 1-28 forming a potential cytoplasmic domain, residues 29-49 forming a single predicted transmembrane domain, residues 50-254 forming a potential extraceulluar domain, and residues 35-41 representing a poly-Leu stretch. The nucleotide sequence encoding human 4-1BBL can be found in GenBank accession no. NM_003811.

Residues 50-254 of 4-1BBL or fragments thereof that can bind to its cognate receptor 4-1BB, can be linked or expressed as a fusion protein with a binding pair member for use in accordance with the present invention. For example, FIGS. 3A and B show the nucleotide and amino acid sequences of a CSA-murine 4-1BBL fusion protein (SEQ ID NOs 5 and 6). FIG. 4 shows the amino acid sequence of a chimeric protein comprising the extracellular domain of human 4-1BBL and core strepavidin (SEQ ID NO:7). Alternatively, 4-1BBL can be biotinylated to form a conjugate comprising 4-1BBL as the costimulatory moiety and biotin as the binding pair member.

CD80 (also known as B7.1, CD28LG, or LAB7) and CD86 (also known as B7.2, CD28LG2, LAB72) are exemplary costimulatory polypeptides, both of which bind to the CD28/CTLA4 co-receptor expressed by T cells. CD80 contains 288 amino acids (33048 Da). See Freeman et al. J. Immunol. 143 (8), 2714-2722 (1989). The full amino acid sequence of human B7.1 can be found under accession no. P33681 in the Swiss-Prot database.

B7.1 is a type I glycoprotein with residues 1-34 forming a secretion signal, residues 35-242 forming a potential extraceulluar domain, residues 243-263 forming a potential transmembrane domain, and residues 264-288 forming a potential cytoplasmic domain. Thus the mature B7.1 molecule without its secretion signal sequence represents amino acids 35-288. The nucleotide sequence in humans encoding B7.1 can be found in GenBank accession no. NM_005191.

Residues 35-242 of B7.1 or fragments thereof that can bind to its cognate receptor CD28 can be linked or expressed as a fusion protein with a binding pair member for use in accordance with the present invention. For example, FIGS. 2A and 2B set forth the nucleotide (SEQ ID NO:3) and amino acid (SEQ ID NO:4) sequences of a chimeric protein comprising the extracellular domain of human B7.1 (CD80) and core streptavidin. Alternatively, CD80 can be biotinylated to form a conjugate comprising CD80 as the costimulatory moiety and biotin as the binding pair member.

B7.2 contains 329 amino acids (37696 Da). See Freeman et al. *Science* 262 (5135), 909-911 (1993). The full amino acid sequence of human B7.2 can be found under accession no. P42081 in the Swiss-Prot database. B7.2 is a type I glycoprotein with residues 1-23 forming a secretion signal, residues 24-247 forming a potential extraceulluar domain, residues 248-268 forming a potential transmembrane domain, and residues 269-329 forming a potential cytoplasmic domain. Thus, the mature B7.2 molecule without its secretion signal sequence represents amino acids 24-329. The nucleotide sequence in humans encoding B7.2 can be found in GenBank accession no. NM_175862.

Residues 24-247 of B7.2 or fragments thereof that can bind to its cognate receptor CD28, can be linked or expressed as a fusion with a binding pair member for use in accordance with the present invention. For example, FIGS. 5A and 5B set forth the nucleotide (SEQ ID NO:8) and amino acid (SEQ ID NO:9) sequences of a chimeric protein comprising the extracellular domain of human B7.2 (CD86) and core streptavidin. Alternatively, CD86 can be biotinylated to form a conjugate comprising CD86 as the costimulatory moiety and biotin as the binding pair member.

B7.2 is usually not expressed on resting B cells and is expressed at low levels on peripheral blood monocytes (PBC) and DC. Its expression, however, is upregulated on B cells and other APC such as macrophages and DC following activation. In contrast, CD86 is constitutively expressed on PBC and DC and more rapidly upregulated on B cells. T cell receptor (TCR) interaction with the MHC/peptide complex on APC allows for simultaneous engagement of CD80/86 with CD28 on the T cell, which leads to tyrosine phosphorylation of the lipid kinase phosphotidylinositol 3-kinase, which in turn initiates a series of intracellular events that result in the induction of IL-2 gene expression, cell proliferation, and differentiation into effector function. Signal 2 may further augment a productive immune response by preventing cell death through the regulation of antiapoptotic genes, such as Bcl-xL.

OX40L is expressed by dendritic cells and other APC and binds to OX40 which is present on activated T cells. OX40L contains 183 amino acids (21950 Da). See Miura et al. *Mol. Cell. Biol.* 11:1313-1325 (1991). The full amino acid sequence of OX40L can be found under accession no. P23510 in the Swiss-Prot database. OX40L is a type II glycoprotein with a cytoplasmic domain at residues 1-23, a transmembrane domain at residues 24-50 and an extracellular domain at residues 51-183. The nucleotide sequence of OX4OL is 3510 bp, with the coding sequence being 157-708 (see Genbank accession no. NM_003326.2). Residues 51-183, or fragments thereof of OX40L that can bind to its cognate receptor OX40, can be linked or expressed as a C-terminal fusion to a binding pair member for use in accordance with the present invention.

The LIGHT polypeptide (also known as TNFS14, HVEM-L, LTg, TR2) is a TNF superfamily member which is homologous to lymphotoxin. See Mauri et al. *Immunity* 8 (1), 21-30 (1998). The full amino acid sequence of human LIGHT can be found under accession no. O43557 in the Swiss-Prot database. LIGHT contains 240 amino acids (26351 Da) and is a type II glycoprotein with residues 1-37 forming a potential cytoplasmic domain, residues 38-58 forming a single predicted transmembrane domain, and residues 59-240 forming a potential extraceulluar domain. A cleavage site involves residues 82-83. The nucleotide sequence in humans encoding LIGHT can be found in GenBank accession no. NM_172014.

Residues 59-240 of LIGHT or fragments thereof that can bind to its cognate receptor HVEM, LTβR or TR6, can be linked or expressed as a fusion with a binding pair member for use in accordance with the present invention. For example, FIGS. 1A and 1B set forth the nucleotide (SEQ ID NO:1) and amino acid sequences (SEQ ID NO:2) of a chimeric protein comprising core streptavidin and the extracellular domain of murine LIGHT. Alternatively, LIGHT can be biotinylated to form a conjugate comprising LIGHT as the costimulatory moiety and biotin as the binding pair member.

LIGHT is primarily expressed on activated T cells, NK cells, and immature dendritic cells, and serves to regulate various aspects of immune responses. LIGHT is synthesized as a membrane-bound protein, but its cell-surface expression is regulated by several posttranslational mechanisms. LIGHT is cleaved from the cell surface by matrix metalloproteinases within minutes of its expression and accumulates as a soluble molecule (isoform 1; represents approximately residues 83-240; Swiss-Prot O43557-1). The cell surface cytoplasmic segment represents isoform 2 (Swiss-Prot O43557-2). Additionally, various cell types store LIGHT in vesicles and excrete them upon activation by various physiological stimuli. Although the role of the soluble form of LIGHT is not well characterized, it may serve as a negative feedback loop to inhibit the function of the membrane-bound form by competing for HVEM and LTβR.

LIGHT interacts with three different receptors: (1) herpesvirus entry mediator (HVEM) on T cells, (2) LTβR which is expressed primarily on epithelial and stromal cells, and (3) the soluble decoy receptor 3 on various cells. These interactions endow LIGHT with different functions. Interaction with LTβR on stromal cells is associated with the production of various cytokines/chemokines, lymph node (LN) organogenesis, and restoration of secondary lymphoid structures. On the other hand, interaction of LIGHT with HVEM receptor on lymphocytes results in activation and production of cytokines, dominated by IFN-γ and GM-CSF. In this context, the LIGHT/HVEM axis appears to deliver costimulatory signals associated with the activation of Th1 type responses which play critical roles in tumor eradication.

Signal 3

Exemplary costimulatory moieties for stimulating Signal 3 include cytokines and growth factors that stimulate Signal 3, such as IL-2, IL-4, and TGF-β (including TGF-β1, TGF-β2 and TGF-β3). IL-2 and IL-4 moieties useful in immunotherapeutic methods are known in the art. See, e.g., Earle et al., 2005, supra; Thorton et al., 2004, *J. Immunol.* 172: 6519-23; Thorton et al., 2004, *Eur. J. Immunol.* 34: 366-76. In accordance with one embodiment, the mature portion of the cytokine is used.

For example, IL-2 or IL-4, or an active fragment thereof, can be linked or expressed as a fusion protein with a binding pair member for use in accordance with the present invention. For example, co-pending U.S. patent application Ser. No. 10/312,245 discloses chimeric proteins comprising the mature portion of IL-2 or IL-4 and core streptavidin that are useful in accordance with the present invention. See also FIGS. 6A and 6B, which set forth the nucleotide (SEQ ID NO:10) and amino acid (SEQ ID NO:11) sequences of the IL-2-CSA chimeric protein. Alternatively, IL-2 or IL-4 can be biotinylated by methods known in the art to provide a conjugate comprising IL-2 or IL-4 as a costimulatory moiety and biotin as a binding pair member. See, e.g., Jordan et al., 2003, *Clin. Diag. Lab. Immunol.* 10: 339-44; DeJong et al., 1995, *J. Immunol. Methods* 184: 101-12.

TGF-β1 (also known as TGF-β, TGF1, CED, DPD1, HGNC:2997, progressive diaphyseal dysplasia 1, transformning growth factor beta 1) is a multifunctional peptide that controls proliferation, differentiation, and other functions in many cell types. Many cells synthesize (and secrete) TGF-β1 and essentially all of them have specific receptors for this peptide. TGF-β1 regulates the actions of many other peptide growth factors and determines a positive or negative direction of their effects. It plays an important role in bone remodeling, and is a potent stimulator of osteoblastic bone formation, causing chemotaxis, proliferation and differentiation in committed osteoblasts.

The TGF-β1 molecule comprises 390 amino acids (44,341 Daltons). This is a precursor which is cleaved into mature TGF-β1 and latency-associated peptide (LAP). The inactive form consists of a TGF-β1 homodimer non-covalently linked to a LAP homodimer. The inactive complex can contain a latent TGF-β binding protein. The active form is a homodimer of mature β with 112 amino acids in monomer form, which is disulfide-linked. The amino acid sequence found in the SwissProt database under accession P01137 includes a 29 amino acid signal peptide at residues 1-29, a 249 amino acid latency associated peptide at residues 30-278, the 112 amino acid active TGF-β1 sequence at residues 279-390, and a 3 amino acid cell attachment site at residues 244-246. There are many variant sequences, which are encompassed by the invention. The nucleic acid sequence for the TGF-β1 gene representing nucleotides 1-2745 is found in GenBank under accession no. NM-000660, where the coding sequence is at bases 842-2017. The nucleic acid sequence was published originally in Demyk et al., 1987, *Nucl. Acids. Res.*

TGF-β1 exists as a soluble and membrane bound growth factor and is primarily involved in organogenesis and early patterning of embryos. TGF-β plays an important role in the immune system. For example, mice deficient for TGF-β1 are short lived and die due to massive infiltration of inflammatory lymphocytes and macrophages in key organs, implicating TGF-β1 in peripheral tolerance.

A series of recent studies have suggested that TGF-β is capable of mediating tolerance to self and alloantigens in various autoimmune and transplantation settings. For example, in rats, allograft tolerance using donor-specific blood transfusion was associated with high levels of TGF-β expression within the graft by infiltrating lymphocytes and a blocking antibody against TGF-β abrogated tolerance. Josien et al., 1998, *J. Clin. Invest.* 102: 1920-26. Furthermore, ectopic expression of TGF-β in heart grafts resulted in their long-term survival in allogeneic recipients. Id. Moreover, in NOD, self-tolerance established using anti-CD3 antibodies was found to be dependent on TGF-β. Belghith et al., 2003, *Nat. Med.* 9: 12-02-08, It also has been shown that transient expression of TGF-β in islet cells was effective in preventing autoimmune diabetes in NOD by expanding Treg cells. Peng et al., 2004, *Proc. Nat'l Acad. Sci. USA* 101: 4572-77. Similarly, systemic gene therapy with TGF-β1 resulted in tolerance, regeneration of beta cells, and treatment of diabetes in overtly diabetic NOD. Luo et al., 2005, *Transplantation* 79: 1091-96.

TGF-β also has been shown to play an important role in the development, homeostasis, and expansion of Treg cells. For example, mice deficient for TGF-β1 have reduced number of Treg cells in the periphery due to regulation of FoxP3 by TGFβ. Peng et al., supra. Adoptive transfer of Treg cells from TGFβ deficient mice into wild type animals resulted in their persistent existence and function, possibly due to the paracrine effect of TGF-β1. TGF-β also has been shown to play an important role in the homeostasis and function of Treg cells in NOD. See, e.g., Pop et al., 2005, *J. Exp. Med.* 201: 1333-46. NOD mice have significantly reduced absolute numbers of Treg cells as compared with disease resistant strains. This reduction results from a decline in the cell surface expression of TGF-β, which in turn results in reduced expression of FoxP3 and altered function of Treg cells that coincide with the onset of disease. See, e.g., Gregg et al., 2004, *J. Immunol.* 173: 7308-16; You et al., 2005, *Diabetes* 54: 1415-22; Pop et al., supra.

TGF-β also plays an important role in the conversion of naïve $CD4^+CD25^-$ T cells into Treg cells by inducing FoxP3 expression. TGF-β converted Treg cells can suppress T cell proliferation and prevent clonal expansion of T cells following antigenic challenge. Although very few studies have focused on the mechanisms by which TGF-β induces FoxP3 expression, this effect appears to be mediated by the down-regulation of inhibitory Smad 7 by FoxP3, thereby allowing TGF-β signaling through positive regulators Smad 3 and 4.

TGF-β, or an active fragment thereof, can be linked or expressed as a fusion protein with a binding pair member for use in accordance with the present invention. For example, co-pending U.S. patent application Ser. No. 10/312,245 discloses a chimeric protein comprising the active domain of human TGF-β and core streptavidin that is useful in accordance with the present invention. See also FIGS. 7A and 7B, which set forth the nucleotide (SEQ ID NO:12) and amino acid (SEQ ID NO:13) sequences of this chimeric protein. Alternatively, TGF-β, or an active fragment thereof, can be biotinylated by methods known in the art to provide a conjugate comprising TGF-β as a costimulatory moiety and biotin as a binding pair member. Biotinylated IL-2 also can be obtained commercially (R&D Systems).

Binding Pair Members

An exemplary binding pair is biotin and streptavidin (SA) or avidin. SA or avidin fragments which retain substanatial binding activity for biotin, such as at least 50% or more of the binding affinity of native SA or avidin, respectively, also may be used. Such fragments include "core streptavidin" ("CSA"), a truncated version of the full-length streptavidin polypeptide which may include streptavidin residues 13-138, 14-138, 13-139 or 14-139. See, e.g., Pahler et al., 1987, *J. Biol. Chem.*, 262: 13933-37. Other truncated forms of streptavidin and avidin that retain strong binding to biotin also may be used. See, e.g. Sano et al., 1995, *J Biol Chem.* 270(47): 28204-09 (describing core streptavidin variants 16-133 and 14-138) (U.S. Pat. No. 6,022,951). Mutants of streptavidin and core forms of strepavidin which retain substantial biotin binding activity or increased biotin binding activity also may be used. See, e.g., Chilcoti et al., 1995, *Proc Natl Acad Sci USA.* 92(5): 1754-58; Reznik et al., 1996, *Nat Biotechnol.* 14(8): 1007-11. For example, mutants with reduced immunogenicity, such as mutants mutated by site-directed mutagenesis to remove potential T cell epitopes or lymphocyte epitopes, can be used. See Meyer et al., 2001, *Protein Sci.* 10: 491-503. Likewise, mutants of avidin and core forms of avidin which retain substantial biotin binding activity or increased biotin binding activity also may be used. See Hiller et al., 1991, *J. Biochem.* 278: 573-85; Livnah et al., 1993, *Proc Natl Acad Sci USA* 90: 5076-80 (1993). For convenience, in the instant description, the terms "avidin" and "streptavidin" as used herein are intended to encompass biotin-binding fragments, mutants and core forms of these binding pair members. Avidin and streptavidin are available from commercial suppliers. Moreover, the nucleic acid sequences encoding streptavidin and avidin and the streptavidin and avidin amino acid sequences can be found, for example, in GenBank Accession Nos. X65082; X03591; NM_205320; X05343; Z21611; and Z21554.

As used herein "biotin" includes biotin-containing moieties that are able to bind to surfaces, such as cell surfaces (including tumor cell surfaces), such as NHS-biotin and EZ-Link™ Sulfo-NHS-LC-Biotin (Pierce). Such protein reactive forms of biotin are available commercially.

The interaction between biotin and its binding partner, avidin or streptavidin, offers several advantages in the context of the present invention. For example, biotin has an extremely high affinity for both streptavidin ($10^{13}$ $M^{-1}$) and avidin ($10^{15}$ $M^{-1}$). This embodiment also is advantageous because conjugates comprising streptavidin or avidin can be further complexed with conjugates comprising biotin. Additionally, both streptavidin and avidin are tetrameric polypeptides that each bind four molecules of biotin. Conjugates comprising streptavidin or avidin therefore have a tendency to form tetramers and higher structures, and can form complexes with multiple biotin-containing moieties.

Those skilled in the art will recognize that other mechanisms (e.g., other conjugation methods using, for example, other linking moieties or chemical or genetic cross-linking) can be used to provide higher-order structures of immune co-stimulatory molecules, such as conjugates comprising dimers, trimers, tetramers and higher-order multimers of immune co-stimulatory molecules, which also will exhibit advantageous properties. Such conjugates are included within the scope of this invention.

Conjugates

As noted above, one aspect of the invention relates to conjugates comprising at least one costimulatory moiety and a member of a binding pair. Such conjugates can be made by methods well known in the art. For example, the costimulatory moiety and binding pair member can be covalently bound to each other or conjugated to each other directly or through a linker.

In accordance with one embodiment of the invention, the conjugate is a fusion protein comprising a costimulatory polypeptide and a binding pair member, such as CSA. Fusion proteins can be made by any of a number of different methods known in the art. For example, one or more of the component polypeptides of the fusion proteins can be chemically synthesized or can be generated using well known recombinant nucleic acid technology. (As used herein, "nucleic acid" refers to RNA or DNA.) Nucleic acid sequences useful in the present invention can be obtained using, for example, the polymerase chain reaction (PCR). Various PCR methods are described, for example, in *PCR Primer: A Laboratory Manual*, Dieffenbach 7 Dveksler, Eds., Cold Spring Harbor Laboratory Press, 1995.

In accordance with one embodiment, a costimulatory polypeptide is bound via its C-terminus to the N-terminus of a binding pair member. For example, the invention includes CD80-CSA fusion proteins, TGF-β-CSA fusion proteins, IL-2-CSA fusion proteins and IL-4-CSA fusion proteins, where the CD80, TGF-β, IL-2 or IL-4 moiety is bound via its C-terminus to the N-terminus of CSA. In accordance with another embodiment, a costimulatory polypeptide is bound via its N-terminus to the C-terminus of a binding pair member. For example, the invention includes CSA4-1BBL fusion proteins, where the CSA moiety is bound via its C-terminus to the N-terminus of the costimulatory moiety. The costimulatory polypeptide may be directly bound to a binding pair member or may be bound via one or more linking moieties, such as one or more linking polypeptides.

Nucleic acids and polypeptides comprising a fragment of a costimulatory polypeptide and/or a fragment of a binding pair member are useful in the present invention, as long as the fragment retains the activity of the referent full-length polypeptide. Thus, the costimulatory fragment should retain its costimulatory activity (e.g., retain its ability to bind its receptor or ligand), and the binding member fragment should retain its ability to bind with its binding partner. Fragments can be screened for retained activity by methods that are routine in the art, including those exemplified in the examples below. Exemplary fragments of costimulatory polypeptides are set forth above.

The conjugate may include a linker such as a peptide linker between the binding pair member and the costimulatory moiety. The linker length and composition may be chosen to enhance the activity of either functional end of the moiety. The linker is generally from about 3 to about 15 amino acids long, more preferably about 5 to about 10 amino acids long, however, longer or shorter linkers may be used or the linker may be dispensed with entirely. Flexible linkers (e.g. $(Gly_4Ser)_3$(SEQ ID NO:14)) such as have been used to connect heavy and light chains of a single chain antibody may be used in this regard. See, e.g., Huston et al., 1988, *Proc. Nat. Acad. Sci. USA*, 85: 5879-5883; U.S. Pat. Nos. 5,091,513, 5,132,405, 4,956,778; 5,258,498, and 5,482,858. Other linkers are FENDAQAPKS (SEQ ID NO: 15) or LQNDAQAPKS (SEQ ID NO: 16). One or more domains of an immunoglobulin Fc region (e.g CH1, CH2 and/or CH3) also may be used as a linker.

Nucleic acids and polypeptides that are modified, varied, or mutated also are useful in the present invention, as long as they retain the activity of the referent nucleic acid or polypeptide. For example, nucleic acid and polypeptide sequences suitable for use in the present invention can have at least about 80% sequence identity (including at least 80% sequence identity) to a referent nucleic acid or polypeptide, i.e., to a nucleic acid encoding a known immune co-stimulatory polypeptide or binding pair member. In some embodiments, the nucleic acid sequence or polypeptide has at least about 85%, at least about 90%, at least about 95%, or at least about 99% sequence identity to the referent nucleic acid or polypeptide.

The invention encompasses nucleic acids with base changes that are "silent," in that they encode the same amino acid (i.e. degenerate nucleic acid sequences). The invention also encompasses nucleic acids that encode polypeptides with conservative amino acid substitutions, and such polypeptides. Conservative amino acid substitutions (for example, substituting one hydrophobic residue with a different hydrophobic residue) are well known in the art and can be effected, e.g., by point mutations and the like. The suitability of a given modified sequence, variant or mutant can be confirmed using receptor binding and/or biological screening methods that are known in the art, such as those discussed above with reference to fragments.

As used herein, "% sequence identity" is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in the aligned sequences. The total number of aligned nucleotides or amino acids refers to the minimum number of nucleotides or amino acids that are necessary to align the second sequence, and does not include alignment (e.g., forced alignment) with non-homologous sequences, such as those that may be fused at the N-terminal or C-terminal of the sequence of interest (i.e., the sequence encoding the immune co-stimulatory polypeptide or binding pair member). The total number of aligned nucleotides or amino acids may correspond to the entire coding sequence or may correspond to fragments of the full-length sequence as defined herein.

Sequences can be aligned using the using the algorithm described by Altschul et al. (1997, Nucleic Acids Res., 25:3389-3402) as incorporated into the BLAST (basic local alignment search tool) programs, available at ncbi.nlm.nih.gov on the World Wide Web. BLAST searches or alignments can be performed to determine percent sequence identity between a nucleic acid molecule (the "query sequence") and any other sequence or portion thereof using the Altschul algorithm. BLASTN can be used to align and compare the identity between nucleic acid sequences, while BLASTP can be used to align and compare the identity between amino acid sequences. When utilizing BLAST programs to calculate the percent identity between a nucleic acid sequence encoding a therapeutic polypeptide and another sequence, the default parameters of the respective programs can be used including the default for gap penalty.

Nucleic acids of the present invention may be detected by methods such as Southern or Northern blot analysis (i.e., hybridization), PCR, or in situ hybridization analysis. Polypeptides are typically detected by immunocytochemistry in transfected cell lines or by sodium dodecyl sulphate (SDS)-polyacrylamide gel electrophoresis followed by Coomassie Blue-staining or Western blot analysis using antibodies (monoclonal or polyclonal) that have specific binding affinity for the particular polypeptide. Many of these methods are discussed in detail in Sambrook et al. (1989, Molecular Cloning: A Laboratory Manual, $2^{nd}$ Ed., Cold Spring Harbor Laboratory Press, Cold Spring Harbor, N.Y.).

Nucleic acid sequences encoding a costimulatory polypeptide and binding pair member can be operably linked to one another in a construct using conventional molecular biology techniques. See, for example, *Molecular Cloning: A Laboratory Manual* (Sambrook et al., 2001, $2^{nd}$ Ed., Cold Spring Harbor Laboratory Press) or *Short Protocols in Molecular Biology* (Ausubel et al., 2002, $5^{th}$ Ed., Current Protocols). Constructs suitable for use in these methods are commercially available and used routinely in the art. Constructs can include elements necessary for expression such as promoter sequences, regulatory elements such as enhancer sequences, and response elements and/or inducible elements that modulate expression of a nucleic acid sequence. As used herein, "operably linked" refers to (i) positioning of a promoter and/or other regulatory element(s) relative to a nucleic acid sequence in such a way as to direct or regulate expression of the nucleic acid; and/or (ii) positioning the nucleic acid encoding the costimulatory polypeptide and the nucleic acid encoding the binding pair member, such that the coding sequences are "in frame," i.e., such that the construct encodes a fusion protein comprising the costimulatory polypeptide and the binding pair member.

A construct can be propagated or expressed to generate a polypeptide in a host cell by methods known in the art. As used herein, the term "host" or "host cell" is meant to include not only prokaryotes, such as *E. coli*, but also eukaryotes, such as yeast, insect, plant and animal cells. Animal cells include, for example, COS cells and HeLa cells. A host cell can be transformed or transfected with a DNA molecule (e.g., a construct) using any of the techniques commonly known to those of ordinary skill in this art, such as calcium phosphate or lithium acetate precipitation, electroporation, lipofection and particle bombardment. Host cells containing a vector of the present invention may be used for purposes such as propagating the vector, producing a nucleic acid (e.g., DNA or RNA), expressing an immune co-stimulatory polypeptide or fragments thereof, or expressing a fusion protein, as described above.

FIGS. 1A & 1B, 2A & 2B, 3A & 3B, 4, 5A & 5B, 6A & 6B and 7A & 7B show representative nucleic acid sequences (SEQ ID NOs. 1, 3, 5, 8, 10 & 12) that encode conjugates that comprise core streptavidin and a costimulatory polypeptide, and the corresponding encoded amino acid sequences (SEQ ID NOs. 2, 4, 6, 7, 9, 11 & 13).

The invention also provides conjugates comprising a costimulatory moiety and biotin as the binding pair member. Costimulatory moieties can be biotinylated by methods known in the art, and exemplified below in the examples.

For example, Biotin AviTag technology from Avidity, Inc. (Denver, Colo.) can be used to generate biotinylated proteins. The Biotin AviTag is comprised of a unique 15 amino acid peptide that is recognized by biotin ligase, BirA, that attaches biotin to a lysine residue in the peptide sequence. Schatz, 1993, *Biotechnology*, 11:1138-43. The Biotin AviTag can be genetically fused to any protein of interest, allowing the protein to be tagged with a biotin molecule.

One potential drawback to the Biotin AviTag technology is the possibility of a low degree of biotinylation, because the system biotinylates the protein at a single, unique lysine residue in the tag region. To overcome any such problem, the purified tagged proteins can be modified in vitro using purified biotin ligase. Because the biotinylation is performed enzymatically, the reaction conditions are gentler, the labeling is highly specific, and the reaction is more efficient than chemical modification of the protein using biotin derivatives. Alternatively, the methods described in Jordan, et al., supra, can be used to produce a genetically engineered biotinylated protein.

Conjugate Combinations

In accordance with one embodiment, the invention provides combinations of conjugates that are useful in methods for expanding Treg cells. In one particular embodiment, the combination comprises (a) at least one conjugate comprising (i) a moiety that stimulates at least one of Signal 1, Signal 2 or Signal 3 and (ii) a first member of a binding pair and (b) at least one conjugate comprising (i) a moiety that stimulates at least one of Signal 1, Signal 2 or Signal 3 and (ii) a second member of a binding pair. In one embodiment, the combination comprises a moiety that stimulates at least one of Signals 1, 2, or 3. In one specific embodiment, the moiety stimulates Signal 3. For example, the moiety may comprise IL-2 or IL-4. In another embodiment, the combination comprises moieties that stimulates at least two of Signals 1, 2, and 3. In one specific embodiment, the moieties stimulate Signals 2 and 3. In another specific embodiment, the moieties stimulate Signals 1 and 3. In yet another embodiment, the combination comprises moieties that stimulates each of Signals 1, 2, and 3.

In one embodiment, the combination comprises:

(A) one or more conjugates selected from the group consisting of:

(a) a first conjugate comprising (i) a first conjugate member comprising a 4-1BBL polypeptide and (ii) second conjugate member comprising a first member of a binding pair;
(b) a second conjugate comprising (i) a first conjugate member comprising a CD80 polypeptide and (ii) a second conjugate member comprising a first member of a binding pair and (c) a third conjugate comprising (i) a first conjugate member comprising a TGF-β polypeptide and (ii) a second conjugate member comprising a first member of said binding pair, and (B) one or more conjugates selected from the group consisting of:
(a') a fourth conjugate comprising (i) a first conjugate member comprising an anti-CD3 antibody and (ii) a second conjugate member comprising a second member of said binding pair; (b') a fifth conjugate comprising (i) a first conjugate member comprising a cytokine and (ii) a second conjugate member comprising a second member of said binding pair; (c') a sixth conjugate comprising (i) a first conjugate member comprising an antigen and (ii) a second conjugate member comprising a second member of a binding pair; and (d') a seventh conjugate comprising (i) a first conjugate member comprising an anti-CD28 antibody and (ii) a second conjugate member comprising a second member of said binding pair.

As discussed above, any one or more of the conjugates may comprise a fusion polypeptide comprising the first conjugate member (e.g., the costimulatory moiety) and the second conjugate member (e.g., the binding pair member). In one embodiment, the first member of the binding pair comprises avidin or streptavidin (including core streptavidin), and the second member of the binding pair comprises biotin.

The conjugates may be provided in separate compositions, or in a single composition. Each composition may further comprise a pharmaceutically acceptable carrier, excipient or diluent, as known in the art. A pharmaceutically acceptable carrier is a material that can be used as a vehicle for the composition because the material is inert or otherwise medically acceptable, as well as compatible with the active agent(s), in the context of administration. A pharmaceutically acceptable carrier can contain conventional pharmaceutical additives like diluents and preservatives.

When the combinations are provided in a single composition, at least one of the first, second or third conjugates may be bound to at least one of the fourth, fifth, sixth or seventh conjugates via binding between the first and second binding pair members.

Exemplary combinations include one or more of:
a conjugate or fusion protein comprising 4-1BBL and core stretptavidin;
a conjugate or fusion protein comprising CD80 and core stretptavidin;
a conjugate or fusion protein comprising TGF-β and core stretptavidin;
a conjugate comprising an antigen (or antigen/MHC complex) and biotin;
a conjugate comprising IL-2 and biotin,
a conjugate comprising IL-4 and biotin,
a conjugate comprising an anti-CD3 antibody and biotin, and
a conjugate comprising an anti-CD28 antibody and biotin.

Methods

The invention also provides methods of expanding Treg cells. In one embodiment, the methods involve contact Treg cells with (a) at least one conjugate comprising (i) a moiety that stimulates at least one of Signal 1, Signal 2 or Signal 3 and (ii) a first member of a binding pair and (b) at least one conjugate comprising (i) a moiety that stimulates at least one of Signal 1, Signal 2 or Signal 3 and (ii) a second member of a binding pair. In one embodiment, the method comprises contacting Treg cells with a moiety that stimulates at least one of Signals 1, 2, or 3. In one specific embodiment, the moiety stimulates Signal 3. For example, the moiety may comprise IL-2 or IL-4. In another embodiment, the method comprises contacting Treg cells with moieties that stimulates at least two of Signals 1, 2, and 3. In one specific embodiment, the moieties stimulate Signals 2 and 3. In another specific embodiment, the moieties stimulate Signals 1 and 3. In yet another embodiment, the method comprises contacting Treg cells with moieties that stimulates each of Signals 1, 2, and 3.

In accordance with one particular embodiment, the method comprises contacting a population of Treg cells with
(A) one or more conjugates selected from the group consisting of:
(a) a first conjugate comprising (i) a first conjugate member comprising a 4-1BBL polypeptide and (ii) second conjugate member comprising a first member of a binding pair; (b) a second conjugate comprising (i) a first conjugate member comprising a CD80 polypeptide and (ii) a second conjugate member comprising a first member of a binding pair; and (c) a third conjugate comprising (i) a first conjugate member comprising a TGF-β polypeptide and (ii) a second conjugate member comprising a first member of said binding pair; and
(B) one or more conjugates selected from the group consisting of:
(a') a fourth conjugate comprising (i) a first conjugate member comprising an anti-CD3 antibody and (ii) a second conjugate member comprising a second member of said binding pair; (b') a fifth conjugate comprising (i) a first conjugate member comprising a cytokine and (ii) a second conjugate member comprising a second member of said binding pair; (c') a sixth conjugate comprising (i) a first conjugate member comprising an antigen and (ii) a second conjugate member comprising a second member of a binding pair; and (d') a seventh conjugate comprising (i) a first conjugate member comprising anti-CD28 antibody and (ii) a second conjugate member comprising a second member of said binding pair.

As noted above, Treg cells have been found to express receptors for 4-1BBL, CD80, and TGF-β. Thus, in accordance with one embodiment, the Treg cells comprise a receptor for at least one of the first, second or third conjugates, whereby at least one of the first, second or third conjugates is conjugated to the Treg cells via binding between the first conjugate member and the receptor. In accordance with this embodiment, the conjugates will bind to their receptors and crosslink the receptors for Treg activation and expansion. In a further aspect of this embodiment, at least one of the fourth, fifth, sixth and seventh conjugates is conjugated to the Treg cells through the at least one first or second conjugates, via binding between the first and second binding pair members.

The population of Treg cells may comprise CD4+ cells, CD25+ cells, and FoxP3+ cells. In one specific embodiment, the population of Treg cells comprises CD4+CD25+FoxP3+ cells.

In accordance with one embodiment, the method is effected ex vivo, by contacting the Treg cells with the conjugates ex vivo. In one aspect of this embodiment, at least two conjugates are contacted with the Treg cells substantially simultaneously. For example, at least two conjugates may be provided in a single composition that is contacted with the population of Treg cells. In one specific embodiment, at least one of the first, second or third conjugates is bound to at least one of the fourth, fifth, sixth and seventh conjugates via binding between the first and second binding pair members.

In accordance with another ex vivo embodiment of the inventive method, at least two conjugates are contacted with the Treg cells sequentially. For example, at least two conjugates may be provided in separate compositions that are contacted with the population of Treg cells sequentially. In accordance with this latter embodiment, the first, second and/or third conjugates may be contacted first and permitted to bind to Treg cells via binding between 4-1BBL and/or CD80 and/ or TGF-β and its receptor on Treg cells. Then, the fourth, fifth, sixth and/or seventh conjugates may be contacted, and permitted to bind to Treg cells via binding between the first and second binding pair members.

For example, ex vivo expansion of Treg cells maybe accomplished by obtaining Treg cells from a patient and purifying them using standard techniques, such as antibodies against CD25 and CD4. The purified Treg cells are then cultured in the presence of a conjugate comprising a costimulatory moiety (such as CSA-4-1-BBL), a conjugate comprising anti-CD3 antibody (such as biotinylated anti-CD3 antibody) and IL-2 (including biotinylated IL-2). After 3 days of stimulation, the cultures are supplemented with IL-2 (with or without additional 4-1BBL) for 7 days. In one embodiment, a conjugate comprising TGF-β (such as CSA-TGF-β or biotinylated TGF-β) also is used from the beginning for a few weeks, or throughout the culture process. This cycle is repeated again for as long as the cells are kept in culture.

In accordance with another embodiment, the method for expanding Treg cells is effected in vivo by administering the conjugates to a patient. In accordance with this embodiment, the conjugates may be administered sequentially or substantially simultaneously. For example, the conjugates may be administered as separate compositions administered sequentially or substantially simultaneously, or the conjugates may be administered as a single composition.

In embodiments where the compositions are administered sequentially, the first, second and/or third conjugates may be administered first and permitted to localize to Treg cells via binding between 4-1BBL and/or CD80 and/or TGF-β and its receptor on Treg cells. Then, the fourth, fifth, sixth and/or seventh conjugates may be administered, and permitted to localize to Treg cells via binding between the first and second binding pair members.

In embodiments where the compositions are administered simultaneously in a single composition, the first, second and/or third conjugates may be bound to the fourth, fifth, sixth and/or conjugates via binding between the first and second binding pair members. In accordance with this embodiment, the conjugates may localize to Treg cells via binding between the 4-1BBL and/or CD80 and/or TGF-β components of the conjugates and their receptors on Treg cells.

The conjugates may be administered systemically or locally, such as by intravenous, peritoneal, or subcutaneous injection. In one embodiment, one or more of the conjugates are administered by different routes. For example, or one or more conjugates can be administered locally and one or more can be administered systemically.

The invention also includes embodiments where free costimulatory moieties, i.e., moieties that are not components of an above-described conjugate, are used in conjunction with the conjugates. Thus for example, Treg cells can be contacted with one or more conjugates, as described above, and also contacted with one or more free costimulatory moieties, such as exogenous IL-2, IL-4 or anti-CD3 antibody. The Treg cells can be contacted with the one or more free costimulatory moieties simultaneously with, prior to, or subsequent to being contacted with the one or more conjugates. This contacting may be effected ex vivo or in vivo, as described above.

In accordance with this embodiment, the amount of exogenous IL-2 used can be much lower than the high amounts required by prior art methodologies. For example, where prior art methods used 2000 IU/mL, we have shown that much lower amounts, including 25 IU/mL IL-2, are effective. Thus, the invention includes methods using IL-2 in amounts ranging from less than about 25 IU/mL up to at least about 1000 IU/mL, or more. For example, the invention includes methods using IL-2 at amounts less than about 25 IU/mL, about 25 IU/mL, about 50 IU/mL, about 75 IU/mL, about 100 IU/mL, about 150 IU/mL, about 200 IU/mL, about 250 IU/mL, about 300 IU/mL, about 350 IU/mL, about 400 IU/mL, about 450 IU/mL, about 500 IU/mL about 600 IU/mL, about 700 IU/mL, about 800 IU/mL, about 900 IU/mL, about 1000 IU/mL, or more.

Data discussed in the examples below suggests that stimulation of Signal 3 is important to Treg expansion. In the context of the present invention, Signal 3 can be stimulated using a conjugate comprising a moiety that stimulates Signal 3, such as IL-2, IL-4 or another cytokine. Alternatively, Signal 3 can be stimulated using a free costimulatory moiety that stimulates Signal 3, such as exogenous IL-2 or IL-4. In yet another alternative, Signal 3 can be stimulated by any other means, such as other means known in the art.

The invention also provides methods wherein Treg cells that have been expanded ex vivo in accordance with the above-described methods are administered to a patient. In accordance with this embodiment, the Treg cells may be administered by any route discussed above, such as intravenously.

Suitable patients include human or other animals in need of Treg cell expansion. For example, patients suffering from or at risk for an autoimmune disease, such as Type 1 diabetes, or patients receiving foreign graft transplants (i.e., allograft patients and xenograft patients), are target patients for Treg expansion in accordance with the invention, as are tumor patients receiving bone marrow transplantation (to prevent GVHD) and patients receiving foreign hematopoietic or other stem cells (such as patients being treated to generate mixed chimerism to treat hematopoietic genetic deficiencies or autoimmune diseases ). The invention also is useful for treating a patient suffering from or at risk for any disease arising from or associated with an expansion of pathogenic Teff cells.

In one embodiment, the method further comprises administering rapamycin to the patient. Rapamycin has a potent immunosuppressive activity and has been used extensively to prevent graft rejection in both experimental and clinical settings. Rapamycin does not interfere with the activation of T cells, but serves to prevent IL-2-mediated signaling and cell cycle arrest at the G1-S boundary, thereby leading to T-cell anergy and/or apoptosis and induction of operational tolerance. Rapamycin acts by inhibiting mTOR, a serine/threonine kinase involved in the initiation of protein synthesis and the transmission of survival signals.

Of significance in the context of the present invention is the differential effect of rapamycin on Treg versus Teff cells with respect to development, maintenance, and function. Unlike calcineurin inhibitors, such as cyclosporin and tacrolimus, rapamycin does not interfere with the activation and high expression level of FoxP3 in Treg cells. See, e.g., Baan et al., 2005, *Transplantation* 80: 110-17. Rapamycin used in vivo has been shown to induce apoptosis of $CD4^+CD8^+$ thymocytes and result in the expansion of peripheral regulatory $CD4^+CD25^+$ T cells. Tian et al., 2004, *Transplantation* 77: 183-89. In ex vivo culture, it was shown that rapamycin does not interfere with the function of human Treg cells while it does inhibit the proliferation and cytokine secretion of Teff cells and that, in contrast to Teff cells, Treg cells are resistant to rapamycin induced apoptosis. Game et al., 2005, *Am. J. Transplant.* 5: 454-64. Consistent with these studies, it also has been shown that, in the presence of rapamycin, Teff cells underwent activation-induced cell death (AICD) following in vitro activation by antigens while Treg cells were preferentially expanded and could block the rejection of allogeneic islets when adoptively transferred into a graft recipient.

Battaglia et al., 2005, *Blood* 105: 4743-48. Rapamycin also has been shown to alter the immunostimulatory function of DCs towards a more tolerogenic phenotype, which may in turn serve as a positive feedback loop for the development and expansion of Treg cells. Chiang et al., 2004, *J. Immunol.* 172: 1355-63. These reports are consistent with the prevailing believe that, unlike calcineurin inhibitors, rapamycin does not interfere with tolerance induction. Thus, rapamycin is suitable for use in methods of the present invention, where Treg expansion is desired.

In another embodiment, the method further comprises administering a composition comprising foreign cells (e.g., allogenic or xenogenic) displaying TGF-β. For example, foreign cells such as splenocytes, dendritic cells pulsed with antigens, bone marrow cells, hematopoietic stem cells, solid organs, and islet cells can be modified to display TGF-β. In one particular aspect of this embodiment, rapamycin is also administered to the patient.

In one embodiment, modified foreign cells are obtained by a method comprising (a) contacting foreign cells with a bifunctional molecule comprising a first member of a binding pair and a molecule that binds to the surface of the cells to form modified foreign cells and (b) contacting the modified foreign cells with a conjugate comprising TGF-β and a second member of the binding pair, to form foreign cells displaying TGF-β. The TGF-β may be full-length TGF-β or any active fragment thereof, as discussed above. The bifunctional molecule is designed such that the first member of the binding pair substantially retains its affinity for the second member of the binding pair after the bifunctional molecule has bound to the cell surface via the cell surface binding portion of the bifunctional molecule. When the bifunctional molecule comprises biotin, it can be localized to the cell surface by methods exemplified below or by other methods, such as those described in WO 02/02751. In one specific embodiment, the bifunctional molecule is a form of biotin that can conjugate to proteins on the surface of cells in vivo, such as NHS-Biotin, including Sulfo-NHS-LC-biotin. In embodiments where the bifunctional molecule comprises biotin, the second member of the binding pair comprises avidin or streptavidin (or any variant thereof discussed ab0ove, including core streptavidin).

The invention also provides methods for expanding Treg cells using antigen-pulsed DCs that have been modified ex vivo to display TGF-β. In accordance with this aspect of the invention, DCs are pulsed with one or more antigens, such as one or more autoantigens, and then modified ex vivo to display TGF-β as described above. In one embodiment, the DCs are pulsed with one or more diabetogenic autoantigens such as GAD, an islet cell autoantigen (ICA), or autoantigen NRP-A7. In one particular embodiment, DC are pulsed with each of GAD 65, ICA 512 and NRP-A7. Alternatively, immature DCs may be pulsed with pancreatic islet lysates. In another embodiment, DC are pulsed with collagen (for example, to treat arthritis). In another embodiment, DC are pulsed with myelin basic protein (for example, to treat multiple sclerosis).

One embodiment of a method of obtaining pulsed DC displaying TGF-β comprises (a) pulsing immature dendritic cells with an antigen, to obtained pulsed dentritic cells; (b) contacting the pulsed dendritic cells with a bifunctional molecule comprising a first member of a binding pair and a molecule that binds to the surface of the cells to form modified pulsed dendritic cells; and (c) contacting the modified pulsed dendritic cells with a conjugate comprising TGF-β and a second member of the binding pair to form pulsed dendritic cells displaying TGF-β. The TGF-β may be full-length TGF-β or any active fragment thereof, as discussed above. In one specific embodiment, the bifunctional molecule comprises Sulfo-NHS-LC-biotin. In embodiments where the bifunctional molecule comprises biotin, the second member of the binding pair comprises avidin or streptavidin (or any variant thereof discussed above, including core streptavidin).

In one embodiment, the pulsed DC are driven to maturity by methods known in the art. For example, the pulsed DC can be driven to maturity by incubation with 4-1BBL.

In accordance with this aspect of the invention, the pulsed, TGF-β-displaying DC can be administered to a patient in need of Treg expansion, such as those target patients discussed above. The DCs can be administered by any route discussed above, such as by intravenous administration. Optimum doses of DCs can be determined experimentally, as described below. Previous studies using pulsed DCs in NOD mice have shown that doses of $5 \times 10^5$ cells/animal and $2 \times 10^5$ cells/animal are effective at inducing Treg expansion.

The invention also encompasses methods where pulsed, TGF-β-displaying DCs are administered in conjunction with one or more of the costimulatory conjugates discussed above, and/or with rapamycin. Thus, for example, a patient can be administered pulsed, TGF-β-displaying DCs in conjunction with conjugates comprising 4-1BBL, CD80 and/or IL-2, or any other costimulatory moieties discussed above. Additionally or alternatively, a patient can be administered rapamycin. In accordance with these embodiments, the one or more conjugates and/or rapamycin can be administered substantially simultaneously with the DCs, or can be administered prior or subsequent to the DCs.

In one embodiment of the invention, non-specific Treg expansion is achieved using conjugates comprising 4-1-BBL and/or CD80, IL-2 and, optionally, TGF-β. In another embodiment, antigen-specific Treg expansion is achieved using conjugates comprising 4-1BBL and/or CD80 and IL-2, in conjunction with foreign pancreatic islets or organs or dendritic cells pulsed with relevant antigens and decorated with TGF-β under the cover of transient use of rapamycin.

The invention also provides methods for expanding Treg cells using hematopoietic stem cells or bone marrow cells (BMC), including foreign (e.g., allogenic or xenogenic) BMC, decorated with TGF-β, in much the same manner as described above for pulsed DC. This method is useful to establish mixed chimerism for example, for the induction of tolerance to autoantigens, alloantigens and xenoantigens, and the treatment of autoimmunity and hematopoietic genetic deficiencies. This methodology can be used alone, or in conjunction with the costimulatory conjugates described above and/or in conjunction with rapamycin, as discussed above. The use of hematopoietic stem cells or BMC will not only expand Treg cells, but also will establish mixed chimerism that will control autoimmunity and allow for the regeneration of pancreatic beta cells, leading to the prevention and/or treatment of diabetes. The use of hematopoietic stem cells or foreign BMC decorated with TGF-β in conjunction with conjugates will expand Treg cells, which in turn will lead to the prevention of rejection of stem cells or BMC and the establishment of mixed chimerism that will control both auto- and alloreactivity.

In accordance with this embodiment of the invention, hematopoietic stem cells or BMC are biotinylated and decorated with TGF-β-CSA as described above, and injected intravenously under the cover of rapamycin. This treatment can be effected in conjunction with the administration of one or more costimulatory conjugates made as described above, including CD80/IL-2 and/or 4-1BBL/IL-2 conjugates, in order to augment the tolerogenic effect. Treatment with undecorated or TGF-β-decorated hematopoietic stem cells or BMC and rapamycin will expand Treg cells, leading to the prevention of diabetes.

As discussed above, TGF-β and rapamycin may work synergistically to block the activation and expansion of autoantigen-specific Teff cells while facilitating the activation and expansion of Treg cells or their conversion from CD4$^+$CD25$^-$ T cells. The optional use of one or more costimulatory conjugates may further augment this effect.

The following examples illustrate the invention in more detail, and are not intended to limit the scope of the invention in any respect.

EXAMPLES

General Methodologies

Animals: Nonobese diabetic mice (NOB) are purchased from Jackson Laboratories (Bar Harbor, Me.) and maintained under NIH and Guidelines. BALB/c and C57BL/6 mice were purchased from the Jackson Laboratory (Bar Harbor, Me.) and maintained under SPF conditions at the University of Louisville and cared for in accordance with institutional and NIH guidelines.

Expression and purification of IL-2 and 4-1BBL, CD80, and TGF-β chimeric proteins using insect DES expression system : Stable transfectants expressing these molecules using the Drosophila DES Expression System (Invitrogen; Carlsbad, Calif.) can be established as described in Singh et al., 2003, *Cancer Res*. 63: 4067-73. Transfectants are induced for recombinant protein expression in *Drosophila* serum-free medium (Gibco; Carlsbad, CA) supplemented with 1 mM copper sulfate for 72 hrs in an incubator shaker set at 25 0C. and 105 rpm. Culture supernatant is harvested by centrifugation and subjected to large-scale purification using cobalt(II)-carboxymethylaspartate crosslinked agarose immobilized metal affinity resin (BD-Talon, BD Biosciences) or Ni-NTA metal affinity resin (Qiagen), taking advantage of the 6x-Histan (SEQ ID NO: 23) engineered into the proteins. Briefly, culture medium containing recombinant proteins is precipitated by dropwise addition of 95% ethanol to produce a final concentration of 10% ethanol. After an overnight incubation at 4° C. the precipitated proteins are redissolved in $\frac{1}{10}$ of the starting volume with binding buffer (50 mM sodium phosphate pH 7.0; 500 mM sodium chloride; 0.5% Tween-20; 1% glycerol; 5 mM 2-mercaptoethanol). The metal affinity resin is equilibrated using 5× gel bed volume of binding buffer, added to the redissolved protein solution, and incubated with end-over-end rotation for 45 minutes at room temperature. The protein bound metal affinity resin is washed 2× with 50-100 ml of wash buffer (50 mM sodium phosphate pH 7.0; 500 mM sodium chloride). Bound proteins are eluted from the metal affinity resin with 2× gel bed volume of elution buffer (50 mM sodium phosphate pH 7.0; 500 mM sodium chloride 150 mM imidazole).

Purified protein eluates are pooled and loaded into Amicon Ultra™ (Millipore; Bedford, Mass.) centrifugal filter devices with 30 kD molecular weight cut off membrane. The centrifugal filter devices are centrifuged at 3000 rpm (2000×g) at 4° C. for 15 minutes. Sterile PBS is added to the retentate and the filters centrifuged again at 3000 rpm (2000×g). The retentate containing the concentrated/desalted protein is aspirated from the centrifugal filter devices, placed in sterile cryovials, and stored in liquid nitrogen. The purity of the isolated proteins is assessed by SDS-polyacrylamide gel electrophoresis. Protein concentration is determined using the BCA protein assay according to the manufacturer's instructions (Pierce).

Expression and purification of biotinylated GAD: Pancreatic islets from NOD are harvested and immediately homogenized in 4 M guanidinium thiocyanate. Total RNA is isolated as previously described. See, e.g., Shirwan et al, 1993, *J. Immunol*. 150: 2295-304. The purified RNA is dissolved in diethylpyrocarbonate-treated water, dispensed into small aliquots, and stored at −70° C. before use. A portion of this RNA is used as a template for RT-PCR using primers specific for the coding sequence of mouse GAD. See, e.g., Lee et al., 1993, *Biochim. Biophys. Acta* 1216: 157-60. The PCR product is cloned into the TA cloning vector (Invitrogen). A functional clone is identified and used for subcloning into the pAC vectors (Avidity) for expression. After bacterial transformation and selection on ampicillin medium, several clones are subjected to mini plasmid preparation and digested with the appropriate restriction enzymes to identify positive clones. A clone with the insert is used for large plasmid preparation. Plasmids are used to transform AVB100 *E. coli*, a strain with the birA ligase gene stably integrated into the chromosome. Protein expression is induced with L-arabinose for high level of expression of GAD with the biotin tag. The expressed proteins are purified using an AviTag antibody agarose. Purified GAD is assessed for concentration, endotoxin level, and biotinylation using Western blot and alkaline phosphatase conjugated streptavidin for probing. If necessary, endotoxin is removed using Detoxi-Gel Endotoxin Removing kit from Pierce. Biotinylated GAD is aliquoted and frozen in −70° C. until use.

Immunomodulation: Conjugates comprising a costimulatory moiety and core streptavidin are bound to biotinylated IL-2 and/or biotinylated GAD proteins at 1:1 molar ratios by mixing in PBS. All conjugates and DCs are injected intravenously in PBS at the doses indicated below.

Allogeneic mixed lymphocyte reaction. Spleen and lymph node cells from naïve BALB/c mice (1×10$^5$/well) are cultured as responders in a 5 day assay with irradiated (2000 cGy) splenocytes from naïve C57BL/6 mice (1×10$^5$/well) as stimulators. Expanded Treg cells are added to the cultures at different responder to Treg ratios. Cells are pulsed with H$^3$-thymidine during the last 16 hours of the culture.

Islet transplantation. Male BALB/c mice (22-26 grs, 6-8 weeks old) are rendered diabetic by a single intravenous injection of 200 mg/kg of Streptozotocin (Biomol, Plymouth Meeting, Pa.) and diabetes is confirmed by two consecutive blood glucose readings of >300 mg/dl. One day prior to islet transplantation, 5-8×10$^6$ ex vivo expanded Treg cells are transferred into each animal by intravenous injection. Donor islets are harvested from fully mismatched C57BL/6 mice by in situ perfusion of pancreata using 0.2 mg/ml of Liberase enzyme solution (Roche). After 17 minutes of digestion at 37° C., islets are purified using Ficoll gradients and maintained overnight at 37° C. in complete media (RPMI supplemented with 10% FBS, 2 mM L-Glutamine, 100 U/ml Penicillin/Streptomycin and 50 mM 2-Mercaptoethanol). The following day islets are collected, washed with PBS and 400-600 islets are transplanted into each BALB/c graft recipient under the left kidney capsule. Control animals are transplanted with allogeneic islets but do not receive Treg cells. Transplanted animals are monitored three times weekly and rejection confirmed by two consecutive blood glucose reading of >300 mg/dl.

Islet infiltrating lymphocytes: Infiltrating lymphocytes are harvested from the islets of NOD animals by first digesting the pancreas with 0.2 mg/ml of liberase (Roche), for example as described in Yolcu et al., 2002, *Immunity* 17: 795-808. Once single islets have been obtained, they are digested as previously described, for example, in Green et al., 2002,

*Immunity* 16: 183-91, to obtain islet infiltrating lymphocytes. The latter are stained for flow cytometry analysis.

Flow cytometry: Flow cytometric analysis is performed by first titrating the primary and secondary antibodies of interest and then using the optimum concentrations in flow cytometry using standard procedures. See, e.g., Mhoyan et al., 1997, *Transplantation* 64: 1665-70. Isotype-matched antibodies serve as negative controls. Samples are run on a FACS Calibur or Vantage (Becton Dickinson; Mountain View, Calif.) and analysis is performed using FlowJo (TreeSoft) or CellqQuest (BD Biosciences) software.

Intracellular cytokine analysis using flow cytometry: The analysis of intracellular IL-2, IL-4, IL-10, and IFN-γ is performed using monoclonal antibodies specific for these cytokines (PharMingen) in flow cytometric analysis. See, e.g., Elson et al., 1995, *J. Immunol.* 154: 4294-301. Cells are fixed with 4% paraformaldehyde at 37° C. for 5 min and washed twice with PBS/1% BSA. After overnight incubation on ice in PBS-S buffer (PBS, 0.01 M HEPES, 0.1% saponin) supplemented with 0.1% BSA and 10% FCS to block nonspecific binding, cells are washed twice with PBS-S buffer and incubated for 30 min on ice with cytokine-specific antibodies. After washing twice with PBS-S buffer, they are incubated for 30 min on ice with FITC-conjugated rat antibodies against mouse IgG and analyzed by flow cytometry. Isotype matched unrelated antibodies serve as negative controls. Intracellular FoxP3 analysis is performed according to the manufacturer's protocol (eBioscience).

T cell sorting and phenotyping by flow cytometry. Spleen and lymph node cells were harvested from naïve BALB/c mice, processed into single cell suspension, and red blood cells were lyzed using ACK solution. For cell sorting, cells were stained with anti-CD4-FITC, anti-CD25-PE, and anti-CD8-APC. CD4$^+$CD25$^-$ single positive (SP) and CD4$^+$CD25$^+$ double positive (DP) T cells were sorted using a FACSVantage cell sorter (BD Bioscience, San Jose, Calif.). Sorted cells were >95% pure. Naïve and expanded Treg cells were phenotyped using Abs to CD4-APC, CD4-FITC, CD8-PE, CD8-PerCP, 4-1BBL-PE, CD25-PE, CD95-FITC, biotin-CD137, biotin-CD28, biotin-GITR, biotin-TGF-β, and FITC labeled avidin in flow cytometry. Isotype Abs with matched fluorochromes were used as controls. Intracellular FoxP3 staining was performed according to the manufacturer's protocol (eBiosciences, San Diego, Calif.).

For receptor expression assays, sorted CD4$^+$CD25$^+$ or CD4$^+$CD25$^-$ T cells were cultured in 96-well plates for 2 days alone or in the presence of IL-2 (25 U/ml), irradiated splenocytes (1×10$^5$/well), or both. After 2 days of culturing, a portion of the cells were harvested, washed twice with PBS, and divided into two separate cultures. While one culture was supplemented with IL-2, the other one maintained without IL-2. After 2 days of culturing, cells were stained with antibodies against 4-1BB or CD28 and analyzed using flow cytometry.

One group of cells were collected after 2 days after culturing with IL-2 and splenocytes, washed twice, and cultured untreated for additional 2 days. In another group of cells, IL-2 was added at day 2 and cultured 2 more days. Cells were stained with antibodies against 4-1BB or CD28 and analyzed using flow cytometry.

RT-PCR for FoxP3. Total RNA is isolated from freshly sorted CD4$^+$CD25$^-$ and CD4$^+$CD25$^+$ T cells from spleen and lymph nodes of naive BALB/c mice or expanded Treg cells using TRI Reagent. Two μg RNA is used to generate first strand cDNA and PCR amplification is performed using primers specific for FoxP3 and HPRT for 33 and 27 cycles, respectively. The primer sequences are:

|FoxP3 forward 5'-CAG CTG CCT ACA GTG CCC CTA G-3' (SEQ ID NO: 17)
FoxP3 reverse 5'-CAT TTG CCA GCA GTG GGT AG-3' (SEQ ID NO: 18)
HPRT forward 5'-GAA GTG TTG GAT ACA GCC CAG AC-3' (SEQ ID NO: 19)
HPRT reverse 5'-GAG GGT AGG CTG GCA TCT AGG CT-3' (SEQ ID NO: 20)

|FoxP3 forward 5'-CAG CTG CCT ACA GTG CCC CTA G-3'

FoxP3 reverse 5'-CAT TTG CCA GCA GTG GGT AG-3'

HPRT forward 5'-GAA GTG TTG GAT ACA GCC CAG AC-3'

HPRT reverse 5'-GAG GGT AGG CTG GCA TCT AGG CT-3'

Histopathology: Pancreata are evaluated for histological signs of autoimmunity and their ability to secrete insulin. The pancreata are removed from treated and control NOD animals at different times after the treatment. Pieces of each pancreas are fixed with 10% buffered formalin, embedded in paraffin, sectioned at 4 μM, and stained with hematoxylin and eosin (H&E) to assess general pathological changes. Immunohistochemistry for cytokines, T cells, and insulin is performed as previously described. See, e.g., Green et al., 2002, *Immunity* 16:183-91.

Preparation of DCs and pulsing with diabetogenic antigens: Immature DCs are produced in culture from bone marrow (BM) cells of NOD using GM-CSF and IL-4 for 4-5 days. Cells are pulsed with a mixture of GAD 65, ICA 512, and NRP-A7 peptides (30 μg/peptide/ml) and driven to differentiation overnight with 100 ng/ml of mouse CSA-4-1BBL conjugate or CD40L. Peptides are obtained commercially from GenScript Corporation. Cells are washed extensively and decorated with TGF-β (or core streptavidin as a control protein), following the method outlined above and detailed below. In some experiments, NOD APCs are co-incubated with various concentrations of extensively dialyzed NP40 lysates prepared from NOD islets as a source of autoantigens. After washing with PBS, a portion of the cells are analyzed in flow cytometry for the display of TGF-β on the cell surface, upregulation of class II, and CD80/CD86 costimulatory molecules before they are used for immunomodulation.

Display of TGF-β on cell surfaces: DCs are washed with ice-cold PBS and incubated at 2.5×10$^6$ cells/ml in PBS, pH 8.0, containing 5 μM EZ-Link™ Sulfo-NHS-LC-Biotin (Pierce) at room temperature for 20 min. Cells are washed extensively and incubated at 1×10$^6$ cell/ml with 50-100 ng of purified TGF-β-core streptavidin conjugate (or core streptavidin as a control) for 15 min at 4° C. After extensive washing with PBS, cells are processed for flow cytometric analysis and used for further studies, as described below.

Statistics: The effect of treatments on the prevention of Type 1 diabetes is estimated using Kaplan-Meier curves. The differences in survival between different groups is assessed using the log-rank test (generalized Savage/Mantel Cox). Procedures involving the comparison of data from groups of individual animals will first have the equality of variance examined using the F test (two groups) or Levene's test (multiple groups). When variances are not equal, log transformations are performed. When normally distributed sample means are to be compared, the Student's t test (two groups) or the Newman-Keuls test (multiple groups) is used. When the data are not normally distributed, the Mann-Whitney U test (two groups) or the Kruskal-Wallis test (multiple groups) is used. Statistical significance is defined as $p<0.05$.

EXAMPLE 1

Cloning and Expression of a CSA-4-1BBL Conjugate

Total RNA was isolated from mouse splenocytes stimulated with LPS (5 µg/ml) for 2 days using TRI Reagent (Molecular Research Center, Cincinnati, Ohio). Two microgram of this RNA was used to generate first strand cDNA, which was used as template for PCR to amplify the extracellular domain of 4-1BBL (aa 104-309) using sense (5'-ATC GAA TTC CGC ACC GAG CCT CGG CCA GCG-3'(SEO ID NO: 21)) and antisense (5'-GGA CTC GAG CAT AGC AGC TFI'G AGG ACT TAG C-3'(SEO ID NO: 22)) primers. Primers were engineered to include EcoRI and XhoI sites to facilitate the directional and in frame cloning into the DES expression vector (Invitrogen, San Diego, Calif.). The PCR products were cloned into PCR2.1TOPO vector and several positive clones were subjected to DNA sequencing. A single clone containing the accurate sequence for 4-1BBL was digested with EcoRI and XhoI and subcloned into pMT/BiPfV5-His expression vector containing a 6xHis Tag (SEO ID NO: 23) and core streptavidin (GSA) sequence, such that the extracellular domain of mouse 4-1BBL was cloned C-terminal to the biotin-binding and tetramer-forming domains of GSA. FIG. 8A. The chimeric gene was subcloned in frame with the secretion signal of *Drosophila* in a metal-inducible expression vector and the CSA-4-1BBL conjugate was expressed in S2 insect cels using the *Drosophila* DES expression system, purified using sepharose column, and tested for endotoxin using Limulus amebocyte lysate kit (Charles River).

The CSA-4-1BBL conjugate existed as tetramers and higher order structures as determined by PAGE under native conditions. The tetrameric/oligomeric structures were dissociated into ~37 kDa monomers only under denaturing conditions and fractionation by SDS-PAGE. FIG. 8B shows the Western blot analysis of purified CSA-4-1BBL under denaturing (lane 2) and native (lane 3) conditions. Under denaturing conditions, the CSA-4-1BBL appears as monomers of 37 kDa whereas under native conditions the protein appears as tetramers and higher structures of >150 kDa.

Binding of CSA-4-1-BBL to the 4-1BB receptor was assessed as follows. Splenocytes from BALB/c or C57BL/6 mice were stimulated with 5 µg/ml of ConA (Sigma-Aldrich, St. Louis, Mo.) in total mixed lymphocyte reaction (MLR) medium (DMEM supplemented with 5% FBS, 2 mM L-Glutamine, 100 U/ml Penicillin/Streptomycin, 10 mM HEPES and 100 mM MEM-sodium pyruvate) (Invitrogen, Carlsbad, Calif.), and 50 mM 2-Mercaptoethanol (SIGMA, St. Louis, Mo.)) for 48 hrs. Activated and/or resting cells were then incubated with CSA-4-1BBL conjugate (200 ng/1×$10^6$ cells) or a molar equivalent of CSA control protein (76 ng/1× $10^6$ cells) on a rotary shaker at 4° C. for 30 min. After incubation, cells were washed several times with PBS, stained with antibodies against CD4 (APC), CD8 (PerCP), 4-1BBL (PE) and SA (FITC), and analyzed by flow cytometry. Resting and CSA-incubated cells were used as negative controls.

For blocking assays, one million activated cells were also incubated with an excessive amount (50 µg/1×$10^6$ cells) of an antibody against 4-1BB (3H3, kindly provided by R. Mittler of Emery University, Ga.) for 30 min. Cells were then washed several times with PBS, and then incubated with 200 ng of the chimeric 4-1BBL (CSA-4-1BBL) for an additional 30 min. Cells were then washed with PBS and stained with antibodies against CD4-APC, CD8-PerCP, 4-1BBL-PE and CSA-FITC, and analyzed by flow cytometry. Resting and CSA-incubated cells were used as negative controls.

Resting or ConA activated splenocytes from BALB/c mice were incubated with 4-1BBL (200 ng/1×$10^6$ cells) or control CSA protein (76 ng/1×$10^6$ cells) at 4° C. for 30 min. Binding of 4-1BBL (black line) on $CD4^+$ and $CD8^+$ T cells was detected using antibody against mouse 4-1BBL. Cells incubated with CSA protein were used as control (gray filled). As shown in FIG. 8C, CSA-4-1BBL bound to activated $CD8^+$ and $CD4^+$ T cells expressing the 4-1BB receptor. This binding was specific to 4-1BB since naïve T cells lacking the receptor scored negative, And moreover, blocking the receptor first with an antibody against 4-1BB resulted in loss of binding (FIG. 8C, right panels).

To test whether the 4-1BBL was functional, total $CD4^+$ T cells purified from the spleen and lymph nodes of naïve BALB/c were stimulated for 4 days with a suboptimal concentration of anti-CD3 antibody (0.5 µg/ml) in the presence of varying concentrations (shown in ng/ml in FIG. 8D) of soluble CSA-4-1BBL conjugate or control CSA protein. FIG. 8D. Costimulation with the CSA-4-1BBL conjugate generated a vigorous proliferative response in $CD4^+$ T cells that was concentration dependent and statistically significant ($p<0.05$). The proliferative response was 4-1BBL-dependent since control CSA protein used at equimolar levels did not measurably add to the response achieved by the suboptimal dose of anti-CD3 antibody. Taken together, these results demonstrate that the CSA-4-1BBL conjugate has structural features of the core streptavidin as it forms tetramers and oligomers, binds to 4-1BB on activated T cells, and serves as a potent activator of T cells under suboptimal anti-CD3 antibody stimulation.

EXAMPLE 2

Figure 9A:
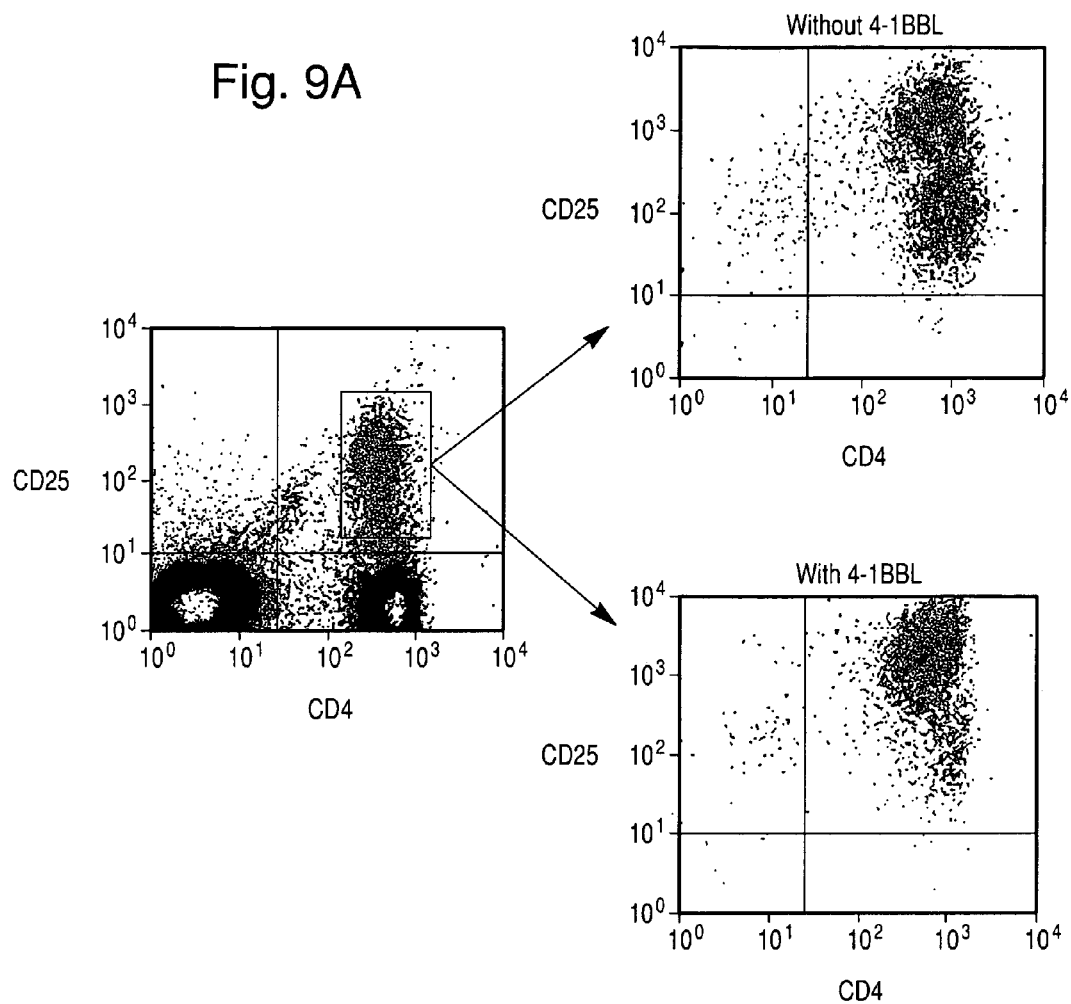
FIG. 9. Ex vivo expansion of Treg cells using 4-1BBL.
Figure 9B:
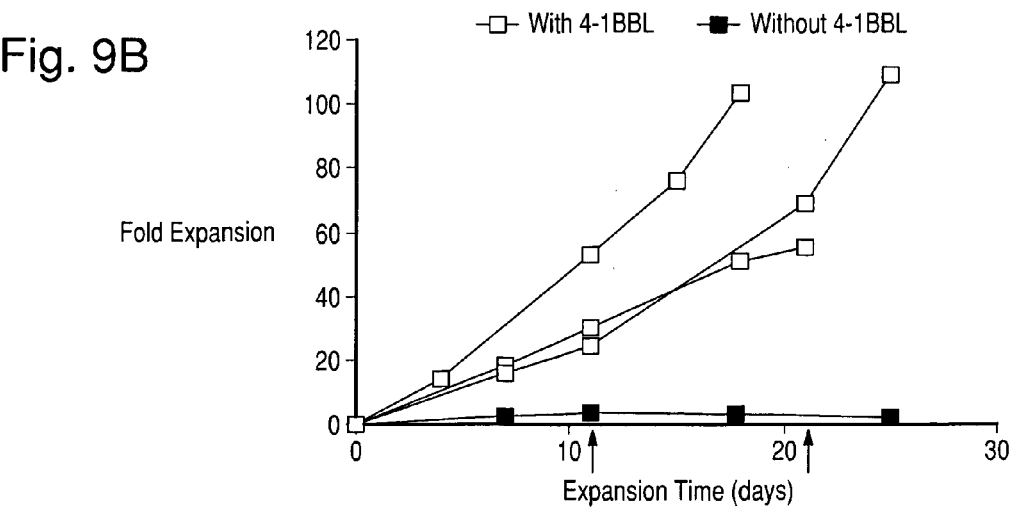
Figure 10:
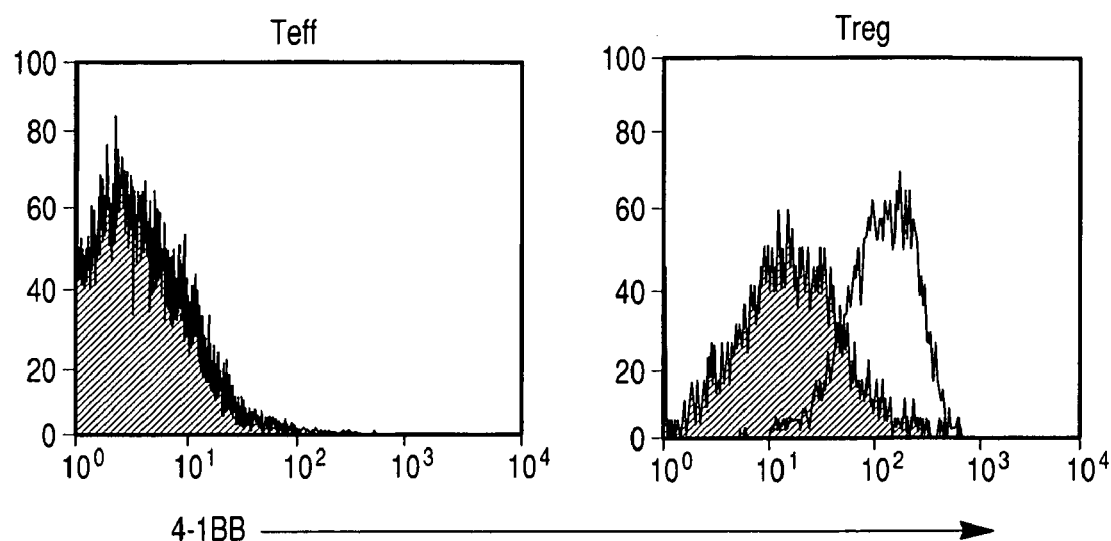
FIG. 10 illustrates the expression of 4-1BB receptor on Treg cells expanded ex vivo in accordance with the invention. Teff and Treg cells maintained in culture for 18-24 days were stained with antibody to 4-1BB and analyzed by flow cytometry. Black filled populations are isotype controls.

Treg Expansion Using a CSA-4-1BBL Conjugate $CD4^+CD25^+$ $T_{reg}$ cells were sorted from the spleens of BALB/c mice (FIG. 9A) using fluorescent activated cell sorting (FACS) and activated with anti-CD3 antibody (0.5 µg/ml), CSA-4-1BBL (1 µg/ml), and IL-2 (25 IU/ml) in the presence of syngeneic APC. Cells were then maintained at ~1×$10^6$ cell/ml with IL-2 supplemented medium every 3 days for 10-12 days. The cultures were then subjected to another round of activation followed by maintenance with IL-2. As shown in FIG. 9, this regimen allowed for 55- to 110-fold expansion of Treg cells within 18-24 days, with a 110-fold expansion within 25 days (FIG. 9B). Treg cells maintained under the same conditions but without CSA-4-1BBL conjugate only minimally expanded. Expanded Treg cells formed a homogenous population composed of $CD4^+CD25^{bright}$ cells (FIG. 9A, bottom right panel) expressing high levels of FoxP3 protein (determined by RT-PCR or anti-FoxP3 antibody) as well as Fas, CD62L, GITR, CD25, CD28, and cell surface TGF-β (data not shown) and suppressed allogeneic responses as well as polyclonal activation of T cells using anti-CD3 stimulation (data not shown). In contrast, cultures without 4-1BBL only showed a 2.5 fold expansion in the number of DP cells and showed heterogenous populations composed of $CD4^+CD25^{dim}$ and $CD4^+CD25^{bright}$ cells (FIG. 9A, top right panel). Unlike expanded $CD4^+$ SP T cells, Treg cells expressed high levels of 4-1BB. FIG. 10 (black filled populations are isotype controls).

EXAMPLE 3

Expanded Treg Cells Prolong Islet Allograft Survival

Figure 11:
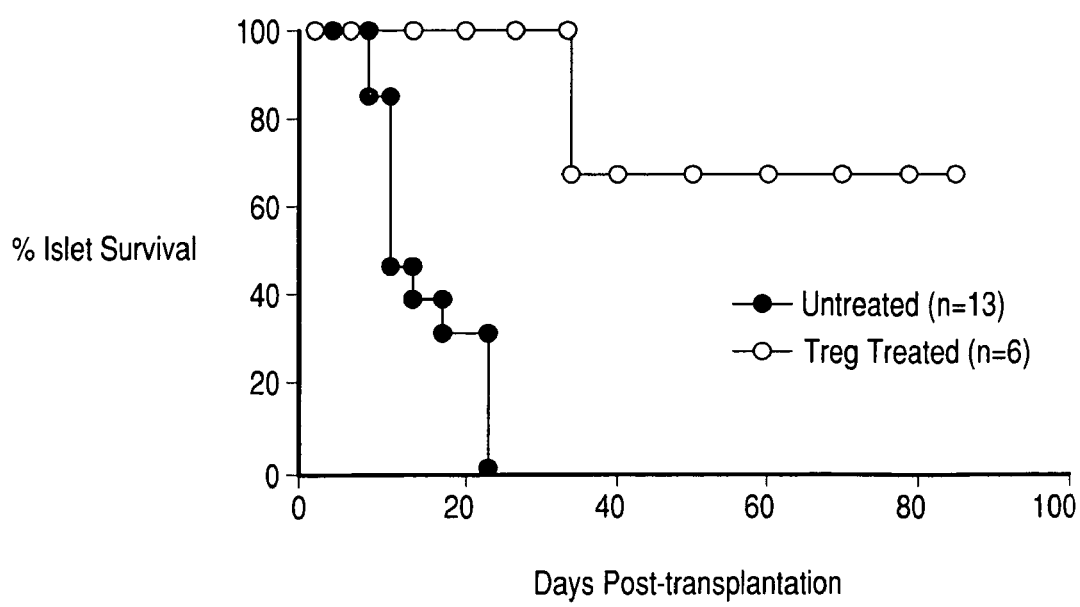
FIG. 11 demonstrates the prevention of allograft rejection by Treg cells expanded ex vivo in accordance with the invention. Naive BALB/c mice rendered diabetic by a single injection of streptozotocin were adoptively transferred with 5-8× 10$^6$ expanded Treg cells one day prior to transplantation with allogeneic C57BL/6 islets (○). Control animals did not receive Treg cells but were transplanted with allogeneic islets (•). Rejection was confirmed by two consecutive blood glucose readings above 300 mg/dL. Survival was compared using Kaplan-Meier log rank test ($p<0.05$).

To test the therapeutic effect of polyclonally expanded Treg cells, chemically induced (by streptozotocin) diabetic BALB/c mice were adoptively transferred with 5-10×10⁶ Treg cells expanded in culture as described above for 20-25 days and then given transplants of fully mismatched C57BL/6 allogeneic islets 24 hrs later. Animals were monitored for blood glucose level three times per week. All Treg-treated animals (○) had prolonged survival (MST=68.7±10 days) with over ⅓ (66%) not rejecting their grafts within ~85 days of the observation period. FIG. 11. In marked contrast, all control animals (•) without Treg cell therapy acutely rejected their grafts (MST=16.6±2.7 days).

EXAMPLE 4

Expanded CD4⁺CD25⁺ Treg Cells are Suppressive

Figure 12A:
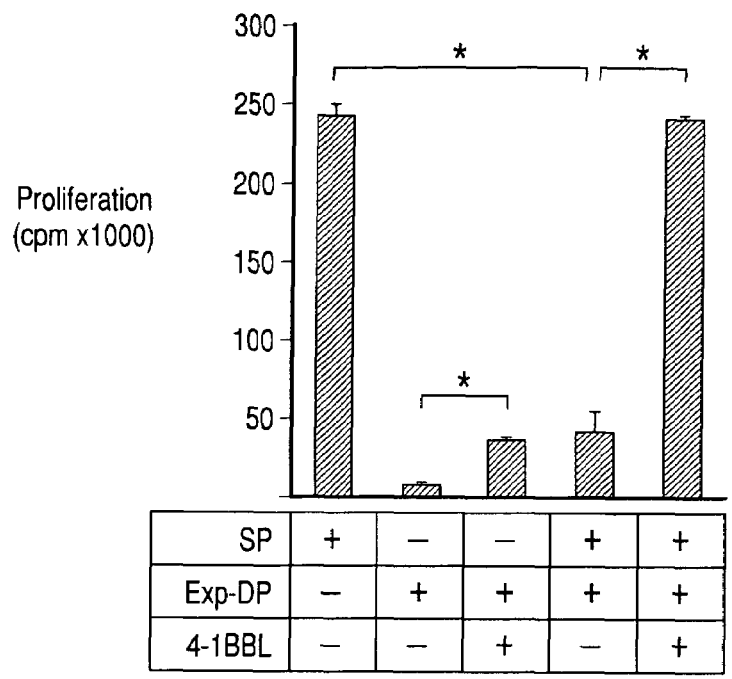
FIGS. 12A-B. Expanded Treg cells suppress polyclonal or antigen-specific proliferation of Teff cells ex vivo. (A) Polyclonal (anti-CD3 Ab) suppression assays were performed as described in FIG. 9 in the presence or absence of 1 μg/ml 4-1BBL with expanded Treg cells (Exp-DP). (B) Alloantigen suppression assays. Spleen and peripheral lymph node cells from naïve BALB/c mice (responders) were cocultured with irradiated spleen cells from naïve C57BL/6 mice (stimulators) and expanded Treg cells (Exp-DP) at indicated ratios for 5 days. *p<0.05 compared to each other and controls. Data (mean±SD) are representative of 4 independent experiments for A and 2 independent experiments for B with similar results.

The function of expanded Treg cells was characterized in a classical suppression assay using CD3 stimulation. Similar to naïve Treg cells, expanded cells remained anergic in response to CD3 stimulation, were capable of suppressing the polyclonal proliferation of CD4⁺ Teff cells, and this suppressive function could be inhibited by 4-1BBL (FIG. 12A).

Figure 12B:
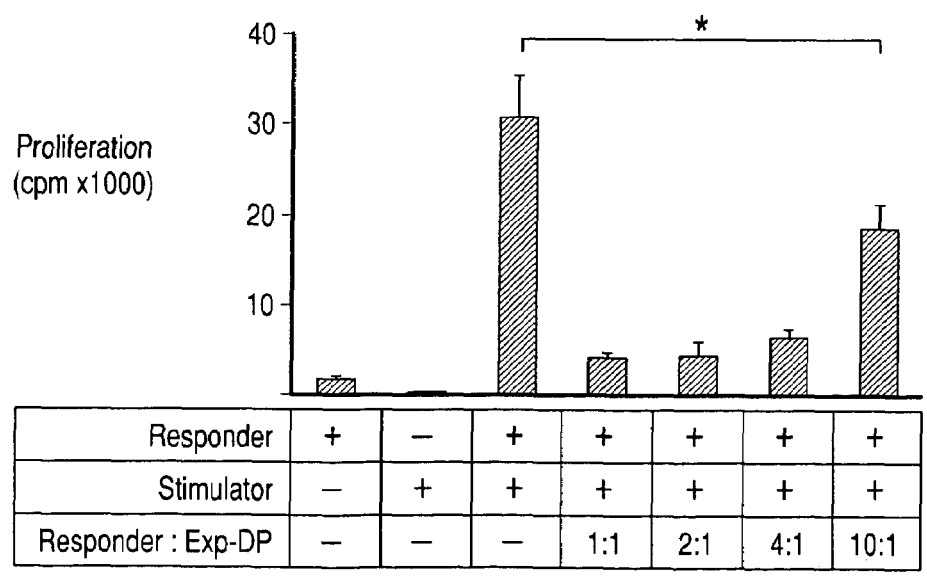

Further evidence for the suppressive function of Treg cells expanded in accordance with the invention as described above, was provided using mixed lymphocytes reactions. Spleen and peripheral lymph node cells from naïve BALB/c mice were used as responders while irradiated splenocytes from naïve C57BL/6 mice were used as stimulators. There was a potent inhibition of alloantigen-driven Teff proliferation by the expanded Treg cells that was significant (p<0.05) even at a 10:1 responder to Treg ratio (FIG. 12B). This indicates that expanded Treg cells were endowed with the classical suppressive function ascribed to naturally occurring Treg cells. Taken together, these data demonstrate that Treg cells expanded with a CSA-4-1BBL conjugate are suppressive and behave in a similar fashion to naturally occurring Treg cells.

EXAMPLE 5

A. Synergistic Effects of 4-1BBL and IL-2 on Treg Cells

Figure 13A:
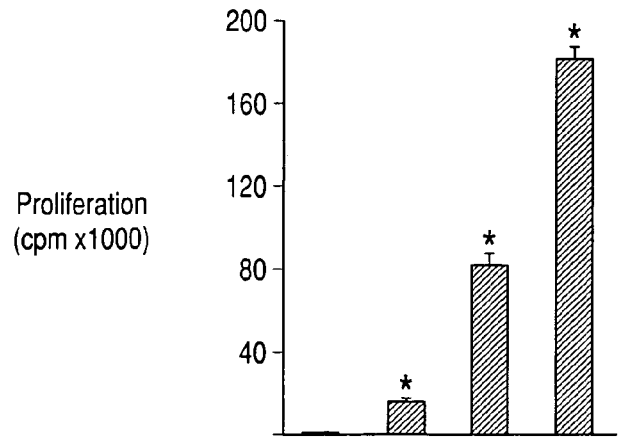
FIGS. 13A-C. Synergistic effect of TCR, 4-1BB, and IL-2R signaling for the expansion of Treg cells.

Sorted naïve DP cells were co-cultured with irradiated syngeneic splenocytes in the presence of 0.5 μg/ml anti-CD3 antibody for 3 days. Cultures were supplemented with 25 U/ml of IL-2, 1 μg/ml CSA-4-1BBL, or a combination of both. The addition of either IL-2 or 4-1BBL to Treg cultures was sufficient to induce Treg cell (DP) proliferation; however, there was a 4-fold proliferative increase in cultures supplemented with 25 U/ml IL-2 compared to those supplemented with 1 μg/ml of 4-1BBL. FIG. 13A. Combined use of 4-1BBL and IL-2 yielded a maximal proliferative response (2-fold over IL-2 alone; FIG. 13A), indicating that these two proteins act synergistically to promote the proliferation of Treg cells.

Figure 13B:
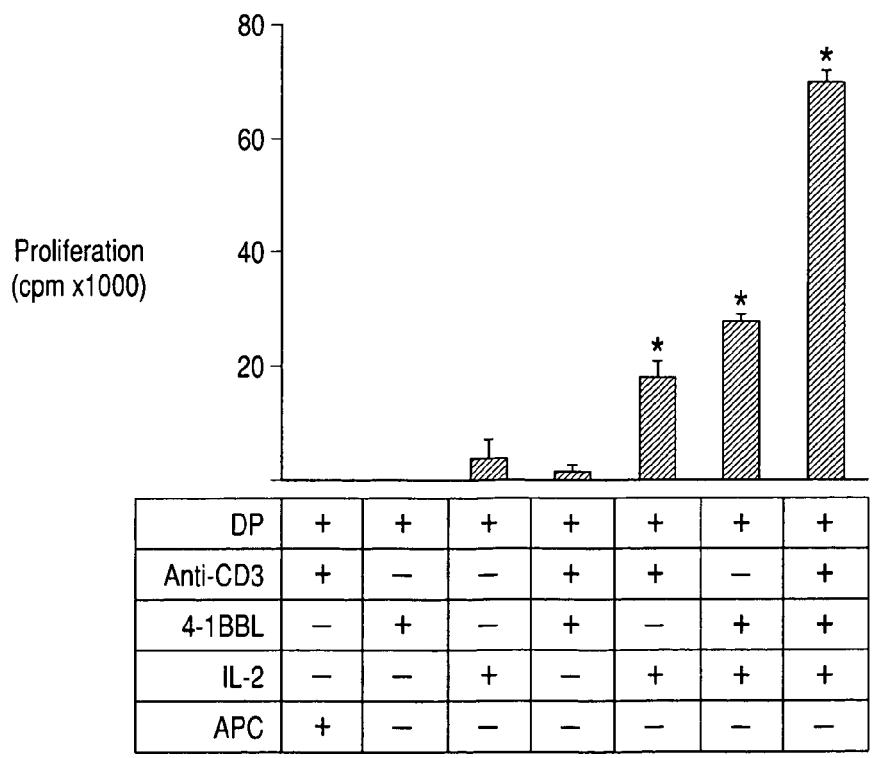

The individual contribution of each of Signals 1, 2 and 3 to Treg proliferation in a culture system without APCs also was examined. In this assay, Signal 1 was provided by soluble anti-CD3 antibody, Signal 2 by 4-1BBL, and Signal 3 by IL-2. Sorted naïve DP cells were used alone without irradiated splenocytes and the cultures were supplemented with anti-CD3 antibody, CSA-4-1BBL, and/or IL-2. As shown in FIG. 13B and summarized in Table 1, stimulating Signal 1 or 2 alone was inefficient in inducing Treg cell proliferation while stimulating Signal 3 resulted in moderate expansion. Stimulating both Signals 1 and 2 also had a minimal effect of Treg expansion. However, stimulating Signal 1 or 2 in combination with Signal 3 stimulation by IL-2 had a significant proliferative effect, with the most dramatic effect on Treg proliferation (up to 110-fold expansion in 2-3 weeks) observed when all three signals were stimulated. The expanded Treg cells were all CD25$^{bright}$ and expressed higher levels of CD28, 4-1BB, GITR, Fas, CD62L, membrane-bound TGF-β, and FoxP3 as compared to DP cells expanded without 4-1BBL.

TABLE 1

| Signal | 1 | 2 | 3 | 1 + 2 | 1 + 3 | 2 + 3 | 1 + 2 + 3 |
|---|---|---|---|---|---|---|---|
| Effect | − | − | + | + | ++ | +++ | ++++++ |

These results suggest that there is a hierarchy in the effect of stimulating Signals 1, 2, and 3 on the proliferation of Treg cells. Stimulating Signal 1 or 2 alone has virtually no effect, while stimulating Signal 3 (via IL-2) alone or in addition to Signals 1 and/or 2 has a significant effect. Stimulating all three signals has the most pronounced effect, followed by stimulation of Signals 2 and 3, then 1 and 3.

B. IL-2 Upregulates the Expression of 4-1BB Receptor on CD4⁺CD25⁺ Treg Cells

Sorted CD4⁺CD25⁺ (DP) Treg and CD4⁺CD25³¹ (SP) Teff cells were cultured in the presence or absence of IL-2 and/or irradiated APCs for 2 days. Cells were then harvested and analyzed in flow cytometry for the expression of 4-1 BB. Only 22% of the freshly sorted Treg cells expressed 4-1 BB while non of the Teff cells scored positive for this receptor. The expression of 4-1 BB was down-regulated to background levels (2%) when cells were cultured alone for 2 days. Culturing Treg cells in the presence of irradiated APCs had a minimal effect on maintaining the constitutive expression of 4-1BB on Treg cells (8%). In marked contrast, addition of IL-2 to the cultures of Treg cells resulted in not only the maintenance, but also moderate upregulation (29% vs 22% for fresh cells) of 4-1BB receptor. Addition of irradiated APCs further enhanced the effect of IL-2 on the upregulation of 4-1 BB expression (53%).

Figure 13C:
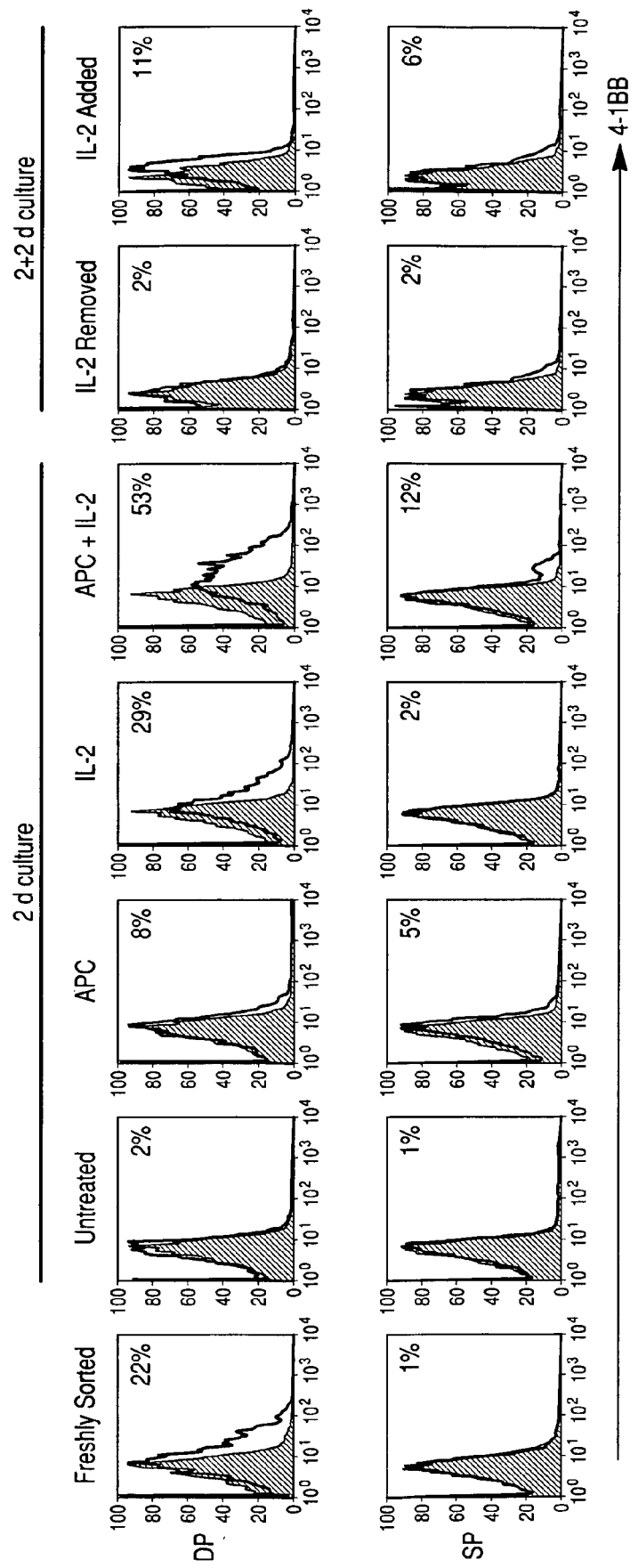

To further probe the role of IL-2 in the maintenance/upregulation of 4-1BB on Treg cells, cells cultured in the presence of APCs plus IL-2 were washed extensively and recultured in the absence of IL-2 for 2 days (FIG. 13C, last histogram in the upper panel). All Treg cells down-regulated 4-1 BB expression to background levels. Regulation of 4-1 BB expression by IL-2 was specific for Treg cells as similar treatments were ineffective in changing the pattern of 4-1BB expression on Teff cells (FIG. 13C, bottom panel). These results to our knowledge are the first demonstration that IL-2 maintains/upregulates the expression of 4-1 BB on Treg cells and provide a mechanistic basis for the observed synergy between IL-2 and 4-1 BBL on the proliferation of Treg cells ex vivo.

EXAMPLE 6

Construction of A Functional TGF-β-CSA Conjugate

A conjugate comprising CSA and the active form of TGF-β1 was generated following the general protocol outline above. The TGF-β-CSA conjugate showed potent inhibitory activity on the proliferation of T cells when used in MLR assay (FIG. 14) or polyclonal activation with anti-CD3 (data not shown). These data demonstrate that the TGF-β-CSA conjugate is active and can be used to block antigen-specific proliferation, and as such will be useful in the expansion of Treg cells in vitro and in vivo.

EXAMPLE 7

Non-Selective Treg Expansion with 4-1BBL, CD80 & IL-2

As discussed above, the development of diabetes in NOD mice is understood to involve a breakdown in the function of Treg cells controlling pathogenic Teff cells. NOD mice have a lower number of Treg cells in the periphery as compared with diabetes resistant strains, and show a decline in the amount and function of Treg cells with age that correlates with the onset of diabetes. Although the exact mechanisms responsible for this are unknown, defects in the ability of APCs to regulate the development and maintenance of Treg cells may play a role. Consistent with this contention are the observations that (i) DCs in NOD show decreased expression of costimulatory molecules, such as CD80, that are important for the development and function of $T_{reg}$ cells and (ii) various biological agents, such as helminthes and viruses, that have protective effects on the incidence of diabetes in NOD mice may induce Treg cells via the modulation of DCs.

This example illustrates the selective expansion of $T_{reg}$ cells in NOD mice using conjugates comprising CD80 and/or 4-1 BBL and IL-2, and shows the efficacy of this approach for the prevention of Type 1 diabetes in NOD. The conjugates will preferentially bind Treg cells and expand them in a therapeutic manner.

The stages of diabetes in NOD can roughly be categorized as preinsulitis (1-3 weeks), insulitis (4-8 weeks), prediabetes (8-24 weeks) and diabetes (>28 weeks). These stages vary depending on the animal facility where they are housed. Prediabetic female NOD mice are selected since these animals will have full blown autoimmunity as well as the anticipated defects in Treg cells ands APCs, and the prevention of diabetes in these animals will have clinical ramifications.

To expand Treg cells in vivo, animals will be injected intravenously with conjugates comprising CD80 and IL-2 or 4-1BBL and IL-2, in various combinations, frequencies, and doses. A core streptavidin (CSA)/IL-2 conjugate will be used as a control. The conjugates will be prepared by mixing CSA-CD80 or CSA-4-1 BBL conjugates with biotinylated IL-2 at 1:1 molar ratio in PBS before use.

Using a superagonistic antibody to CD28, it was found that the peak Treg expansion response occurred 3 days after injection. Thus, animals will be injected with conjugates every 3 days and bled right before the next conjugate injection to assess the level of Treg expansion. Typing will be performed using antibodies against CD4 and FoxP3 in flow cytometry. Once the time of peak Treg cell expansion is determined from this blood analysis, animals will be sacrificed for the collection of peripheral lymph nodes, including pancreatic lymph nodes, spleen, and pancreas. Spleen and lymph nodes as well as GIL isolated from the pancreatic islets of each animal will be processed into single cell suspension and typed by multiparameter flow cytometry using various cell surface, CD4, CD8, 4-1BB, CD62L, TGF-β, CD25, and intracellular, FoxP3, IL-10, and IFN-γ markers to have a global perspective of the status of the T cells.

The treatment of prediabetic NOD mice as described herein will rapidly expand Treg cells over Teff cells. The provision of costimulatory and survival signals via CD80, 4-1BBL and IL-2 is expected to result in a rapid expansion of Treg cells. This effect may further be accentuated by 4-1BBL activation of DCs, which can contribute to the expansion and/or rescue of Treg cell function. The resulting expansion may be systemic, or Treg cells may preferentially home to pancreatic lymph nodes and pancreas for a protective response. Expanded Treg cells will express all of the classical Treg cell markers, such as cell surface TGF-β, CD25, 4-1BB, and intracellular IL-10.

EXAMPLE 8

Prevention of Type 1 Diabetes Via Non-Selective Treg Expansion

The ability of Treg expansion in prediabetic NOD animals to prevent or delay the onset of Type 1 diabetes is demonstrated as follows. Prediabetic NOD (12 week-old) animals will be treated with conjugates comprising CD80 and IL-2 or 4-1BBL and IL-2, as described above, and under conditions that allow for the robust expansion of Treg cells, as determined in the above studies. Animals will be monitored for the development of diabetes for 25 weeks (by which time over 85% of unmanipulated females in our colony develop diabetes). Two consecutive daily measurements of blood glucose levels over 250 mg/dl will be considered as a confirmation of diabetes. Animals that fail treatment as well as those that do not develop diabetes by 28 weeks will be sacrificed and various tissues will be harvested for Treg phenotyping as well as immunohistochemistry to determine the status of the disease (none vs. periinsulitis vs. insulitis). Animals left untreated or treated with CSA-IL-2 conjugate will serve as controls for the incidence of diabetes.

The expansion of Treg cells in prediabetic animals in accordance with the invention will prevent the development of diabetes. A sustained preventive effect may require periodic treatment with the conjugates to maintain a high ratio of Treg to autoimmune Teff cells. Long-term nondiabetic animals may completely lack the disease or may have periinsulitis without clinical manifestations. Diseased animals are expected to have a reduced number of Treg cells expressing lower amounts of membranous TGF-β and secreted IL-10. These animals may also contain high numbers of IFN-γ secreting CD4$^+$ and CD8$^+$ $T_{eff}$ cells.

EXAMPLE 9

Selective Treg Expansion with 4-1BBL & an Autoantigen

Although Treg cells are capable of suppressing immune responses in an antigen-nonspecific fashion, antigen-driven activation and expansion of Treg cells may offer advantages in terms of specificity and increased efficacy. This example illustrates the selective expansion of autoantigen-specific Treg cells using conjugates comprising 4-1BBL and the autoantigen GAD in conjunction with conjugates comprising CD80 and IL-2 and TGF-β and IL-2, for effective delivery of the autoantigen to DCs. Rapamycin also is used to enhance efficacy.

As discussed above, DCs constitutively express 4-1BB, and signaling through this receptor via binding by the 4-1 BBL/GAD conjugate will result in activation of DCs, upregulation of costimulatory molecules, and synthesis and secretion of various cytokines required for an effective T cell response. Additionally, CD80 and IL-2 will preferentially expand Treg cells, which constitutively express CD28 and CD25. At the same time, the use of TGF-β and IL-2 will block the function and expansion of Teff cells while enhancing the function and expansion of Treg cells. Rapamycin will augment the effects of TGF-β by blocking the proliferation of and facilitating apoptosis of Teff cells without major effects on the expansion of Treg cells. Thus, the recognition of autoantigen in the presence of TGF-β and rapamycin will selectively block the activation and function of Teff cells while favoring the development and expansion of antigen-specific Treg cells, while the 4-1BBL will activate DCs for a sustained Treg response.

Twelve week-old prediabetic animals are administered (by intravenous injection) conjugates comprising 4-1BBL and GAD, CD80 and IL-2, and TGF-β and IL-2, in various combinations, frequencies, and doses. The conjugates are prepared by mixing CSA-4-1BBL conjugates with biotinylated GAD (prepared as described above) or by mixing CSA-CD80 or TGF-β-CSA conjugates with biotinylated IL-2 as described above. Rapamycin will be given intraperitoneally at a dose of 1.5 mg/kg everyday for the duration of the treatment with conjugates.

Animals are monitored for the peak expansion of Treg cells in the blood using antibodies to CD4 and FoxP3 in flow cytometry. Once the time of peak Treg response is determined, animals are euthanized for the collection of peripheral lymph nodes, including pancreatic lymph nodes, spleen, and pancreas and multiparameter typing for various cell surface and intracellular markers as described in Example 7 above. NOD recipients left untreated or treated with various combinations of conjugates will serve as controls. Once, the most potent conditions for the expansion of Treg cells are determined, they are used to treat another set of animals for the prevention of diabetes.

Combined treatment with all four conjugates (4-1BBL/GAD; 4-1BBL/IL-2; CD80/IL-2; TGF-β/IL-2) and rapamycin is expected to be a potent regimen for antigen-specific expansion of Treg cells and for the prevention of diabetes in prediabetic animals. The 4-1 BBL/GAD conjugate will deliver the GAD autoantigen to DCs, leading to protein processing, activation of DCs, and presentation of GAD to Treg cells as well as pathogenic Teff cells. TGF-β and rapamycin will work synergistically to block the activation and expansion of autoantigen-specific Teff cells while facilitating the activation and expansion of Treg cells by CD80/IL-2 as well as 4-1BBL/IL-2 and/or 4-1BBL/GAD conjugates. TGF-β and rapamycin also will facilitate the conversion of $CD4^+$ $CD25^-$ naïve T cells into Treg cells by inducing FoxP3 expression. Specific expansion of autoantigen-specific Treg cells will be achieved in groups treated with at least one of TGF-β or rapamycin since these two agents preferentially block Teff cell proliferation without a major effect on the expansion of Treg cells.

Expansion of Treg cells will correlate with the prevention of diabetes. Periodic repeated treatments with the conjugates may be useful to maintain the Treg pool. The use of additional autoantigens (e.g., conjugates comprising 4-1BBL and additional different autoantigen) may enhance the effects by expanding a broader class of Treg cells.

EXAMPLE 10

Selective Expansion of $T_{reg}$ Cells Using Decorated, Pulsed DCs

This example illustrates the use of DCs pulsed with a mixture of three diabetogenic autoantigens (GAD, ICA152, and NRP-A7) and decorated with TGF-β to expand Treg cells. This methodology can be used alone, or in conjunction with the costimulatory conjugates described above and/or in conjunction with rapamycin, as discussed above. The use of DCs pulsed with three autoantigens will elicit diverse types of Treg cells and the direct display of TGF-β on DCs will not only limit any possible toxicity associated with the systemic use of the soluble protein, but also will effectively expand and/or restore the function of Treg cells, leading to the prevention of diabetes in NOD.

Immature DCs are produced from the bone marrow of NOD using GM-CSF and IL-4, as described above. Cells are pulsed with a mixture of diabetogenic autoantignes: GAD 65, islet cell autoantigen (ICA) 512 peptide, and the NRP-A7 peptide. Immature DCs are driven to maturation by overnight incubation with 4-1BBL and characterized by flow cytometry using antibodies against CD11c and various maturation markers, such as higher levels of MHC class II, CD80, and CD86 molecules.

DCs are biotinylated (5 μM EZ-Link Sulfo-NHS-LC-Btioin, Pierce) and decorated with TGF-β-CSA (100 ng/$10^6$ cells) as described above, and injected intravenously into prediabetic animals under the cover of rapamycin. DCs are injected intravenously at various doses, starting with $5 \times 10^5$ cells/animal. (This dose of DCs pulsed with two GAD peptides and one hsp60 peptide has been shown to be effective in reducing the incidence of diabetes in prediabetic NOD mice.)

In a related experiment, CD80/IL-2 and 4-1BBL/IL-2 conjugates made as described above are also (in conjunction with the pulsed, decorated DCs) administered to augment the tolerogenic effect.

Unmodified cells and cells decorated with CSA are used as controls. Animals are analyzed for the expansion of Treg cells and prevention of diabetes as described above.

Treatment with undecorated or TGF-β-decorated pulsed DCs and rapamycin will expand Treg cells, leading to the prevention of diabetes. As discussed above, TGF-β and rapamycin may work synergistically to block the activation and expansion of autoantigen-specific Teff cells while facilitating the activation and expansion of Treg cells or their conversion from $CD4^+CD25^-$ T cells. The optional use of CD80/IL-2 and 4-1BBL/IL-2 conjugates may further augment this effect.

EXAMPLE 11

Selective Expansion of Treg Cells Using Decorated BMC

This example illustrates the use of foreign (allogeneic or xenogeneic) bone marrow cells (BMC) decorated with TGF-β to expand Treg cells. This methodology can be used alone, or in conjunction with the costimulatory conjugates described above and/or in conjunction with rapamycin, as discussed above. The use of BMC will not only expand Treg cells, but also will establish mixed chimerism that will control autoimmunity and allow for the regeneration of pancreatic beta cells, leading to the prevention and/or treatment of diabetes. The use of foreign BMC decorated with TGF-β in conjunction with conjugates will expand Treg cells, which in turn will lead to the prevention of BMC rejection and the establishment of mixed chimerism that will control both auto- and alloreactivity.

BMC are biotinylated (5 μM EZ-Link Sulfo-NHS-LC-Btioin, Pierce) and decorated with TGF-β-CSA (100 ng/$10^6$ cells) as described above, and injected intravenously into prediabetic animals under the cover of rapamycin. BMCs are injected intravenously at various doses, starting with $5 \times 10^6$ cells/animal.

In a related experiment, CD80/IL-2 and 4-1BBL/IL-2 conjugates made as described above are also (in conjunction with the decorated BMCs) administered to augment the tolerogenic effect.

Unmodified cells and cells decorated with CSA are used as controls. Animals are analyzed for the expansion of Treg cells, mixed chimerism, and prevention of diabetes as described above.

Treatment with undecorated or TGF-β-decorated BMC and rapamycin will expand Treg cells, leading to the prevention of diabetes. As discussed above, TGF-β and rapamycin may work synergistically to block the activation and expansion of autoantigen-specific Teff cells while facilitating the activation and expansion of Treg cells or their conversion from $CD4^+CD25^-$ T cells. The optional use of CD80/IL-2 and 4-1BBL/IL-2 conjugates may further augment this effect.

EXAMPLE 12

Chimeric 4-1BBL (CSA4-1BBL) Inhibits the Suppressive Function of Treg Cells While Driving the Proliferation of Both Treg and Teff Cells We investigated the role of 4-1BB signaling in Treg function using chimeric 4-1BBL protein (CSA-4-1BBL). Sorted $CD4^+CD25^+$ double positive (DP) T cells from naïve BALB/c mice markedly inhibited the proliferative response of single positive (SP) $CD4^+CD25^-$ Teff cells induced by CD3 stimulation in [$^3$H]thymidine incorporation-based coculture experiments (FIG. 15A). This suppressive effect was effectively ($p<0.05$) and specifically inhibited by supplementing cultures with 1 μg/ml chimeric 4-1BBL (CSA-4-1BBL), but not CSA control protein used at an equimolar concentration.

Figure 2B:
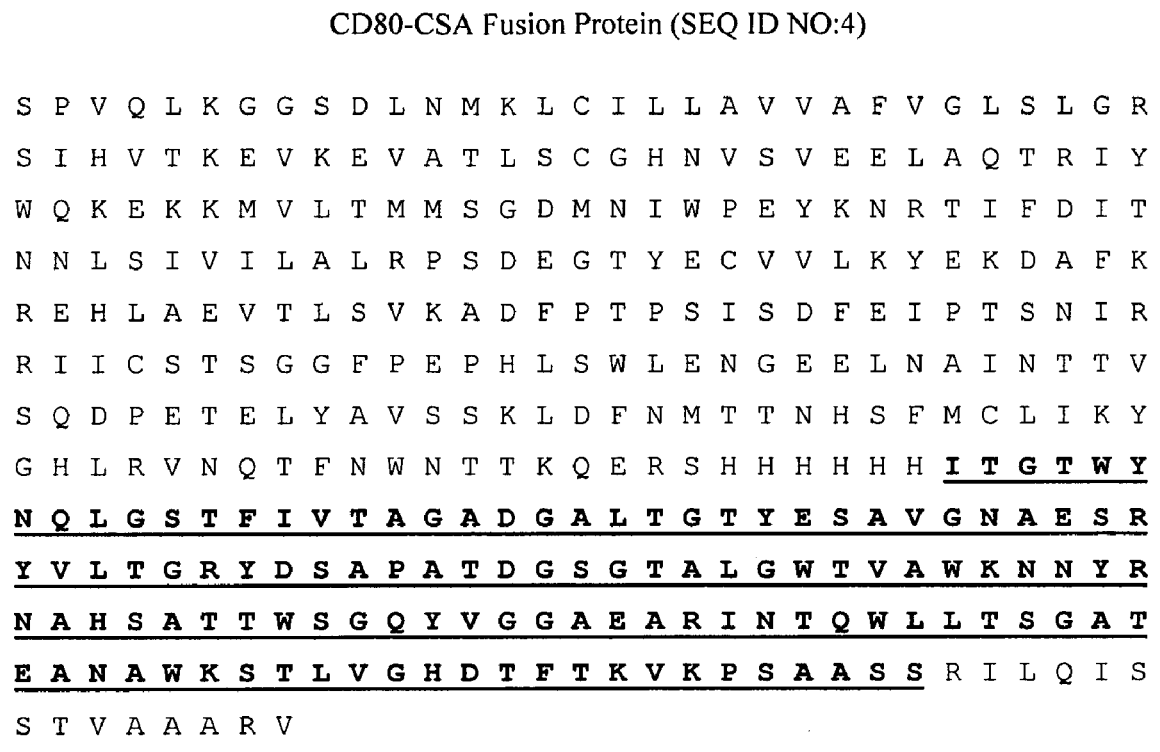

To test whether the observed inhibition of suppression by chimeric 4-1BBL was due to the restoration of the proliferative response of $CD4^+$ Teff cells or induced proliferation of Treg cells, SP cells were labeled with CFSE (carboxyfluorescein succinimidyl ester) and used in coculture experiments (FIG. 2B, top panel). Costimulation with chimeric 4-1BBL resulted in increased proliferation of $CD4^+$ Teff cells (75%) as compared with control (56%). Addition of Treg cells to the cultures markedly reduced the proliferation of $CD4^+$ Teff cells (30%), which was partially restored by 4-1BBL (62%). The lack of full restoration of $CD4^+$ Teff cell proliferation in response to 4-1BBL costimulation in coculture experiments may be due to Treg cells competition with Teff cells for the chimeric protein and/or other factors, such as IL-2. In a parallel experiment, CFSE labeled DP cells were used in coculture experiments to test whether Treg cells also show proliferative response to 4-1BBL stimulation (FIG. 15B, bottom panel). There was significant proliferation of Treg cells in response to 4-1BBL when cultured alone (44% compared to 17% of the control) or in combination with SP Teff cells (58% vs. 28% of controls). Taken together, these results demonstrate that 4-1BBL drives the proliferation of Treg cells while inhibiting their suppressive function.

EXAMPLE 13

Phenotype of Expanded $CD4^+CD25^+$ Treg Cells

Cells expanded in Example 2 were further characterized for classical Treg cell markers using flow cytometry. Expanded Treg cells expressed CD25, 4-1BB, CD28, GITR, Fas, CD62L, and cell-surface TGF-β. Importantly, all of these markers were markedly upregulated on 4-1BBL expanded Treg cells as compared with those expanded without 4-1BBL (FIG. 9A and 16A). Expanded Treg cells also expressed the signature transcriptional factor FoxP3 as assessed by RT-PCR (FIG. 16B) as well as intracellular staining (FIG. 16C). Importantly, Treg cells expanded in the presence of 4-1BBL had increased levels of FoxP3 protein as compared with Treg cells without 4-1BB stimulation. Taken together these data demonstrate that 4-1BBL stimulation upregulates all cell surface markers as well as FoxP3 involved in the development/function of naturally occurring Treg cells.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following exemplary embodiments and the claims which follow.

Exemplary Embodiments

1. A combination comprising:
   (A) one or more conjugates selected from the group consisting of:
   (a) a first conjugate comprising (i) a first conjugate member comprising a 4-1BBL polypeptide and (ii) second conjugate member comprising a first member of a binding pair;
   (b) a second conjugate comprising (i) a first conjugate member comprising a CD80 polypeptide and (ii) a second conjugate member comprising a first member of a binding pair; and
   (c) a third conjugate comprising (i) a first conjugate member comprising a TGF-β polypeptide and (ii) a second conjugate member comprising a first member of said binding pair; and (B) one or more conjugates selected from the group consisting of:
- (a') a fourth conjugate comprising (i) a first conjugate member comprising an anti-CD3 antibody and (ii) a second conjugate member comprising a second member of said binding pair;
- (b') a fifth conjugate comprising (i) a first conjugate member comprising a cytokine and (ii) a second conjugate member comprising a second member of said binding pair;
- (c') a sixth conjugate comprising (i) a first conjugate member comprising an antigen and (ii) a second conjugate member comprising a second member of said binding pair; and
- (d') a seventh conjugate comprising (i) a first conjugate member comprising an anti-CD28 antibody and (ii) a second conjugate member comprising a second member of said binding pair.

In embodiment 1, the choice of cytokine is not limited.

2. The combination of embodiment 1, where said first member of said binding pair comprises avidin or streptavidin and said second member of said binding pair comprises biotin.
3. The combination of embodiment 1, wherein said first member of said binding pair comprises core streptavidin.
4. The combination of embodiment 1, wherein at least one of said first, second or third conjugates comprises a fusion polypeptide comprising said first conjugate member and said second conjugate member.
5. The combination of embodiment 1, wherein said cytokine is selected from the group consisting of IL-2, IL-4, or IL-7.
6. The combination of embodiment 1, wherein said antigen is an autoantigen.
7. The combination of embodiment 1, wherein said antigen is selected from the group consisting of insulin, collagen, myelin basic protein and MHC/antigen complexes.
8. The combination of embodiment 1, wherein said antigen is selected from the group consisting of a glutamic acid decarboxylase (GAD), an islet cell autoantigen (ICA), and autoantigen NRP-A7.
9. The combination of embodiment 1, wherein said conjugates are provided in separate compositions.
10. The combination of embodiment 6, wherein at least one of said separate compositions further comprises a pharmaceutically acceptable carrier, excipient or diluent.
11. The combination of embodiment 1, wherein said conjugates are provided in a single composition.
12. The combination of embodiment 8, wherein said single composition further comprises a pharmaceutically acceptable carrier, excipient or diluent.
13. The combination of embodiment 8, wherein at least one of said first, second or third conjugates is bound to at least one of said fourth, fifth, sixth or sevenths conjugates via binding between said first and second members of said binding pair.
14. A method of expanding Treg cells comprising contacting a population of Treg cells with
    (A) one or more conjugates selected from the group consisting of:
    - (a) a first conjugate comprising (i) a first conjugate member comprising a 4-1BBL polypeptide and (ii) second conjugate member comprising a first member of a binding pair;
    - (b) a second conjugate comprising (i) a first conjugate member comprising a CD80 polypeptide and (ii) a second conjugate member comprising a first member of a binding pair; and
    - (c) a third conjugate comprising (i) a first conjugate member comprising a TGF-β polypeptide and (ii) a second conjugate member comprising a first member of said binding pair; and (B) one or more conjugates selected from the group consisting of:
    - (a') a fourth conjugate comprising (i) a first conjugate member comprising an anti-CD3 antibody and (ii) a second conjugate member comprising a second member of said binding pair;
    - (b') a fifth conjugate comprising (i) a first conjugate member comprising a cytokine and (ii) a second conjugate member comprising a second member of said binding pair;
    - (c') a sixth conjugate comprising (i) a first conjugate member comprising an antigen and (ii) a second conjugate member comprising a second member of said binding pair; and
    - (d') a seventh conjugate comprising (i) a first conjugate member comprising an anti-CD28 antibody and (ii) a second conjugate member comprising a second member of said binding pair.

15. The method of embodiment 14, wherein said Treg cells comprise a receptor for at least one of said first, second or third conjugates, and wherein at least one of said first, second or third conjugates is conjugated to said Treg cells via binding between said first conjugate member and said receptor and at least one of said fourth, fifth, sixth and seventh conjugates is conjugated to said Treg cells via binding between said first and second binding pair members.
16. The method of embodiment 14, wherein said contacting is effected ex vivo.
17. The method of embodiment 16, wherein at least two of said conjugates are contacted with said Treg cells substantially simultaneously.
18. The method of embodiment 16, wherein at least two of said conjugates are provided in a single composition.
19. The method of embodiment 18, wherein at least one of said first, second or third conjugates is conjugated to at least one of said fourth, fifth, sixth, and seventh conjugates via binding between said first and second binding pair members.
20. The method of embodiment 16, wherein at least two of said conjugates are contacted with said Treg cells sequentially.
21. The method of embodiment 16, further comprising administering said expanded Treg cells to a patient.
22. The method of embodiment 14, wherein said contacting is effected in vivo by administering said conjugates to a patient.
23. The method of embodiment 14, wherein said population of Treg cells comprises Treg cells selected from the group consisting of CD4+ cells, CD25+ cells, and FoxP3+ cells.
24. The method of embodiment 23, wherein said population of Treg cells comprises a CD4+CD25+FoxP3+ cell.
25. The method of embodiment 21 or 22, wherein said patient is suffering from or at risk for an autoimmune disease.
26. The method of embodiment 25, wherein said patient is suffering from or at risk for Type 1 diabetes.
27. The method of embodiment 21 or 22, wherein said patient is a foreign graft patient.
28. The method of embodiment 21 or 22, further comprising administering rapamycin to said patient.

29. The method of embodiment 21 or 22, further comprising administering to said patient a composition comprising foreign cells displaying TGF-β.
30. The method of embodiment 29, further comprising administering rapamycin to said patient.
31. The method of embodiment 29, wherein said foreign cells are selected from the group consisting of splenocytes, pancreatic islet tissue, and bone marrow cells.
32. The method of embodiment 29, wherein said foreign cells are obtained by a method comprising:
    (a) contacting foreign cells with a bifunctional molecule comprising a first member of a binding pair and a molecule that binds to the surface of said cells to form modified foreign cells; and
    (b) contacting said modified foreign cells with a conjugate comprising TGF-β and a second member of said binding pair to form foreign cells displaying TGF-β.
33. The method of embodiment 14, where said first member of said binding pair comprises avidin or streptavidin and said second member of said binding pair comprises biotin.
34. The method of embodiment 14, wherein said first member of said binding pair comprises core streptavidin.
35. The method of embodiment 14, wherein at least one of said first, second or third conjugates comprises a fusion polypeptide comprising said first conjugate member and said second conjugate member.
36. The method of embodiment 14, wherein said cytokine is selected from the group consisting of IL-2 and IL-4.
37. The method of embodiment 14, wherein said antigen is an autoantigen.
38. The method of embodiment 14, wherein said antigen is selected from the group consisting of insulin, collagen, myelin basic protein and MHC/antigen complexes.
39. The method of embodiment 14, wherein said antigen is selected from the group consisting of a glutamic acid decarboxylase (GAD), an islet cell autoantigen (ICA), and autoantigen NRP-A7.
40. The method of embodiment 14, further comprising contacting said Treg cells with free IL-2.
41. The method of embodiment 14, further comprising contacting said Treg cells with free anti-CD3 antibody or free anti-CD28 antibody.
42. A method of obtaining pulsed dendritic cells displaying TGF-β comprising:
    (a) pulsing immature dendritic cells with an antigen, to obtained pulsed dendritic cells;
    (b) contacting said pulsed dendritic cells with a bifunctional molecule comprising a first member of a binding pair and a molecule that binds to the surface of said cells to form modified pulsed dendritic cells; and
    (c) contacting said modified pulsed dendritic cells with a conjugate comprising TGF-β and a second member of said binding pair to form pulsed dendritic cells displaying TGF-β.
43. The method embodiment 42, wherein said antigen is a diabetogenic autoantigen.
44. The method of embodiment 43, wherein said diabetogenic autoantigen is selected from the group consisting of a glutamic acid decarboxylase (GAD), an islet cell autoantigen (ICA), and autoantigen NRP-A7.
45. The method of embodiment 44, wherein said diabetogenic autoantigen is selected from the group consisting of GAD 65 and ICA 512.
46. The method of embodiment 45, comprising pulsing said immature dendritic cells with each of GAD65, ICA 512 and NRP-A7.
47. The method of embodiment 42, wherein said antigen is collagen.
48. The method of embodiment 42, wherein said antigen is myelin basic protein.
49. The method of embodiment 42, further comprising driving said pulsed dendritic cells to maturity.
50. The method of embodiment 49, wherein said driving comprises incubating said pulsed dendritic cells with 4-1BBL.
51. A population of antigen-pulsed dendritic cells displaying TGF-β.
52. A population of antigen-pulsed dendritic cells displaying TGF-β made by the method of embodiment 42.
53. A method of expanding Treg cells in a patient comprising administering to said patient a composition comprising antigen-pulsed dendritic cells displaying TGF-β.
54. A method of expanding Treg cells in a patient comprising administering to said patient a composition comprising pulsed dendritic cells displaying TGF-β made by the method of embodiment 42.
55. The method of embodiment 54, further comprising administering rapamycin to said patient.
56. A method of obtaining hematopoietic stem cells or bone marrow cells displaying TGF-β comprising:
    (a) contacting hematopoietic stem cells or bone marrow cells with a bifunctional molecule comprising a first member of a binding pair and a molecule that binds to the surface of said cells to form modified cells; and
    (b) contacting said modified cells with a conjugate comprising TGF-β and a second member of said binding pair to form cells displaying TGF-β.
57. The method of embodiment 56, wherein said first member of said binding pair comprises biotin and said second member of said binding pair comprises core streptavidin.
58. A method of expanding Treg cells in a patient comprising administering to said patient a composition comprising hematopoietic stem cells displaying TGF-β or bone marrow cells displaying TGF-β.
59. The method of embodiment 58, wherein said cells displaying TGF-β are made by a method comprising:
    (a) contacting hematopoietic stem cells or bone marrow cells with a bifunctional molecule comprising a first member of a binding pair and a molecule that binds to the surface of said cells to form modified cells; and
    (b) contacting said modified cells with a conjugate comprising TGF-β and a second member of said binding pair to form cells displaying TGF-β.
60. The method of embodiment 58, further comprising administering rapamycin to said patient.
61. The method of embodiment 58, wherein said patient is in need of tolerance induction to autoantigens, alloantigens, or xenoantigens; beta cell regeneration; prevention of foreign graft rejection; or treatment of a genetically inherited hematopoietic disorder.
62. A population of bone marrow cells displaying TGF-β.
63. A population of bone marrow cells displaying TGF-β made by a method comprising
    (a) contacting bone marrow cells with a bifunctional molecule comprising a first member of a binding pair and a molecule that binds to the surface of said cells to form modified cells; and (b) contacting said modified cells with a conjugate comprising TGF-β and a second member of said binding pair to form cells displaying TGF-β.
64. A population of hematopoietic stem cells displaying TGF-β.
65. A population of hematopoietic stem cells displaying TGF-β made by a method comprising (a) contacting hematopoietic stem cells with a bifunctional molecule comprising a first member of a binding pair and a molecule that binds to the surface of said cells to form modified cells; and
(b) contacting said modified cells with a conjugate comprising TGF-β and a second member of said binding pair to form cells displaying TGF-β.

What is claimed is:

1. A method of expanding Treg cells in a patient comprising administering to said patient a composition comprising cells displaying 4-1BBL, wherein said cells are hematopoietic stem cells, bone marrow cells, or dendritic cells; and wherein said cells displaying 4-1BBL comprise biotin bound to a fusion protein comprising 4-1BBL and avidin, streptavidin, or core streptavidin.

2. The method of claim 1, further comprising administering IL-2 to said patient.

3. The method of claim 1, further comprising administering rapamycin to said patient.

4. The method of claim 1, wherein said cells are bone marrow cells.

5. The method of claim 1, wherein said cells are allogenic.

6. The method of claim 1, wherein said fusion protein comprises the amino acid sequence of SEQ ID NO:6.

7. The method of claim 4, wherein said bone marrow cells are allogenic, and wherein said expanded Treg cells induce tolerance to said allogenic bone marrow cells.

8. The method of claim 1, further comprising administering to said patient a composition comprising cells displaying TGF-β.

9. The method of claim 1, wherein said patient is suffering from or at risk of developing a condition selected from the group consisting of:
   (a) type 1 diabetes;
   (b) rejection of transplanted grafts or cells;
   (c) graft versus host disease;
   (d) an autoimmune disease;
   (e) a genetically inherited hematopoietic disorder;
   (f) rheumatoid arthritis; and
   (g) multiple sclerosis.

\* \* \* \* \*